(12) United States Patent
Reddy et al.

(10) Patent No.: US 8,143,428 B2
(45) Date of Patent: Mar. 27, 2012

(54) HETEROARYL SULFONES AND SULFONAMIDES AND THERAPEUTIC USES THEREOF

(75) Inventors: E. Premkumar Reddy, Villanova, PA (US); M. V. Ramana Reddy, Upper Darby, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 1204 days.

(21) Appl. No.: 11/628,019

(22) PCT Filed: Jun. 8, 2005

(86) PCT No.: PCT/US2005/020023
§ 371 (c)(1),
(2), (4) Date: Nov. 28, 2006

(87) PCT Pub. No.: WO2005/123077
PCT Pub. Date: Dec. 29, 2005

(65) Prior Publication Data
US 2007/0232649 A1 Oct. 4, 2007

Related U.S. Application Data
(60) Provisional application No. 60/578,162, filed on Jun. 8, 2004.

(51) Int. Cl.
C07D 335/02 (2006.01)
C07D 311/00 (2006.01)
(52) U.S. Cl. .......................... 549/27; 549/400
(58) Field of Classification Search ............ 549/27, 549/400
See application file for complete search history.

(56) References Cited

U.S. PATENT DOCUMENTS

| | | | |
|---|---|---|---|
| 3,810,922 A * | 5/1974 | Dunbar | 549/285 |
| 4,743,508 A | 5/1988 | Masuda | 428/408 |
| 4,743,529 A | 5/1988 | Farid et al. | 430/281 |
| 4,743,531 A | 5/1988 | Farid et al. | 430/281 |
| 6,541,475 B2 | 4/2003 | Reddy et al. | 514/252.12 |

FOREIGN PATENT DOCUMENTS
EP 0 565 074 7/1993
WO WO93/14106 7/1993

OTHER PUBLICATIONS

Larsson, DN 75:63306 (1971).*
Abrahart, Dyes and their Intermediates, pp. 8-9 (1968).*
Cerqueira et al, "Synthesis of Photochromic Dyes Based on Annulated Coumarin Systems", Helv. Chim. Acta vol. 85 (2002).*
Balasubramanian et al., "Synthesis of beta-amino sulfones and alpha,beta unsatd. sulfones", J. Chem Sac, 3296-8, 1955.
Troger et al., "Synthesis of benzo-.alpha.-pyrone derivatives and the rupture of the pyrone ring in these compounds", Journal Fuer Praktische Chemie (Leipzig) 103, 163-87, 1921.

Merchant et al., "Synthesis of 3-coumaryl phenyl sulfones or sulfoxides" Journal of Heterocyclic Chemistry 18(2), 441-2, 1981.
Troger et al., "Synthesis of arylsulfone derivatives of naphtha-.alpha.-pyrones, hydroxynaphtho-.alpha.-pyrones and trihydroxybenzo-.alpha.-pyrones", Journal Fuer Praktische Chemie (Leipzig), 104, 311-34, 1922.
Database Crossfire Beilstein Beilstein Institut Zur Foerderung Der Chemischen Wissenscaften, Archiv Der Pharmzie, vol. 247, 1909, p. 643.
Database Crossfire Beilstein Beilstein Institut Zur Foerderung Der Chemischen Wissenscaften, Archiv Der Pharmazie, vol. 247, 1909, p. 643.
Hoogenboom, et al., "Chemistry of sulfoacetic acid derivatives. III. Reactions of derivatives of sulfoacetic acid, benzoylmethanesulfonic acid, and p-nitrophenylmethanesulfonic acid with salicylaldehydees", Journal of Organic Chemistry, 40(7), 880-3, 1975.
Mandour, et al., "Synthesis, antimicrobial and antiaflatoxigenic activities of new coumarin derivatives", Egyptian Journal of Pharmaceutical Sciences, 36(1-6), 71-85, 1995.
Merchant, et al. "Substitution in the benzopyrone series. II. Sulfonation of coumarin derivatives", Journal of the Indian Chemical Society, 34, 35-41, 1957.
Abd-El-Hafez, et al., "Synthesis of some new coumarin derivatives with evaluation of their antimicrobial activity", Egyptian Journal of Pharmaceutical Sciences, 35 (1-6) 1994.
Troger, et al., "Fluorescence", Journal Fuer Praktische Chemie (Leipzig), 106, 173-202, 1923.
Database Crossfire Beilstein Beilstein Institut Zur Foerderung Der Chemischen Wissenschaften.
Farid, et al., "Dye-sensitized photographic imaging system", Chemical Abstracts.
Fedosova, et al., "Sulfanilamide derivatives of coumarin", Zhurnal Obshchei Khimii, 18, 1459-66, 1948.
O. M. Abd-El-Hafez, et al., "Synthesis of Some New Coumarin Derivatives With Evaluation of Their Antimicrobial Activity", Egypt. J. Pharm. Sci., 1994, 35(1-6), 113-26.
V. Baliah, et al., "Synthesis of 5-Aryl-4,6-bis[alkoxycarbonyl]-1,3-dithiane 1,1,3-Tetroxides", Synthesis, 1981, 995-96.
S. Checchi, et al., "4-Hydroxycoumarins. VII. Reactivity of 4-chloro- and 4-hydroxycoumarin-3-sulfonyl chlorides", Gazz. Chim. Italia., 1967, 97(12), 1749-61.
A. A. El-Maghraby, et al., "Synthesis of Coumarin Sulphonamides, Sulphonates and Related Compounds", Egypt. J. Chem., 1984, 27(4), 459-69.

(Continued)

Primary Examiner — Andrew D. Kosar
Assistant Examiner — Raymond Covington
(74) Attorney, Agent, or Firm — Drinker Biddle & Reath LLP

(57) ABSTRACT

Compounds of Formula I:

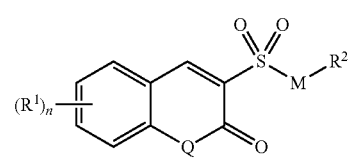

wherein $R^1$, $R^2$, M, Q and n are as defined herein, are useful as antiproliferative agents including, for example, as anticancer agents.

27 Claims, 1 Drawing Sheet

OTHER PUBLICATIONS

Chem. Abs. 136:135067, abstracting I. R. Gould, et al., "Energetics of electron-transfer reactions of photoinitiated polymerization: dye-sensitized fragmentation of N-alkoxypyridinium salts", *Helv. Chim. Acta.*, 2001, 84(9), 2796-812..

A. E. Hassan et al., "Reactions With Coumarin-3,6-Disulphonyl Chloride", *Modelling Measurement & Control, C.*, 1995, 47(1), 49-54.

B. E. Hoogenboom et al., "Chemistry of Sulfoacetic Acid Derivatives. III. Reactions of Derivatives of Sulfoacetic Acid, Benzoylmethanesulfonic Acid, and *p*-Nitrophenylmethanesulfonic Acid with Salicylaidehydes", *J. Org. Chem.*, 1975, 40(7), 880-83.

Chem. Abs. 137:369996 abstracting I. I. Ismail, et al., "Reactions with sulphanilamide", *Afinidad*, 2002, 59(499), 211-15.

A. H. Mandour, et al., "Synthesis, Antimicrobial and Antiaflatoxigenic Activities of New Coumarin Derivatives", *Egypt. J Pharm. Sci.*, 1995, 36(1-6), 71-85.

J. R. Merchant, et al., "Substitution in the Benzopyrone Series. IV. Sulfonation of Coumarin Derivatives", *J. Org. Chem.*, 1957, 22, 884-87.

J. R. Merchant, et al., "Substitution in the Benzopyrone Series. Part II. Sulphonation of Coumarin Derivatives", *J. Ind. Chem. Soc.*, 1957, 34(1), 35-41.

N.S. Reddy, et al., "Novel coumarin-3-(N-aryl)carboxamides arrest breast cancer cell growth by inhibiting ErbB-2 and ERK-1", *Bioorg. Med Chem. Lett.*, 2005, 13, 3141-47.

Chem. Abs. 61:14627d-f, abstracting N. S. Vul'fson, et al., "The Claisen-Schmidt reaction with heterocyclic analogs of o-hydroxyacetophenone. I. Condensation of dehydroacetic acid with benzaldehyde", *Zh. Obshshei Khim.*, 1964, 34(8), 2743-47.

N. S. Vul'fson, et al., "The Claisen-Schmidt reaction with heterocyclic analogs of o-hydroxyacetophenone. I. Condensation of dehydroacetic acid with benzaldehyde", *J. Gen. Chem. USSR*, 1964, 34(8), 2766-69.

N. S. Vul'fson, et al., "The Claisen-Schmidt reaction with heterocyclic analogs of o-hydroxyacetophenone. III. Condensation of 4-Hydroxy-2-Acetyl-6-Methylprid-2-one, and its N-Methyl and N-Phenyl Derivatives with Armoatic Aldehydes", *Chem. Heterocycl. Compd.*, 1967, 3(4), 546-48.

* cited by examiner

HETEROARYL SULFONES AND SULFONAMIDES AND THERAPEUTIC USES THEREOF

CROSS-REFERENCE TO RELATED APPLICATION

This application claims the benefit of U.S. Provisional Application Ser. No. 60/578,162, filed Jun. 8, 2004, the entire disclosure of which is incorporated herein by reference.

FIELD OF THE INVENTION

The invention relates to bicyclic heteroaryl sulfones and sulfonamides, particularly coumarins, thiochromene-2-ones and 2-quinolones, that are substituted at the 3-position by a sulfonyl or sulfamyl moiety. The invention further relates to pharmaceutical compositions containing such compounds, and to methods of treatment comprising administration of such compounds.

BACKGROUND OF THE INVENTION

A. Biological Activity of Coumarin Derivatives

Anticoagulant and antithrombotic activity of certain natural and synthetic coumarin derivatives is known. See, Murray et al., *The Natural Coumarins*, Wiley, New York, 1982. Certain coumarin derivatives are also reported as triplet sensitizers (see, Williams et al., *Polym. Eng. Sci.*, 1983, 23, 1022); anti-HIV agents (Spino et al., *Bioorg. Med. Chem. Lett.*, 1998, 8, 3475-78); lipid-lowering agents (Madhavan et al., *Bioorg. Med. Chem. Lett.*, 2003, 13, 2547-51); antioxidants (Kontogiorgis et al., *J. Enzyme Inhib. Med. Chem.*, 2003, 18, 63-69); inhibitors of lipid peroxidation and vasorelaxant agents (Hoult et al., *Gen. Pharmac.* 1996, 27, 713-22); anti-inflammatory agents (Khan et al., *Indian J. Chem.*, 1993, 32, 817); and free radical scavengers (Mora et al., *J. Biochem. Pharmacol.*, 1990, 40, 793-97). In addition, two naturally-occurring coumarins have been found to exhibit cytotoxicity across a selection of mammalian cancer cell lines (Reutrakul et al., *Planta Med.*, 2003, 69, 1048-51).

Certain coumarin-3-carboxamides have been reported as inhibitors of proteases, including α-chymotrypsin (Pochet et al., *Bioorg. Med. Chem. Lett.*, 2000, 8, 1489-501; Wouters et al., *Bioorg. Med. Chem. Lett.*, 1990, 12, 1109-12; and Mor et al., *Biochim. Biophys. Acta*, 1990, 1038, 119-24) and human leukocyte elastase (HLE) (Doucet et al., *J. Med. Chem.*, 1999, 42, 4161-71; Egan et al., *Drug Metab. Rev.*, 1990, 22, 503-29; and Nicolaides et al., *J. Heterocycl. Chem.*, 1996, 33, 967)

B. Coumarin-3-sulfonamides

Hoogenboom et al. (*J. Org. Chem.* (1975), 40(7), 880-3) disclose the compound 2-oxo-N-phenyl-2H-chromene-3-carboxamide. Ismail et al. (*Afinidad* (2002), 59, 211-15) discloses 2-oxo-N-phenyl-2H-chromene-3-carboxamide derivatives wherein the phenyl ring is substituted by acylsulfonamido. Mandour et al. (*Egyptian J. Pharm. Sci.* (1995), 36(1-6), 71-85) disclose the synthesis, antimicrobial activity and antiaflatoxigenic activity of 2-oxo-N-phenyl-2H-chromene-3-carboxamide derivatives wherein the coumarin ring system is substituted by nitro. Abd-El-Hafez et al. (*Egyptian J. Pharm. Sci.* (1994), 35(1-6), 113-26) disclose the preparation and antimicrobial activity of activity of 2-oxo-N-phenyl-2H-chromene-3-carboxamide derivatives wherein the coumarin ring system is substituted by nitro. Abd El-Aleem et al. (*Modelling, Measurement & Control, C: Energetics, Chemistry, Earth, Environmental & Biomedical Problems* (1995), 47(1), 49-54) and El-Maghraby et al. (*Egyptian Journal of Chemistry* (1985), 27(4), 459-69) disclose certain coumarin 3,6-disulfonamides. Silvio et al. (*Gazz. Chim. Ital.*, (1967), 97(12), 1749-61) disclose 2-oxo-N-phenyl-2H-chromene-3-carboxamide derivatives wherein the coumarin ring system is substituted at the 4-position by an arylamino group. Merchant et al. (*J. Org. Chem.*, (1957), 22, 884-7) disclose the compound 7-ethyl-6-methoxy-4-methyl-2-oxo-N-phenyl-2H-chromene-3-sulfonamide. Merchant et al. (*J. Indian Chem. Soc.* (1957), 34, 35-41) discloses the compound 6-nitro-2-oxo-N-phenyl-2H-chromene-3-sulfonamide and the compound 2-oxo-$N^3,N^6$-diphenyl-2H-chromene-3,6-disulfonamide.

C. Proliferative Disorders

Extracellular signals received at transmembrane receptors are relayed into the cells via signal transduction pathways (Pelech et al., *Science* 257:1335 (1992)). Such signalling has been implicated in induction of cell proliferation, differentiation or apoptosis (Davis et al., *J. Biol. Chem.* 268:14553 (1993)). One such signal transduction pathway is the mitogen activated protein kinase (MAPK) cascade. See, Nishida et al., *Trends Biochem. Sci.* 18:128 (1993) and Blumer et al., *Trends Biochem. Sci.* 19:236 (1994). Much of the MAPK pathway is conserved over different species. The most thoroughly studied of the MAPKs are extra cellular signal regulated kinases (ERKs) (Posada et al., *Science* 255:212 (1992); Biggs III et al., *PNAS. USA* 89:6295 (1992); and Garner et al., *Genes Dev.* 6:1280 (1992)) and c-Jun $NH_2$ terminal kinases (JNKs) (Hibi et al., *Genes Dev.* 7:2135 (1993)). JNKs are members of a class of stress activated protein kinases (SAPK) and are shown to be activated by treatment of cells with UV radiation, pro-inflammatory cytokines and environmental stress (Derijard et al., *Cell* 1025 (1994)). Activation of ERK has been shown to involve kinase mediated phosphorylation of threonine and tyrosine residues, which signals cell proliferation. In contrast, activation of JNKs leads to cell growth inhibition and apoptosis.

Protein tyrosine kinases are enzymes which catalyze a well defined chemical reaction: the phosphorylation of a tyrosine residue (Hunter et al., *Ann. Rev. Biochem.* 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., *Eur. J. Biochem.* 135:583-589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

Cancer and other proliferative disorders remain a major unmet medical need. Cancer treatments often comprise surgery, chemotherapeutic treatments, radiation treatment or combinations thereof. Chemotherapeutic treatments for most cancers only delay disease progression rather than providing a cure. Cancers often become refractory to chemotherapy via development of multidrug resistance. Particular cancers are inherently resistant to some classes of chemotherapeutic agents. See DeVita et al, Principles of Cancer Management: Chemotherapy. In: Cancer. Principles and Practice of Oncology, 5th edition, Lippincott-Raven, Philadelphia, New York (1977), pp. 333-347.

Although progress has been made in the range of treatment of proliferative disorders such as cancer, there remains a need to develop new therapeutic agents, particularly agents that target receptor tyrosine kinases and arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

DEFINITIONS

General

The term "individual" includes human beings and non-human animals.

The expression "effective amount" when used to describe therapy to an individual suffering from a cancer or other disorder which manifests abnormal cellular proliferation, refers to the amount of a compound according to Formula I that inhibits the growth or proliferation of tumor cells, or alternatively induces apoptosis of cancer cells, preferably tumor cells, resulting in a therapeutically useful and preferably selective cytotoxic effect on proliferative cells.

The term "proliferative disorder" means a disorder wherein cells are made by the body at an atypically accelerated rate.

Chemical

The term "alkyl", by itself, or as part of another substituent, e.g., haloalkyl or aminoalkyl, means, unless otherwise stated, a saturated hydrocarbon radical having the designated number of carbon atoms (i.e. $C_1$-$C_6$ means the group contains one, two, three, four, five or six carbons) and includes straight, branched chain, cyclic and polycyclic groups. Examples include methyl, ethyl, propyl, isopropyl, butyl, isobutyl, tert-butyl, pentyl, neopentyl, hexyl, cyclohexyl, norbornyl and cyclopropylmethyl. Preferred alkyl groups comprise —($C_1$-$C_6$)alkyl. Most preferred is —($C_1$-$C_3$)alkyl, particularly ethyl, methyl and isopropyl.

"Substituted alkyl" means alkyl, as defined above, substituted by one, two or three substituents. The substituents are preferably independently selected from the group consisting of halogen, —OH, —O($C_1$-$C_4$)alkyl, —$NH_2$, —N($CH_3$)$_2$, —$CO_2$H, —$CO_2$($C_1$-$C_4$)alkyl, —$CF_3$, —$CONH_2$, —$SO_2NH_2$, —C(=NH)$NH_2$, —CN and —$NO_2$. More preferably, the substituted alkyl contains one or two substituents independently selected from the group consisting of halogen, —OH, $NH_2$, —N($CH_3$)$_2$, trifluoromethyl and —$CO_2$H; most preferably halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical having the designated number of carbons. For example, the expression "—C(=O)($C_1$-$C_4$)alkylene-R" includes one, two, three and four carbon alkylene groups. A substitution of a group such as R on alkylene may be at any substitutable carbon. For example, the group —C(=O)($C_4$ alkylene)R, includes, for example (a), (b) and (c), in Scheme 1, below:

Scheme 1

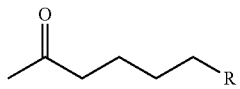

(a)

-continued

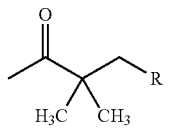

(b)

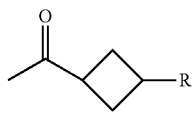

(c)

The term "amine" or "amino" refers to radicals of the general formula NRR', wherein R and R' are independently hydrogen or a hydrocarbyl radical, or wherein R and R' combined form a heterocycle. Examples of amino groups include —$NH_2$, methyl amino, diethyl amino, anilino, benzyl amino, piperidinyl, piperazinyl and indolinyl.

The term "aromatic" refers to a carbocycle or heterocycle having one or more polyunsaturated rings having aromatic character (4n+2) delocalized π (pi) electrons).

The term "aryl," employed alone or in combination with other terms, means, unless otherwise stated, a carbocyclic aromatic group containing one or more rings (typically one, two or three rings). Multiple rings may be attached together in a pendent manner, such as a biphenyl, or may be fused, such as naphthalene. Examples include phenyl, anthracyl and naphthyl. Preferred are phenyl and naphthyl, most preferred is phenyl.

The term "aryl-($C_1$-$C_3$)alkyl" means a radical wherein a one to three carbon alkylene chain is attached to an aryl group, e.g., —$CH_2CH_2$-phenyl. Preferred are aryl($CH_2$)— and aryl (CH($CH_3$))—. The term "substituted aryl-($C_1$-$C_3$)alkyl" means an aryl-($C_1$-$C_3$)alkyl radical in which the aryl group is substituted. Preferred is substituted aryl($CH_2$)—. Similarly, the term "heteroaryl($C_1$-$C_3$)alkyl" means a radical wherein a one to three carbon alkylene chain is attached to a heteroaryl group, e.g., —$CH_2CH_2$-pyridyl. Preferred is heteroaryl ($CH_2$)—. The term "substituted heteroaryl-($C_1$-$C_3$)alkyl" means a heteroaryl-($C_1$-$C_3$)alkyl radical in which the heteroaryl group is substituted. Preferred is substituted heteroaryl($CH_2$)—.

The term "arylene," by itself or as part of another substituent means, unless otherwise stated, a divalent aryl radical. Preferred are divalent phenyl radicals, particularly 1,4-divalent phenyl radicals.

The term "coumarin," by itself, or as part of a larger chemical name, means, unless otherwise stated, a bicyclic heteroaryl ring system of the Formula:

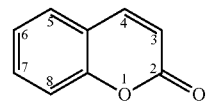

wherein the numbering of the positions in the bicyclic heteroaryl ring is as shown. Alternative naming of coumarin compounds includes nomenclature such as "2H-chromene-2-one" and "2H-benzopyran-2-one." Specific compounds herein are named as 2H-chromene-2-ones.

The term "thiochromene-2-one," by itself, or as part of a larger chemical name, as employed herein means, unless otherwise stated, a bicyclic heteroaryl ring system of the Formula:

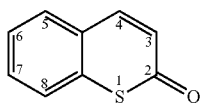

wherein the numbering of the positions in the bicyclic heteroaryl ring is as shown.

The term "2-quinolone," by itself, or as part of a larger chemical name, as employed herein means, unless otherwise stated, a bicyclic heteroaryl ring system of the Formula:

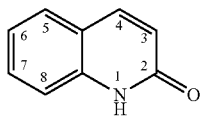

wherein the numbering of the positions in the bicyclic heteroaryl ring is as shown. The 2-quinolone exists in a plurality of tautomeric forms:

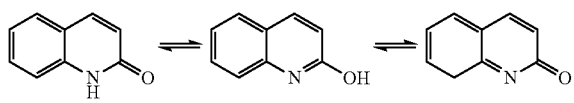

all of which are understood to be included within the term "2-quinolone."

The term "cycloalkyl" refers to ring-containing alkyl radicals. Examples include cyclohexyl, cyclopentyl, cyclopropyl methyl and norbornyl.

The term "hydrocarbyl" refers to any moiety comprising only hydrogen and carbon atoms. Preferred hydrocarbyl groups are $(C_1-C_{12})$hydrocarbyl, more preferably $(C_1-C_8)$ hydrocarbyl, most preferably benzyl and —$(C_1-C_6)$alkyl.

The term "hydrocarbylene" by itself or as part of another substituent means, unless otherwise stated, a divalent moiety comprising only hydrogen and carbon atoms. A substitution of a group —R on hydrocarbylene may be at any substitutable carbon, i.e., the expression —$(C_1-C_6$ hydrocarbylene)R includes, for example, the structures shown in Scheme 2:

Scheme 2

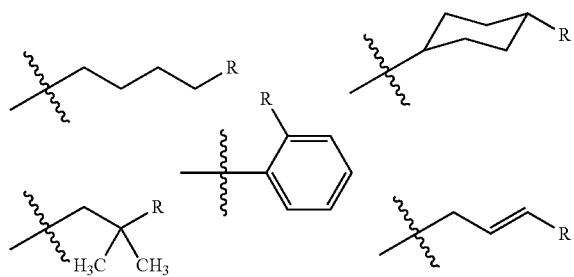

The term "heteroalkyl" by itself or in combination with another term means, unless otherwise stated, a stable straight or branched chain radical consisting of the stated number of carbon atoms and one or two heteroatoms selected from the group consisting of O, N, and S, wherein the sulfur heteroatoms may be optionally oxidized and the nitrogen heteroatoms may be optionally quaternized or oxidized. The oxygens bonded to oxidized sulfur or nitrogen may be present in addition to the one or two heteroatoms in the heteroalkyl group. The heteroatom(s) may occupy any position in the heteroalkyl group, including the attachment position of the heteroalkyl group and a terminal atom of the heteroalkyl group. Examples of heteroalkyl groups include: —S—$CH_2$—$CH_2$—$CH_3$, —$CH_2$—$CH_2CH_2$—OH, —$CH_2$—$CH_2$—NH—$CH_3$, —$CH_2$—$SO_2$—NH—$CH_3$, —$CH_2$—S—$CH_2$—$CH_3$ and —$CH_2CH_2$—S(=O)—$CH_3$. Two heteroatoms may be bonded to each other, such as, for example, —$CH_2$—NH—$OCH_3$, or —$CH_2$—$CH_2$—S—S—$CH_3$.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocycle may be attached to the compound of which it is a component, unless otherwise stated, at any heteroatom or carbon atom in the heterocycle which affords a stable structure.

The term "heteroaryl" or "heteroaromatic" refers to a heterocycle having aromatic character. A monocyclic heteroaryl group is preferably a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated.

Examples of polycyclic heteroaryl groups containing a partially saturated ring include tetrahydroquinolyl and 2,3-dihydrobenzofuryl. For compounds according to Formula I, below, the attachment point on the aromatic group $R^2$ is understood to be on an atom which is part of an aromatic monocyclic ring or a ring component of a polycyclic aromatic which is itself an aromatic ring. For example, on the partially saturated heteroaryl ring, 1,2,3,4-tetrahydroisoquinoline, attachment points are ring atoms at the 5-, 6-, 7- and 8-positions. The attachment point on aromatic group $R^2$ may be a ring carbon or a ring nitrogen and includes attachment to form aromatic quaternary ammonium salts such as pyridinium.

Examples of non-aromatic heterocycles include monocyclic groups such as: aziridinyl, oxiranyl, thiiranyl, azetidinyl, oxetanyl, thietanyl, pyrrolidinyl, pyrrolinyl, imidazolinyl, pyrazolidinyl, dioxolanyl, sulfolanyl, 2,3-dihydrofuranyl, 2,5-dihydrofuranyl, tetrahydropyranyl, thiophanyl, piperidinyl, 1,2,3,6-tetrahydropyridinyl, 1,4-dihydropyridinyl, piperazinyl, morpholinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepinyl, 4,7-dihydro-1,3-dioxepinyl and hexamethyleneoxide.

Examples of monocyclic heteroaryl groups include, for example, six-membered monocyclic aromatic rings such as, for example, pyridyl, pyrazinyl, pyrimidinyl and pyridazinyl; and five-membered monocyclic aromatic rings such as, for example, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, indolinyl, quinolyl, tetrahydroquinolyl, isoquinolyl, 1,2,3,4-tetrahydroisoquinolyl, cinnolinyl, quinoxalinyl, quinazolinyl, phthalazinyl, 1,8-naphthyridinyl, 1,4-benzodioxanyl, chromene-2-one-yl (coumarinyl), dihydrocoumarin, chromene-4-one-yl, benzofuryl, 1,5-naphthyridinyl, 2,3-dihydrobenzofuryl, 1,2-benzisoxazolyl, benzothienyl, benzoxazolyl, benzthiazolyl, purinyl, benzimidazolyl, benztriazolyl, thioxanthinyl, benzazepinyl, benzodiazepinyl, carbazolyl, carbolinyl, acridinyl, pyrrolizidinyl and quinolizidinyl.

The term "heteroarylene," by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from the group consisting of pyridine, piperazine, pyrimidine, pyrazine, furan, thiophene, pyrrole, thiazole, imidazole and oxazole.

The aforementioned listing of heterocyclyl and heteroaryl moieties is intended to be representative, not limiting.

The terms "halo" or "halogen" by themselves or as part of another substituent, e.g., "haloalkyl," mean, unless otherwise stated, a fluorine, chlorine, bromine, or iodine atom. Fluorine, chlorine and bromine are preferred. Fluorine and chlorine are most preferred.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group are possible. The halogen substituents may be the same or different. Preferred haloalkyl groups include, for example, perfluoro($C_1$-$C_6$)alkyl, trifluoro($C_1$-$C_6$)alkyl, gem-difluoro ($C_1$-$C_4$)alkyl and chloro($C_1$-$C_4$)alkyl. More preferred haloalkyl groups include, for example, —$CF_3$, —$C_2F_5$, —$CH_2CF_3$, —$CHF_2$, $CF_2CH_3$ and —$CH_2Cl$.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "gem-difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted carbon may be any carbon in the chain having at least two substitutable hydrogens, including the terminal —$CH_3$ group and the proximal carbon through which the difluoro($C_x$-$C_y$) alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted," with respect to a molecule or a chemical group, means that an atom or group of atoms has replaced hydrogen as the substituent attached to another group. For aryl and heteroaryl groups, the term "substituted" refers to any level of substitution, namely mono-, di , tri-, tetra-, or penta-substitution, where such substitution is permitted. The substituents are independently selected, and substitution may be at any chemically accessible position.

The naming of compounds disclosed herein was done by employing the structure naming programs included CHEM-DRAW ULTRA Version 8.0 (© 1985-2003, CambridgeSoft Corporation, 100 Cambridgepark Drive, Cambridge, Mass. 02140 USA). The sulfonamide compounds were named by analogy to the corresponding carboxamide structure named using CHEMDRAW.

SUMMARY OF THE INVENTION

It is an object of the invention to provide compounds, compositions and methods for the treatment of cancer and other proliferative disorders. The biologically active compounds are in the form of coumarin-3-sulfones and coumarin-3-sulfonamides, thiochromene-2-one-3-sulfones and thiochromene-2-one-3-sulfonamides, and 2-quinolone-3-sulfones and 2-quinolone-3-sulfonamides.

I. Compounds According to the Invention

According to one embodiment of the invention, novel compounds are provided according to Formula I:

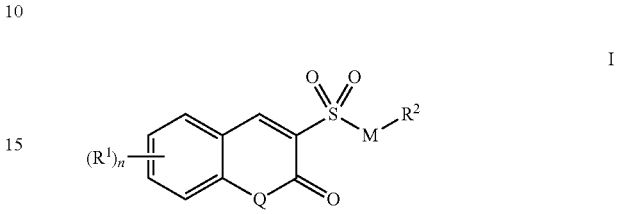

wherein:

each Q is independently O, S, or NH;

each $R^1$ is independently selected from the group consisting of halogen, —($C_1$-$C_8$)hydrocarbyl, —C(=O)$R^y$, —$NR^w{}_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^y$, —OCH($R^z$)C(=O)$R^y$, =$OSO_2R^y$, —O($C_1$-$C_4$)alkylene-$CO_2R^w$, —OP(=O)($OR^w$)$_2$, —O($C_2$-$C_6$)alkylene-N($CH_3$)$_2$, —O($C_1$-$C_6$)haloalkyl, —P(=O)($OR^w$)$_2$, —$SO_2$N($R^w$)$R^x$, —NHC(=NH)$NHR^x$, —($C_1$-$C_6$)haloalkyl and heteroalkyl;

$R^w$ is —H or —($C_1$-$C_8$)hydrocarbyl;

$R^x$ is —H, —($C_1$-$C_8$)hydrocarbyl or —C(=O)($C_1$-$C_8$) hydrocarbyl;

$R^y$ is selected from the group consisting of —H, —($C_1$-$C_8$) hydrocarbyl, —O($C_1$-$C_8$)hydrocarbyl, substituted phenyl, substituted heterocyclyl($C_1$-$C_3$)alkyl, heteroaryl($C_1$-$C_3$) alkyl, —($C_2$-$C_{10}$)heteroalkyl, —($C_1$-$C_6$)haloalkyl, —CH($R^z$)$NHR^x$, —N($R^w$)$R^x$, —($C_1$-$C_3$)alkylene$NH_2$, —($C_1$-$C_3$) alkyleneN($CH_3$)$_2$, —($C_1$-$C_3$)perfluoroalkyleneN($CH_3$)$_2$, —($C_1$-$C_3$)alkyleneN$^+$(($C_1$-$C_3$)alkyl)$_3$, —($C_1$-$C_3$)alkylene—N$^+$($CH_2CH_2OH$)$_3$, —($C_1$-$C_3$)alkylene-$OR^x$, —($C_1$-$C_4$)alkylene-$CO_2R^x$, —($C_1$-$C_4$)alkylene-$CO_2$N($R^w$)$R^x$, —($C_1$-$C_4$) alkylene-C(=O)halogen, halo($C_1$-$C_3$)alkyl and —($C_1$-$C_4$) perfluoroalkylene-$CO_2R^x$;

$R^z$ is selected from the group consisting of —H, —($C_1$-$C_6$) alkyl, —($CH_2$)$_3$—NH—C($NH_2$)(=NH), —$CH_2C$(=O) $NH_2$, —$CH_2COOH$, —$CH_2SH$, —($CH_2$)$_2$C(=O)—$NH_2$, —($CH_2$)$_2CO_2H$, —$CH_2$-(2-imidazolyl), —($CH_2$)$_4$-$NH_2$, —($CH_2$)$_2$—S—$CH_3$, phenyl, —$CH_2$-phenyl, —$CH_2$—OH, —CH(OH)—$CH_3$, —$CH_2$-(3-indolyl) and —$CH_2$-(4-hydroxyphenyl);

each n is independently selected from the group consisting of 0, 1, 2, 3 and 4; preferably 1, 2, 3 and 4; more preferably 1, 2 and 3;

M is selected from the group consisting of a single bond and (a), (b), (c), (d) and (e):

-continued

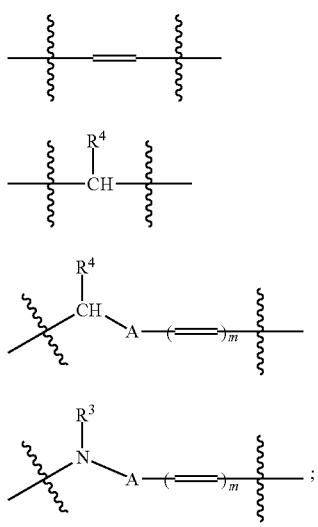

R² is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl;

R³ and R⁴ are independently selected from the group consisting of —H and —($C_1$-$C_6$)alkyl, preferably —H and —$CH_3$, more preferably —H;

m is 0 or 1; and

A is —$SO_2$— or —C(=O)—, preferably —$SO_2$—;

provided that:

(i) when Q is O and M is:

(a)

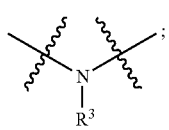

then R¹ is other than —$NO_2$ or —$SO_2NHR^w$;

(ii) when M is a single bond;

then R² is:

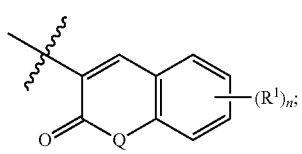

and

R¹ is other than —$NR^w{}_2$;

(iii) when m is 0;

then R² is:

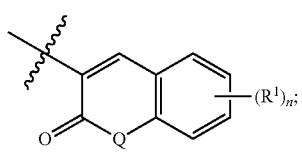

and (iv) when n is 0, then R² is other than unsubstituted phenyl;

or a salt, preferably a pharmaceutically-acceptable salt of such a compound.

According to some embodiments, Q is O. According to other embodiments, Q is S. According to still other embodiments, Q is NH. According to other embodiments, Q is independently S or O. According to still other embodiments, Q is independently O or NH.

According to some embodiments of the invention, $R^w$ is —H. According to other embodiments of the invention, $R^w$ is —($C_1$-$C_8$)hydrocarbyl.

According to some embodiments, aryl and heteroaryl groups comprising R² are substituted by 1, 2 or 3 substituents that are preferably independently selected from the group consisting of halogen, —($C_1$-$C_8$)hydrocarbyl, —C(=O)$R^y$, —$NR^w{}_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)($OR^w$)$_2$, —O($C_2$-$C_6$)alkylene-N($CH_3$)$_2$, —O($C_1$-$C_6$)haloalkyl, —P(=O)($OR^w$)$_2$, —$SO_2$N($R^w$)$R^x$, —NHC(=NH)$NHR^z$, —($C_1$-$C_6$)haloalkyl and heteroalkyl;

According to other embodiments, aryl and heteroaryl groups comprising R² are substituted by one, two or three substituents that are preferably independently selected from the group consisting of halogen, —($C_1$-$C_8$)hydrocarbyl, —C(=O)$R^y$, —$NR^w{}_2$, —NHC(=O)$R^y$, —NHCH($R^z$)C(=O)$R^y$, —NHS$O_2R^y$, —NH($C_1$-$C_4$)alkylene-$CO_2R^x$, —$NO_2$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)($OR^w$)$_2$, —O($C_2$-$C_6$)alkylene-N($CH_3$)$_2$, —O($C_1$-$C_6$)haloalkyl, —P(=O)($OR^w$)$_2$, —$SO_2NHR^x$, —NHC(=NH)$NHR^x$, —($C_1$-$C_6$)haloalkyl and heteroalkyl;

According to other embodiments, aryl and heteroaryl groups comprising R² are substituted by one, two or three substituents that are preferably independently selected from the group consisting of fluorine, chlorine, bromine, —($C_1$-$C_8$)hydrocarbyl, —C(=O)$R^y$, —$NR^w{}_2$, —NHC(=O)$R^y$, —NHCH($R^z$)C(=O)$R^y$, —OCH($R^z$)C(=O)$R^y$, —OC(=O)$R^y$, —NH($C_1$-$C_4$)alkylene-$CO_2R^x$, —$NO_2$, —CN, —$OR^w$, —O($C_2$-$C_6$)alkylene-N($CH_3$)$_2$, —$CF_3$ and —$OCF_3$.

According to still other embodiments, aryl and heteroaryl groups comprising R² are substituted by one, two or three substituents that are preferably independently selected from the group consisting of fluorine, chlorine, bromine, —($C_1$-$C_8$)hydrocarbyl, —C(=O)$R^y$, —$NH_2$, —OC(=O)$R^y$ and —$OR^w$.

According to still other embodiments, aryl and heteroaryl groups comprising R² are substituted by one, two or three substituents that are —$OR^w$.

According to some embodiments, substituents on phenyl or six-membered heteroaryl R² groups are at the 2-, 4- and 6-positions of the ring. According to other embodiments, substituents on phenyl or six-membered heteroaryl R² groups are at the 2- and 4-positions of the ring. According to still other embodiments, substituents on phenyl or six-membered heteroaryl R² groups are at the 2- and 6-positions of the ring. According to still other embodiments, a single substituent on a phenyl or six-membered heteroaryl R² group is at the 2- or 4-position of the ring.

Substituents on substituted phenyl $R^y$ are preferably selected from the group consisting of —$NH_2$, —$NO_2$, N-methylpiperazinyl and —$OR^x$.

Substituents on substituted heterocyclyl($C_1$-$C_3$)alkyl groups $R^y$ are preferably —($C_1$-$C_7$)hydrocarbyl or —C(=O)($C_1$-$C_2$)hydrocarbyl, more preferably —($C_1$-$C_8$)alkyl or —C(=O) ($C_1$-$C_6$)alkyl.

According to some embodiments of the invention, each $R^1$ is independently selected from the group consisting of halogen, —$(C_1$-$C_8)$hydrocarbyl, —C(=O)$R^y$, —N$R^w{}_2$, —N($R^w$)C(=O)$R^y$, —N($R^w$)CH($R^z$)C(=O)$R^y$, —N($R^w$)SO$_2R^y$, —N($R^w$)SO$_2R^y$, —N($R^w$)(C$_1$-C$_4$)alkylene-CO$_2R^w$, —CN, —O$R^w$, —OC(=O)$R^y$, —OCH($R^z$)C(=O)$R^y$, =OSO$_2R^y$, —O(C$_1$-C$_4$)alkylene-CO$_2R^w$, —OP(=O)(O$R^w$)$_2$, —O(C$_2$-C$_6$)alkylene-N(CH$_3$)$_2$, —O(C$_1$-C$_6$)haloalkyl, —P(=O)(O$R^w$)$_2$, —NHC(=NH)NH$R^x$, —(C$_1$-C$_6$)haloalkyl and heteroalkyl;

According to other embodiments of the invention, each $R^1$ is independently selected from the group consisting of halogen, —(C$_1$-C$_8$)hydrocarbyl other than —(C$_1$-C$_6$)alkyl, —C(=O)$R^y$, —NH$R^w$, —NHC(=O)$R^y$, —N($R^w$)CH($R^z$)C(=O)$R^y$, —N($R^w$)SO$_2R^y$, —NHSO$_2R^y$, —NH(C$_1$-C$_4$)alkylene-CO$_2R^x$, —CN, —O$R^w$, —OCH($R^z$)C(=O)$R^y$, —OC(=O)$R^y$, —O(C$_1$-C$_6$)haloalkyl, —P(=O)(O$R^w$)$_2$, —OP(=O)(O$R^w$)$_2$, —O(C$_2$-C$_6$)alkylene-N(CH$_3$)$_2$, —NHC(=NH)NH$R^x$, —(C$_1$-C$_6$)haloalkyl and heteroalkyl.

According to still other embodiments of the invention, each $R^1$ is independently selected from the group consisting of fluoro, chloro, bromo, —(C$_1$-C$_8$)hydrocarbyl, —C(=O)$R^y$, —NH$R^w$, —NHC(=O)$R^y$, —NHCH($R^z$)C(=O)$R^y$, —NH(C$_1$-C$_4$)alkylene-CO$_2R^x$, —CN, —O$R^w$, —OC($R^z$)C(=O)$R^y$, —OC(=O)$R^y$, —O(C$_1$-C$_6$)haloalkyl, —O(C$_2$-C$_6$)alkylene-N(CH$_3$)$_2$, —OP(=O)(O$R^w$)$_2$ and —(C$_1$-C$_6$)haloalkyl.

According to still other embodiments, each $R^1$ is independently selected from the group consisting of fluoro, chloro and bromo, —(C$_1$-C$_6$)alkyl, —C(=O)$R^y$, —NHC(=O)$R^y$, —NHSO$_2R^y$, —CN, —OC(=O)$R^y$, —O(C$_1$-C$_6$)alkyl, —OP(=O)(O$R^w$)$_2$ and —(C$_1$-C$_6$)haloalkyl.

It is to be understood that two —(C$_1$-C$_8$)hydrocarbyl $R^1$ substituents on adjacent carbon atoms of a compound of Formula I (i.e., at positions 5 and 6, at positions 6 and 7, or at positions 7 and 8) may combine to form an aryl ring. One example of such a compound is [(2-oxobenzo[g]chromen-3-yl)sulfonyl]-benzo[g]chromen-2-one.

According to some embodiments, $R^y$ is selected from the group consisting of —H, —(C$_1$-C$_8$)hydrocarbyl, —O(C$_1$-C$_8$) hydrocarbyl, substituted phenyl, substituted heterocyclyl(C$_1$-C$_3$)alkyl, heteroaryl(C$_1$-C$_3$)alkyl, —(C$_2$-C$_{10}$)heteroalkyl, —(C$_1$-C$_6$)haloalkyl, —C($R^z$)NH$R^x$, —N($R^w$)$R^x$, —(C$_1$-C$_3$)alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$-C$_3$)alkylene-O$R^x$, —(C$_1$-C$_4$)alkylene-CO$_2R^x$, —(C$_1$-C$_4$)alkylene-CO$_2$N($R^w$)$R^x$, halo(C$_1$-C$_3$)alkyl and —(C$_1$-C$_4$)perfluoroalkylene-CO$_2R^x$.

According to other embodiments, $R^y$ is selected from the group consisting of —H, —(C$_1$-C$_6$)alkyl, substituted phenyl, substituted heterocyclyl(C$_1$-C$_3$)alkyl, heteroaryl(C$_1$-C$_3$)alkyl, —(C$_2$-C$_6$)heteroalkyl, —(C$_1$-C$_6$)haloalkyl, —C($R^z$)NH$R^x$, —NH$R^x$, —(C$_1$-C$_3$)alkyleneNH$_2$, —(C$_1$-C$_3$)alkyleneN(CH$_3$)$_2$, —(C$_1$-C$_3$)perfluoroalkyleneN(CH$_3$)$_2$, —(C$_1$-C$_3$)alkylene-O$R^x$, —(C$_1$-C$_4$)alkylene-CO$_2R^x$, —(C$_1$-C$_4$)alkylene-CO$_2$NH$R^x$, halo(C$_1$-C$_3$)alkyl and —(C$_1$-C$_4$)perfluoroalkylene-CO$_2R^x$.

According to still other embodiments, $R^y$ is selected from the group consisting of —H, —(C$_1$-C$_6$)alkyl, —O(C$_1$-C$_6$) alkyl, substituted phenyl, substituted heterocyclyl(C$_1$-C$_3$) alkyl, heteroaryl(C$_1$-C$_3$)alkyl, —(C$_1$-C$_6$)haloalkyl, —C($R^z$)NH$R^x$, —NH$R^x$, —(C$_1$-C$_3$)alkyleneNH$_2$, —(C$_1$-C$_3$)alkyleneN(CH$_3$)$_2$, —(C$_1$-C$_3$)alkylene-O$R^x$, —(C$_1$-C$_4$)alkylene-CO$_2R^x$, —(C$_1$-C$_4$)alkylene-CO$_2$NH$R^x$ and halo(C$_1$-C$_3$)alkyl.

According to some embodiments of compounds according to Formula I, the carbon-carbon double bond, which may be a structural feature of M when M is (b), (d) or (e), is in the E-conformation. According to other embodiments of compounds according to Formula I, the carbon-carbon double bond, which may be a structural feature of M when M is (b), (d) or (e), is in the Z-conformation.

A. Compounds According to Formula IA

According to a first sub-embodiment of the compounds of the invention, there is provided a compound according to Formula IA:

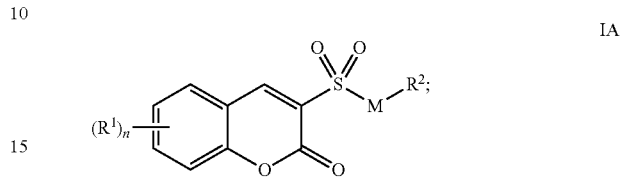

IA wherein $R^1$, $R^2$, $R^w$, $R^x$, $R^y$, $R^z$, $R^3$, $R^4$, M, A and n are as defined herein for compounds of Formula I.

According to a first embodiment of compounds of Formula IA, there is provided a compound wherein M is (a):

(a)

and each $R^1$ is independently selected from the group consisting of halogen, —(C$_1$-C$_8$)hydrocarbyl, —C(=O)$R^y$, —N$R^w{}_2$, —N($R^w$)C(=O)$R^y$, —N($R^w$)CH($R^z$)C(=O)$R^y$, —N($R^w$)SO$_2R^y$, —N($R^w$)(C$_1$-C$_4$)alkylene-CO$_2R^w$, —CN, —O$R^w$, —OC(=O)$R^y$, —OCH($R^z$)C(=O)$R^y$, —OSO$_2R^y$, —O(C$_1$-C$_4$)alkylene-CO$_2R^w$, —OP(=O)(O$R^w$)$_2$, —O(C$_2$-C$_6$)alkylene-N(CH$_3$)$_2$, —O(C$_1$-C$_6$)haloalkyl, —P(=O)(O$R^w$)$_2$, —NHC(=NH)NH$R^x$, —(C$_1$-C$_6$)haloalkyl and heteroalkyl;

or a salt of such a compound

Preferred compounds according to the first embodiment of compounds according to Formula IA include:
6-bromo-N-(4-methoxyphenyl)-2-oxo-2H-chromene-3-sulfonamide; 6-chloro-N-(4-methoxyphenyl)-2-oxo-2H-chromene-3-sulfonamide; 8-ethoxy-N-(4-methoxyphenyl)-2-oxo-2H-chromene-3-sulfonamide; 6-chloro-N-(3-hydroxy-4-methoxyphenyl)-2-oxo-2H-chromene-3-sulfonamide; N-(3-amino-4-fluorophenyl)-8-ethoxy-2-oxo-2H-chromene-3-sulfonamide; N-(3-amino-4-fluorophenyl)-6-methoxy-2-oxo-2H-chromene-3-sulfonamide; N-(4-bromophenyl)-6-methoxy-2-oxo-2H-chromene-3-sulfonamide; 8-ethoxy-N-(4-methoxyphenyl)-2-oxo-2H-chromene-3-sulfonamide; N-(4-bromophenyl)-8-chloro-2-oxo-2H-chromene-3-sulfonamide; N-(4-bromophenyl)-8-bromo-2-oxo-2H-chromene-3- sulfonamide; mixtures thereof; and salts thereof.

According to a second embodiment of compounds of Formula IA, there is provided a compound wherein M is (b):

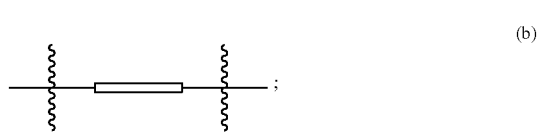

(b)

or a salt of such a compound.

Preferred compounds according to the second embodiment of compounds according to Formula IA include:

3-(E)-(4-methoxystyrylsulfonyl)-6-bromo-2H-chromen-2-one; 3-(E)-(4-chloro-styrylsulfonyl)-6-bromo-2H-chromen-2-one; 3-(E)-(2,4-dichlorostyrylsulfonyl)-6-bromo-2H-chromen-2-one; 3-(E)-(4-methoxystyrylsulfonyl)-6-chloro-2H-chromen-2-one; 3-(E)-(4-chlorostyrylsulfonyl)-6-chloro-2H-chromen-2-one; 3-(E)-(2,4-dichlorostyrylsulfonyl)-6-chloro-2H-chromen-2-one; 3-(E)-(4-methoxystyrylsulfonyl)-5,7-dimethoxy-2H-chromen-2-one; 3-(E)-(4-chlorostyrylsulfonyl)-5,7-dimethoxy-2H-chromen-2-one; 3-(E)-(2,4-dichlorostyrylsulfonyl)-5,7-dimethoxy-2H-chromen-2-one; 3-(E)-(4-methoxystyrylsulfonyl)-7-methoxy-2H-chromen-2-one; 3-(E)-(4-chlorostyrylsulfonyl)-7-methoxy-2H-chromen-2-one; 3-(E)-(2,4-dichlorostyrylsulfonyl)-7-methoxy-2H-chromen-2-one; 3-(Z)-(4-methoxystyrylsulfonyl)-6-bromo-2H-chromen-2-one; 3-(Z)-(4-chlorostyrylsulfonyl)-6-bromo-2H-chromen-2-one; 3-(Z)-(2,4-dichlorostyrylsulfonyl)-6-bromo-2H-chromen-2-one; 3-(Z)-(4-methoxystyrylsulfonyl)-6-chloro-2H-chromen-2-one; 3-(Z)-(4-chlorostyrylsulfonyl)-6-chloro-2H-chromen-2-one; 3-(Z)-(2,4-dichlorostyrylsulfonyl)-6-chloro-2H-chromen-2-one; 3-(Z)-(4-methoxystyrylsulfonyl)-5,7-dimethoxy-2H-chromen-2-one; 3-(Z)-(4-chlorostyrylsulfonyl)-5,7-dimethoxy-2H-chromen-2-one; 3-(Z)-(2,4-dichlorostyrylsulfonyl)-5,7-dimethoxy-2H-chromen-2-one; 3-(Z)-(4-methoxystyrylsulfonyl)-7-methoxy-2H-chromen-2-one; 3-(Z)-(4-chlorostyrylsulfonyl)-7-methoxy-2H-chromen-2-one; 3-(Z)-(2,4-dichlorostyrylsulfonyl)-7-methoxy-2H-chromen-2-one; mixtures thereof; and salts thereof.

According to a third embodiment of compounds of Formula IA, there is provided a compound wherein M is (c):

or a salt of such a compound.

Preferred compounds according to the third embodiment of compounds according to Formula IA include:

3-(4-methoxybenzylsulfonyl)-2H-chromen-2-one; 3-(4-methoxybenzylsulfonyl)-5,7-dimethoxy-2H-chromen-2-one; 3-(4-methoxybenzylsulfonyl)-6,8-dinitro-2H-chromen-2-one; 3-(4-chlorobenzylsulfonyl)-2H-chromen-2-one; 3-(2,4-dichlorobenzylsulfonyl)-2H-chromen-2-one; 3-(4-methoxybenzylsulfonyl)-6-bromo-2H-chromen-2-one; 3-(4-methoxybenzylsulfonyl)-6-chloro-2H-chromen-2-one; 3-(4-methoxybenzylsulfonyl)-7-methoxy-2H-chromen-2-one; 3-(4-methoxybenzylsulfonyl)-7-hydroxy-2H-chromen-2-one; 3-(4-methoxy-3-nitrobenzylsulfonyl)-5,7-dimethoxy-2H-chromen-2-one; 3-(4-methoxy-3-nitrobenzylsulfonyl)-7-methoxy-2H-chromen-2-one; 3-(4-methoxy-3-nitrobenzylsulfonyl)-7-hydroxy-2H-chromen-2-one; 3-(4-chloro-3-nitrobenzylsulfonyl)-6-chloro-2H-chromen-2-one; 3-(4-chloro-3-aminobenzylsulfonyl)-6-chloro-2H-chromen-2-one; mixtures thereof; and salts thereof.

According to a fourth embodiment of compounds of Formula IA, there is provided a compound wherein M is a single bond;
each $R^1$ is independently selected from the group consisting of halogen, —$(C_1$-$C_8)$hydrocarbyl, —C(=O)$R^y$, —N($R^w$)C(=O)$R^y$, —N($R^w$)CH($R^z$)C(=O)$R^y$, —N($R^w$)SO$_2R^y$, —N($R^w$)(C$_1$-C$_4$)alkylene-CO$_2R^w$, —NO$_2$, —CN, —O$R^w$, —OC(=O)$R^y$, —OCH($R^z$)C(=O)$R^y$, =OSO$_2R^y$, —O(C$_1$-C$_4$)alkylene-CO$_2R^w$, —OP(=O)(O$R^w$)$_2$, —O(C$_2$-C$_6$)alkylene-N(CH$_3$)$_2$, —O(C$_1$-C$_6$)haloalkyl, —P(=O)(O$R^w$)$_2$, —SO$_2$N($R^w$)$R^x$, —NHC(=NH)NH$R^x$, —(C$_1$-C$_6$)haloalkyl and heteroalkyl; and $R^2$ is:

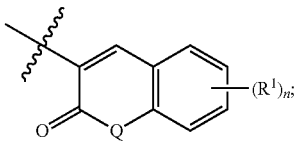

or a salt of such a compound.

According to some preferred embodiments of compounds according to the fourth embodiment of compounds according to Formula IA, $R^2$ is:

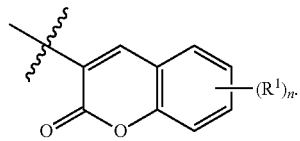

Preferred compounds according to the fourth embodiment of compounds according to Formula IA include:

6-bromo-3-[(6-bromo-2-oxochromen-3-yl)sulfonyl]chromen-2-one; 6-chloro-3-[(6-chloro-2-oxochromen-3-yl)sulfonyl]chromen-2-one; [(2-oxochromen-3-yl)sulfonyl]chromen-2-one (or bis-(2H-chromene-2-one-3-yl)-sulfone); [(2-oxochromen-3-yl)sulfonyl]quinolin-2-one; [(2-oxochromen-3-yl)sulfonyl]thiochromen-2-one; 8-ethoxy-3-[(8-ethoxy-2-oxochromen-3-yl)-sulfonyl]chromen-2-one; 3-[(5,7-dimethoxy-2-oxochromen-3-yl)sulfonyl]-5,7-dimethoxychromen-2-one; 7-methoxy-3-[(7-methoxy-2-oxochromen-3-yl)sulfonyl]chromen-2-one; 5-methoxy-3-[(5-methoxy-2-oxochromen-3-yl)sulfonyl]chromen-2-one; 6-fluoro-3-[(6-fluoro-2-oxochromen-3-yl)sulfonyl]chromen-2-one; 6-iodo-3[(6-iodo-2-oxochromen-3-yl)sulfonyl]chromen-2-one; 6-nitro-3-[(6-nitro-2-oxochromen-3-yl)sulfonyl]chromen-2-one; 8-methoxy-3-[(8-methoxy-6-nitro-2-oxochromen-3-yl)sulfonyl]-6-nitrochromen-2-one; 7-hydroxy-3-[(7-hydroxy-2-oxochromen-3-yl)sulfonyl]chromen-2-one; 6,8-dinitro-3-[(6,8-dinitro-2-oxochromen-3-yl)sulfonyl]chromen-2-one; 6-methoxy-3-[(6-methoxy-2-oxochromen-3-yl)sulfonyl]chromen-2-one; 8-methyl-3-[(8-methyl-2-oxochromen-3-yl)sulfonyl]chromen-2-one; 5-methyl-3-[(5-methyl-2-oxochromen-3-yl)sulfonyl]chromen-2-one; [(2-oxobenzo[g]chromen-3-yl)sulfonyl]benzo[g]chromen-2-one; 6-trifluoromethoxy-3-[(6-trifluoromethoxy-2-oxochromen-3-yl)sulfonyl]chromen-2-one; 6,8-dichloro-3-[(6,8-dichloro-2-oxochromen-3-yl)sulfonyl]chromen-2-one; 6,8-dibromo-3-[(6,8-bromo-2-oxochromen-3-yl)sulfonyl]chromen-2-one; 6,8-fluoro-3-[(6,8-fluoro-2-oxochromen-3-yl)sulfonyl]chromen-2-one; 5-bromo-8-methoxy-3-[(5-bromo-8-methoxy-2-oxochromen-3-yl)sulfonyl]chromen-2-one; 6-bromo-8-methoxy-3-[(6-bromo-8-methoxy-2-oxochromen-3-yl)sulfonyl]chromen-2-one; 6-chloro-8-bromo-3-[(6-chloro-8-bromo-2-oxochromen-3-yl)sulfonyl]chromen-2-one; 8-hydroxy-3-[(8-hydroxy-2-oxochromen-3-yl)sulfonyl]chromen-2-one; 6-hydroxy-3-[(6-hydroxy-2-oxochromen-3-yl)sulfonyl]chromen-2-one; 6-amino-3-[(6-amino-2-oxochromen-3-yl)sulfonyl]chromen-2-one; mixtures thereof; and salts thereof.

According to a fifth embodiment of compounds of Formula IA, there is provided a compound wherein M is (d) or (e):

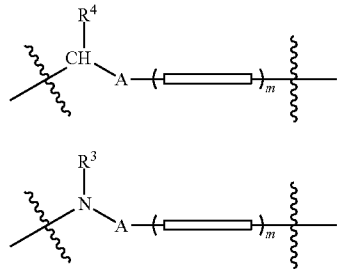

or a salt of such a compound.

According to some sub-embodiments of the fifth embodiment of compounds according to Formula IA, m is 0 and $R^2$ is:

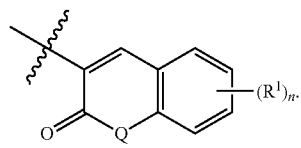

According to some preferred embodiments of compounds according to the fifth embodiment of compounds according to Formula IA, $R^2$ is:

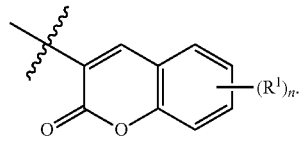

According to other sub-embodiments of the fifth embodiment of compounds according to Formula IA, m is 1, and $R^2$ is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl Preferred compounds according to the fifth embodiment of compounds according to Formula IA include:

6-chloro-3-({[(6-chloro-2-oxochromen-3-yl)sulfonyl]methyl}sulfonyl)chromen-2-one; 6-bromo-3-({[(6-bromo-2-oxochromen-3-yl)sulfonyl]methyl}sulfonyl)chromen-2-one; 6-iodo-3-({[(6-iodo-2-oxochromen-3-yl)sulfonyl]methyl}sulfonyl)chromen-2-one; 8-ethoxy-3-({[(8-ethoxy-2-oxochromen-3-yl)sulfonyl]methyl} sulfonyl)chromen-2-one; 3-({[(5,7-dimethoxy-2-oxochromen-3-yl)sulfonyl]methyl}sulfonyl)-5,7-dimethoxychromen-2-one; 7-methoxy-3-({[(7-methoxy-2-oxochromen-3-yl)sulfonyl]methyl}sulfonyl)chromen-2-one; 5-methoxy-3-({[(5-methoxy-2-oxochromen-3-yl)sulfonyl]methyl}sulfonyl)-chromen-2-one; 7-hydroxy-3-({[(7-hydroxy-2-oxochromen-3-yl)sulfonyl]-methyl }sulfonyl)-chromen-2-one; 3-({[(6,8-dinitro-2-oxochromen-3-yl)sulfonyl]methyl}-sulfonyl)-6,8-dinitro-chromen-2-one; 3-(E)-((4-methoxystyrylsulfonyl) methylsulfonyl)-7-chloro-2H-chromen-2-one; 3-(E)-((4-methoxystyrylsulfonyl)methylsulfonyl)-6-chloro-2H-chromen-2-one; 3-(E)-((4-methoxystyrylsulfonyl)methylsulfonyl)-6-bromo-2H-chromen-2-one; 3-(E)-((4-methoxystyrylsulfonyl)methylsulfonyl)-7-iodo-2H-chromen-2-one; 3-(E)-((4-methoxystyrylsulfonyl)methylsulfonyl)-8-ethoxy-2H-chromen-2-one; 3-(E)-((4-methoxystyrylsulfonyl)methylsulfonyl)-7-methoxy-2H-chromen-2-one; 3-(E)-((4-methoxystyrylsulfonyl)methylsulfonyl)-5-methoxy-2H-chromen-2-one; 3-(E)-((4-methoxystyrylsulfonyl)methylsulfonyl)-5,7-dimethoxy-2H-chromen-2-one; 3-(Z)-((4-methoxystyrylsulfonyl)methylsulfonyl)-7-chloro-2H-chromen-2-one; 3-(Z)-((4-methoxy-styrylsulfonyl)methylsulfonyl)-6-chloro-2H-chromen-2-one; 3-(Z)-((4-methoxystyryl-sulfonyl)methylsulfonyl)-6-bromo-2H-chromen-2-one; 3-(Z)-((4-methoxystyrylsulfonyl)-methylsulfonyl)-7-iodo-2H-chrome-2-one; 3-(Z)-((4-methoxystyrylsulfonyl)methyl-sulfonyl)-8-ethoxy-2H-chromen-2-one; 3-(Z)-((4-methoxystyrylsulfonyl) methylsulfonyl)-7-methoxy-2H-chromen-2-one; 3-(Z)-((4-methoxystyrylsulfonyl)methylsulfonyl)-5-methoxy-2H-chromen-2-one; 3-(Z)-((4-methoxystyrylsulfonyl) methylsulfonyl)-5,7-dimethoxy-2H-chromen-2-one; 3-((E)-4-(4-methoxyphenyl)-2-oxobut-3-enylsulfonyl)-7-chloro-2H-chromen-2-one, 3-((E)-4-(4-methoxyphenyl)-2-oxobut-3-enylsulfonyl)-6-chloro-2H-chromen-2-one; 3-((E)-4-(4-methoxyphenyl)-2-oxobut-3-enylsulfonyl)-6-bromo-2H-chromen-2-one; 3-((E)-4-(4-methoxyphenyl)-2-oxobut-3-enylsulfonyl)-6-iodo-2H-chromen-2-one; 3-((E)-4-(4-methoxyphenyl)-2-oxobut-3-enylsulfonyl)-8-ethoxy-2H-chromen-2-one; 3-((E)-4-(4-methoxyphenyl)-2-oxobut-3-enylsulfonyl)-7-methoxy-2H-chromen-2-one; 3-((E)-4-(4-methoxyphenyl)-2-oxobut-3-enylsulfonyl)-5-methoxy-2H-chromen-2-one; 3-((E)-4-(4-methoxyphenyl)-2-oxobut-3-enylsulfonyl)-5,7-dimethoxy-2H-chromen-2-one; 3-((Z)-4-(4-methoxyphenyl)-2-oxobut-3-enylsulfonyl)-7-chloro-2H-chromen-2-one, 3-((Z)-4-(4-methoxyphenyl)-2-oxobut-3-enylsulfonyl)-6-chloro-2H-chromen-2-one; 3-((Z)-4-(4-methoxyphenyl)-2-oxobut-3-enylsulfonyl)-6-bromo-2H-chromen-2-one; 3-((Z)-4-(4-methoxyphenyl)-2-oxobut-3-enylsulfonyl)-6-iodo-2H-chromen-2-one; 3-((Z)-4-(4-methoxyphenyl)-2-oxobut-3-enylsulfonyl)-8-ethoxy-2H-chromen-2-one; 3-((Z)-4-(4-methoxyphenyl)-2-oxobut-3-enylsulfonyl)-7-methoxy-2H-chromen-2-one; 3-((Z)-4-(4-methoxyphenyl)-2-oxobut-3-enylsulfonyl)-5-methoxy-2H-chromen-2-one; 3-((Z)-4-(4-methoxyphenyl)-2-oxobut-3-enylsulfonyl)-5,7-dimethoxy-2H-chromen-2-one; mixtures thereof; and salts thereof.

B. Compounds According to Formula IB

According to a second sub-embodiment of the compounds of the invention, there is provided a compound according to Formula IB:

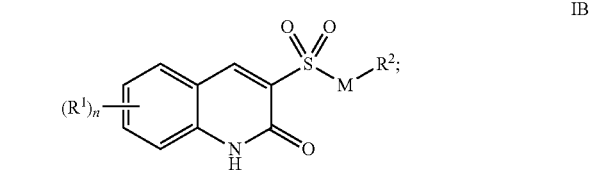

wherein $R^1$, $R^2$, $R^w$, $R^x$, $R^y$, $R^z$, $R^3$, $R^4$, M, A and n are as defined herein for compounds of Formula I.

According to a first embodiment of compounds of Formula IB, there is provided a compound wherein M is (a):

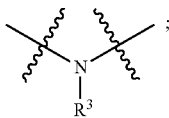

and each R¹ is independently selected from the group consisting of halogen, —(C₁-C₈)hydrocarbyl, —C(=O)Rʸ, —NRʷ₂, —N(Rʷ)C(=O)Rʸ, —N(Rʷ)CH(Rᶻ)C(=O)Rʸ, —N(Rʷ)SO₂Rʸ, —N(Rʷ)(C₁-C₄)alkylene-CO₂Rʷ, —CN, —ORʷ, —OC(=O)Rʸ, —OCH(Rᶻ)C(=O)Rʸ, —OSO₂Rʸ, —O(C₁-C₄)alkylene-CO₂Rʷ, —OP(=O)(ORʷ)₂, —O(C₂-C₆)alkylene-N(CH₃)₂, —O(C₁-C₆)haloalkyl, —P(=O)(ORʷ)₂, —NHC(=NH)NHRˣ, —(C₁-C₆)haloalkyl and heteroalkyl.

Preferred compounds according to the first embodiment of compounds according to Formula IB include:
1,2-dihydro-N-(4-methoxyphenyl)-2-oxoquinoline-3-sulfonamide; 7-chloro-1,2-dihydro-N-(4-methoxyphenyl)-2-oxoquinoline-3-sulfonamide; 5,7-dibromo-1,2-dihydro-N-(4-methoxyphenyl)-2-oxoquinoline-3-sulfonamide; 1,2-dihydro-N-((3-hydroxy-4-methoxyphenyl)-2-oxoquinoline-3-sulfonamide; 7-chloro-1,2-dihydro-N-((3-hydroxy-4-methoxyphenyl)-2-oxoquinoline-3-sulfonamide; 5,7-dibromo-1,2-dihydro-N-((3-hydroxy-4-methoxyphenyl)-2-oxoquinoline-3-sulfonamide; 1,2-dihydro-N-(3-amino-4-fluorophenyl)-2-oxoquinoline-3-sulfonamide; 7-chloro-1,2-dihydro-N-(3-amino-4-fluorophenyl)-2-oxoquinoline-3-sulfonamide; 5,7-dibromo-1,2-dihydro-N-(3-amino-4-fluorophenyl)-2-oxoquinoline-3-carboxamide; 1,2-dihydro-N-(4-bromophenyl)-2-oxoquinoline-3-sulfonamide; 7-chloro-1,2-dihydro-N-(4-bromophenyl)-2-oxoquinoline-3-sulfonxamide; 5,7-dibromo-1,2-dihydro-N-(4-bromophenyl)-2-oxoquinoline-3-sulfonamide; mixtures thereof; and salts thereof.

According to a second embodiment of compounds of Formula IB, there is provided a compound wherein M is (b):

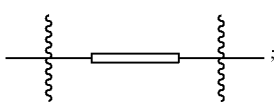

or a salt of such a compound.

Preferred compounds according to the second embodiment of compounds according to Formula IB include:
7-chloro-3-(E)-(4-methoxystyrylsulfonyl)quinolin-2(1H)-one; 3-(E)-(4-methoxystyrylsulfonyl)quinolin-2(1H)-one; 5,7-dibromo-3-(E)-(4-methoxystyrylsulfonyl)quinolin-2(1H)-one; 7-chloro-3-(E)-(4-chlorostyrylsulfonyl)-quinolin-2(1H)-one; 3-(E)-(4-chlorostyrylsulfonyl)quinolin-2(1H)-one; 5,7-dibromo-3-(E)-(4-chlorostyrylsulfonyl)-quinolin-2(1H)-one; 7-chloro-3-(E)-(2,4-dichlorostyrylsulfonyl)quinolin-2(1H)-one; 3-(E)-(2,4-dichlorostyrylsulfonyl)quinolin-2(1H)-one; 5,7-dibromo-3-(E)-(2,4-dichlorostyrylsulfonyl)quinolin-2(1H)-one; 7-chloro-3-(Z)-(4-methoxystyrylsulfonyl)-quinolin-2(1H)-one; 3-(Z)-(4-methoxystyrylsulfonyl)quinolin-2(1H)-one; 5,7-dibromo-3-(Z)-(4-methoxystyrylsulfonyl)quinolin-2(1H)-one; 7-chloro-3-(Z)-(4-chlorostyrylsulfonyl)quinolin-2(1H)-one; 3-(Z)-(4-chlorostyrylsulfonyl)quinolin-2(1H)-one; 5,7-dibromo-3-(Z)-(4-chlorostyrylsulfonyl)quinolin-2(1H)-one; 7-chloro-3-(Z)-(2,4-dichlorostyrylsulfonyl)quinolin-2(1H)-one; 3-(Z)-(2,4-dichlorostyrylsulfonyl)quinolin-2(1H)-one; 5,7-dibromo-3-(Z)-(2,4-dichlorostyrylsulfonyl)quinolin-2(1H)-one; mixtures thereof; and salts thereof.

According to a third embodiment of compounds of Formula IB, there is provided a compound wherein M is (c):

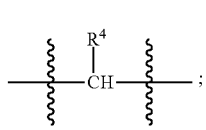

or a salt of such a compound.

Preferred compounds according to the third embodiment of compounds according to Formula IB include:
3-(4-methoxybenzylsulfonyl)-7-chloroquinolin-2(1H)-one; 3-(4-methoxybenzyl-sulfonyl)quinolin-2(1H)-one; 3-(4-methoxybenzylsulfonyl)-5,7-dibromoquinolin-2(1H)-one; 3-(4-chlorobenzylsulfonyl)-7-chloroquinolin-2(1H)-one; 3-(4-chlorobenzyl-sulfonyl)quinolin-2(1H)-one; 3-(4-chlorobenzylsulfonyl)-5,7-dibromoquinolin-2(1H)-one; 3-(2,4-dichlorobenzylsulfonyl)-7-chloroquinolin-2(1H)-one; 3-(2,4-dichlorobenzyl-sulfonyl)quinolin-2(1H)-one; 3-(2,4-dichlorobenzylsulfonyl)-5,7-dibromoquinolin-2(1H)-one; 3-(4-methoxy-3-nitrobenzysulfonyl)-7-chloroquinolin-2(1H)-one; 3-(4-methoxy-3-nitrobenzylsulfonyl)quinolin-2(1H)-one; 3-(4-methoxy-3-nitrobenzylsulfonyl)-5,7-dibromoquinolin-2(1H)-one; 3-(4-chloro-3-nitrobenzylsulfonyl)-7-chloroquinolin-2(1H)-one; 3-(4-chloro-3-nitrobenzylsulfonyl)quinolin-2(1H)-one; 3-(4-chloro-3-nitrobenzylsulfonyl)-5,7-dibromoquinolin-2(1H)-one; 3-(4-chloro-3-aminobenzyl-sulfonyl)-7-chloroquinolin-2(1H)-one; 3-(4-chloro-3-aminobenzylsulfonyl)quinolin-2(1H)-one; 3-(4-chloro-3-aminobenzylsulfonyl)-5,7-dibromoquinolin-2(1H)-one; mixtures thereof; and salts thereof.

According to a fourth embodiment of compounds of Formula IB, there is provided a compound wherein:
M is a single bond;
each R¹ is independently selected from the group consisting of halogen, —(C₁-C₈)hydrocarbyl, —C(=O)Rʸ, —N(Rʷ)C(=O)Rʸ, —N(Rʷ)CH(Rᶻ)C(=O)Rʸ, —N(Rʷ)SO₂Rʸ, —N(Rʷ)(C₁-C₄)alkylene-CO₂Rʷ, —NO₂, —CN, —ORʷ, —OC(=O)Rʸ, —OCH(Rᶻ)C(=O)Rʸ, —OSO₂Rʸ, —O(C₁-C₄)alkylene-CO₂Rʷ, —OP(=O)(ORʷ)₂, —O(C₂-C₆)alkylene-N(CH₃)₂, —O(C₁-C₆)haloalkyl, —P(=O)(ORʷ)₂, —SO₂N(Rʷ)Rˣ, —NHC(=NH)NHRˣ, —(C₁-C₆)haloalkyl and heteroalkyl; and
R² is:

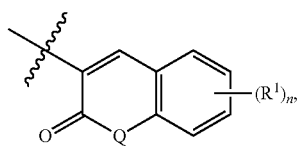

or a salt of such a compound.

According to some preferred embodiments of compounds according to the fourth embodiment of compounds according to Formula IB, $R^2$ is:

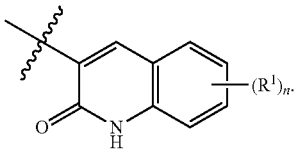

Preferred compounds according to the fourth embodiment of compounds according to Formula IB include: 7-chloro-3-[(7-chloro-2-quinolon-3-yl)sulfonyl]-2-quinolone; 5,7-dibromo-3-[(5,7-dibromo-2-quinolon-3-yl)sulfonyl]-2-quinolone; 3-[(2-quinolon-3-yl)sulfonyl]-2-quinolone; 6-bromo-3-[(6-bromo-2-quinolon-3-yl)sulfonyl]-2-quinolone; 6-chloro-3-[(6-chloro-2-quinolon-3-yl)sulfonyl]-2-quinolone; [(2-quinolon-3-yl)sulfonyl]-2-quinolone (or bis-(2H-2-quinolone-3-yl)sulfone); [(2-quinolon-3-yl)sulfonyl] thiochromen-2-one; 8-ethoxy-3-[(8-ethoxy-2-quinolon-3-yl)sulfonyl]-2-quinolone; 3-[(5,7-dimethoxy-2-quinolon-3-yl)sulfonyl]-5,7-dimethoxy-2-quinolone; 7-methoxy-3-[(7-methoxy-2-quinolon-3-yl)sulfonyl]-2-quinolone; 5-methoxy-3-[(5-methoxy-2-quinolon-3-yl)sulfoneyl]-2-quinolone; 6-fluoro-3-[(6-fluoro-2-quinolon-3-yl)sulfonyl]-2-quinolone; 6-iodo-3-[(6-iodo-2-quinolon-3-yl)sulfonyl]-2-quinolone; 6-nitro-3-[(6-nitro-2-quinolon-3-yl)sulfonyl]-2-quinolone; 8-methoxy-3-[(8-methoxy-6-nitro-2-quinolon-3-yl)sulfonyl]-6-nitro-2-quinolone; 7-hydroxy-3-[(7-hydroxy-2-quinolon-3-yl)sulfonyl]-2-quinolone; 6,8-dinitro-3-[(6,8-dinitro-2-quinolon-3-yl)sulfonyl]-2-quinolone; 6-methoxy-3-[(6-methoxy-2-quinolon-3-yl)sulfonyl]-2-quinolone; 8-methyl-3-[(8-methyl-2-quinolon-3-yl)sulfonyl]-2-quinolone; 5-methyl-3-[(5-methyl-2-quinolon-3-yl)sulfonyl]-2-quinolone; [(benzo[g]quinolin-2-one-3-yl)sulfonyl]benzo[g]quinolin-2-one; 6-trifluoromethoxy-3-[(6-trifluoromethoxy-2-quinolon-3-yl)sulfonyl]-2-quinolone; 6,8-dichloro-3-[(6,8-dichloro-2-quinolon-3-yl)sulfonyl]-2-quinolone; 6,8-dibromo-3-[(6,8-bromo-2-quinolon-3-yl)sulfonyl]-2-quinolone; 6,8-fluoro-3-[(6,8-fluoro-2-quinolon-3-yl)sulfonyl]-2-quinolone; 5-bromo-8-methoxy-3-[(5-bromo-8-methoxy-2-quinolon-3-yl)sulfonyl]-2-quinolone; 6-bromo-8-methoxy-3-[(6-bromo-8-methoxy-2-quinolon-3-yl)sulfonyl]-2-quinolone; 6-chloro-8-bromo-3-[(6-chloro-8-bromo-2-quinolon-3-yl) sulfonyl]-2-quinolone; 8-hydroxy-3-[(8-hydroxy-2-quinolon-3-yl)sulfonyl]-2-quinolone; 6-hydroxy-3-[(6-hydroxy-2-quinolon-3-yl)sulfonyl]-2-quinolone; 6-amino-3-[(6-amino-2-quinolon-3-yl)sulfonyl]-2-quinolone; mixtures thereof; and salts thereof.

According to a fifth embodiment of compounds of Formula IB, there is provided a compound wherein M is (d) or (e):

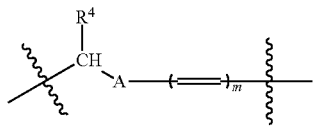

(d)

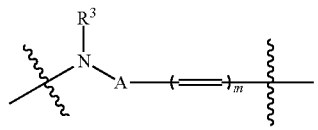

(e)

or a salt of such a compound.

According to some sub-embodiments of the fifth embodiment of compounds according to Formula IB, m is 0 and $R^2$ is:

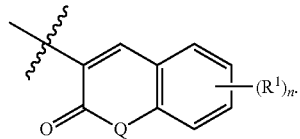

According to some preferred embodiments of compounds according to the fifth embodiment of compounds according to Formula IB, $R^2$ is:

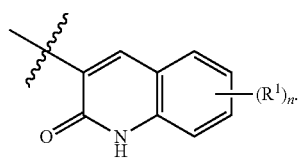

According to other sub-embodiments of the fifth embodiment of compounds according to Formula IB, m is 1, and $R^2$ is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl.

Preferred compounds according to the fifth embodiment of compounds according to Formula IB include: 7-chloro-3-({[(7-chloro-2-quinolone-3-yl)sulfonyl]methyl}sulfonyl)-2-quinolone; 3-({[(2-quinolone-3-yl)sulfonyl] methyl}sulfonyl)-2-quinolone; 5,7-dibromo-3-({[(5,7-dibromo-2-quinolone-3-yl)sulfonyl]methyl}sulfonyl)-2-quinolone; 3-((4-methoxystyryl-sulfonyl)-methylsulfonyl)-7-chloroquinolin-2(1H)-one; 3-((4-methoxystyrylsulfonyl)-methylsulfonyl)quinolin-2(1H)-one; 3-((4-methoxystyrylsulfonyl)methylsulfonyl)-5,7-dibromoquinolin-2(1H)-one; 3-((E)-4-(4-methoxyphenyl)-2-oxo-but-3-enylsulfonyl)-7-chloroquinolin-2(1H)-one; 3-((E)-4-(4-chlorophenyl)-2-oxobut-3-enylsulfonyl)-7-chloroquinolin-2(1H)-one; 3-((E)-4-(2,4-dichlorophenyl)-2-oxobut-3-enylsulfonyl)-7-chloroquinolin-2(1H)-one; 3-((E)-4-(4-chloro-3-nitrophenyl)-2-oxobut-3-enylsulfonyl)-7-chloroquinolin-2(1H)-one; 3-((E)-4-(4-chloro-3-aminophenyl)-2-oxobut-3-enylsulfonyl)-7-chloroquinolin-2(1H)-one; 3-((E)-4-(4-methoxyphenyl)-2-oxobut-3-enylsulfonyl)quinolin-2(1H)-one; 3-((E)-4-(4-chlorophenyl)-2-oxobut-3-enylsulfonyl)quinolin-2(1H)-one; 3-((Z)-4-(4-methoxyphenyl)-2-oxobut-3-enylsulfonyl)-7-chloroquinolin-2(1H)-one; 3-((Z)-4-(4-chlorophenyl)-2-oxobut-3-enylsulfonyl)-7-chloroquinolin-2(1H)-one; 3-((Z)-4-(2,4-dichlorophenyl)-2-oxobut-3-enylsulfonyl)-7-chloroquinolin-2(1H)-one; 3-((Z)-4-(4-chloro-3-nitrophenyl)-2-oxobut-3-enylsulfonyl)-7-chloroquinolin-2(1H)-one; 3-((Z)-4-(4-chloro-3-aminophenyl)-2-oxobut-3- enylsulfonyl)-7-chloroquinolin-2(1H)-one; 3-((Z)-4-(4-methoxyphenyl)-2-oxobut-3-enylsulfonyl)quinolin-2(1H)-one; 3-((Z)-4-(4-chlorophenyl)-2-oxobut-3-enylsulfonyl)quinolin-2(1H)-one; mixtures thereof; and salts thereof.

C. Compounds According to Formula IC

According to a second sub-embodiment of the compounds of the invention, there is provided a compound according to Formula IC:

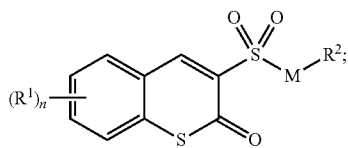

IC wherein $R^1$, $R^2$, $R^w$, $R^x$, $R^y$, $R^z$, $R^3$, $R^4$, M, A and n are as defined herein for compounds of Formula I.

According to a first embodiment of compounds of Formula IC, there is provided a compound wherein M is (a):

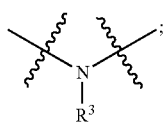

(a)

and each $R^1$ is independently selected from the group consisting of halogen, —($C_1$-$C_8$)hydrocarbyl, —C(=O)$R^y$, —$NR^w{}_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)(O$R^w$)$_2$, —O($C_2$-$C_6$)alkylene-N($CH_3$)$_2$, —O($C_1$-$C_6$)haloalkyl, —P(=O)(O$R^w$)$_2$, —NHC(=NH)NH$R^z$, —($C_1$-$C_6$)haloalkyl and heteroalkyl.

Preferred compounds according to the first embodiment of compounds according to Formula IC include:
N-(4-methoxyphenyl)-2-oxo-2H-thiochromene-3-sulfonamide; N-(3-hydroxy-4-methoxyphenyl)-2-oxo-2H-thiochromene-3-sulfonamide; N-(3-amino-4-fluorophenyl)-2-oxo-2H-thiochromene-3-sulfonamide; N-(4-bromophenyl)-2-oxo-2H-thiochromene-3-sulfonamide; 7-chloro-N-(4-methoxyphenyl)-2-oxo-2H-thiochromene-3-sulfonamide; 7-chloro-N-(3-hydroxy-4-methoxyphenyl)-2-oxo-2H-thiochromene-3-sulfonamide; 7-chloro-N-(3-amino-4-fluorophenyl)-2-oxo-2H-thiochromene-3-sulfonamide; 7-chloro-N-(4-bromophenyl)-2-oxo-2H-thiochromene-3-sulfonamide; 6-bromo-N-(4-methoxyphenyl)-2-oxo-2H-thiochromene-3-sulfonamide 6-chloro-N-(4-methoxyphenyl)-2-oxo-2H-thiochromene-3-sulfonamide; 8-ethoxy-N-(4-methoxyphenyl)-2-oxo-2H-thiochromene-3-sulfonamide; 6-chloro-N-(3-hydroxy-4-methoxyphenyl)-2-oxo-2H-thiochromene-3-sulfonamide; N-(3-amino-4-fluorophenyl)-8-ethoxy-2-oxo-2H-thiochromene-3-sulfonamide; N-(3-amino-4-fluorophenyl)-6-methoxy-2-oxo-2H-thiochromene-3-sulfonamide; N-(4-bromophenyl)-6-methoxy-2-oxo-2H-thiochromene-3-sulfonamide; 8-ethoxy-N-(4-methoxyphenyl)-2-oxo-2H-thiochromene-3-sulfonamide; N-(4-bromo-phenyl)-8-chloro-2-oxo-2H-thiochromene-3-sulfonamide; N-(4-bromophenyl)-8-bromo-2-oxo-2H-thiochromene-3-sulfonamide; mixtures thereof; and salts thereof.

According to a second embodiment of compounds of Formula IC, there is provided a compound wherein M is (b):

(b)

or a salt of such a compound.

Preferred compounds according to the second embodiment of compounds according to Formula IC include:
3-(E)-(4-methoxystyrylsulfonyl)-6-bromo-2H-thiochromen-2-one; 3-(E)-(4-chlorostyrylsulfonyl)-6-bromo-2H-thiochromen-2-one; 3-(E)-(2,4-dichlorostyrylsulfonyl)-6-bromo-2H-thiochromen-2-one; 3-(E)-(4-methoxystyrylsulfonyl)-6-chloro-2H-thiochromen-2-one; 3-(E)-(4-chlorostyrylsulfonyl)-6-chloro-2H-thiochromen-2-one; 3-(E)-(2,4-dichlorostyrylsulfonyl)-6-chloro-2H-thiochromen-2-one; 3-(E)-(4-methoxystyryl-sulfonyl)-5,7-dimethoxy-2H-thiochromen-2-one; 3-(E)-(4-chlorostyrylsulfonyl)-5,7-dimethoxy-2H-thiochromen-2-one; 3-(E)-(2,4-dichlorostyrylsulfonyl)-5,7-dimethoxy-2H-thiochromen-2-one; 3-(E)-(4-methoxystyrylsulfonyl)-7-methoxy-2H-thiochromen-2-one; 3-(E)-(4-chlorostyrylsulfonyl)-7-methoxy-2H-thiochromen-2-one; 3-(E)-(2,4-dichloro-styrylsulfonyl)-7-methoxy-2H-thiochromen-2-one; 3-(Z)-(4-methoxystyrylsulfonyl)-6-bromo-2H-thiochromen-2-one; 3-(Z)-(4-chlorostyrylsulfonyl)-6-bromo-2H-thiochromen-2-one; 3-(Z)-(2,4-dichlorostyrylsulfonyl)-6-bromo-2H-thiochromen-2-one; 3-(Z)-(4-methoxystyrylsulfonyl)-6-chloro-2H-thiochromen-2-one; 3-(Z)-(4-chlorostyrylsulfonyl)-6-chloro-2H-thiochromen-2-one; 3-(Z)-(2,4-dichlorostyrylsulfonyl)-6-chloro-2H-thiochromen-2-one; 3-(Z)-(4-methoxystyrylsulfonyl)-5,7-dimethoxy-2H-thiochromen-2-one; 3-(Z)-(4-chlorostyrylsulfonyl)-5,7-dimethoxy-2H-thiochromen-2-one; 3-(Z)-(2,4-dichlorostyrylsulfonyl)-5,7-dimethoxy-2H-thiochromen-2-one; 3-(Z)-(4-methoxystyrylsulfonyl)-7-methoxy-2H-thiochromen-2-one; 3-(Z)-(4-chlorostyrylsulfonyl)-7-methoxy-2H-thiochromen-2-one; 3-(Z)-(2,4-dichlorostyrylsulfonyl)-7-methoxy-2H-thiochromen-2-one; mixtures thereof; and salts thereof.

According to a third embodiment of compounds of Formula IC, there is provided a compound wherein M is (c):

(c)

or a salt of such a compound.

Preferred compounds according to the third embodiment of compounds according to Formula IC include:
3-(4-methoxybenzylsulfonyl)-2H-thiochromen-2-one; 3-(4-methoxy-benzyl-sulfonyl)-5,7-dimethoxy-2H-thiochromen-2-one; 3-(4-methoxybenzylsulfonyl)-6,8-dinitro-2H-thiochromen-2-one; 3-(4-methoxybenzylsulfonyl)-6-bromo-2H-thiochromen-2-one; 3-(4-methoxybenzylsulfonyl)-6-chloro-2H-thiochromen-2-one; 3-(4-methoxybenzylsulfonyl)-7-methoxy-2H-thiochromen-2-one; 3-(4-methoxybenzyl-sulfonyl)-7-hydroxy-2H-thiochromen-2-one; 3-(4-methoxybenzylsulfonyl)-7-chloro-2H-thiochromen-2-one; 3-(4-methoxybenzylsulfonyl)-5,7- dibromo-2H-thiochromen-2-one; 3-(4-chlorobenzylsulfonyl)-2H-thiochromen-2-one; 3-(4-chlorobenzylsulfonyl)-7-chloro-2H-thiochromen-2-one; 3-(4-chlorobenzylsulfonyl)-5,7-dibromo-2H-thiochromen-2-one; 3-(2,4-dichlorobenzylsulfonyl)-2H-thiochromen-2-one; 3-(2,4-dichlorobenzylsulfonyl)-7-chloro-2H-thiochromen-2-one; 3-(2,4-dichlorobenzylsulfonyl)-5,7-dibromo-2H-thiochromen-2-one; 3-(4-methoxy-3-nitrobenzylsulfonyl)-5,7-dimethoxy-2H-thiochromen-2-one; 3-(4-methoxy-3-nitrobenzylsulfonyl)-7-methoxy-2H-thiochromen-2-one; 3-(4-methoxy-3-nitrobenzylsulfonyl)-7-hydroxy-2H-thiochromen-2-one; 3-(4-methoxy-3-nitrobenzylsulfonyl)-7-chloro-2H-thiochromen-2-one; 3-(4-methoxy-3-nitrobenzylsulfonyl)-2H-thiochromen-2-one; 3-(4-methoxy-3-nitrobenzylsulfonyl)-5,7-dibromo-2H-thiochromen-2-one; 3-(4-chloro-3-nitrobenzylsulfonyl)-6-chloro-2H-thiochromen-2-one; 3-(4-chloro-3-nitrobenzylsulfonyl)-7-chloro-2H-thiochromen-2-one; 3-(4-chloro-3-nitrobenzylsulfonyl)-2H-thiochromen-2-one; 3-(4-chloro-3-nitrobenzylsulfonyl)-5,7-dibromo-2H-thiochromen-2-one; 3-(4-chloro-3-aminobenzylsulfonyl)-7-chloro-2H-thiochromen-2-one; 3-(4-chloro-3-aminobenzylsulfonyl)-2H-thiochromen-2-one; 3-(4-chloro-3-aminobenzylsulfonyl)-5,7-dibromo-2H-thiochromen-2-one; 3-(4-chloro-3-aminobenzylsulfonyl)-6-chloro-2H-thiochromen-2-one; mixtures thereof; and salts thereof.

According to a fourth embodiment of compounds of Formula IC, there is provided a compound wherein:

M is a single bond;

each $R^1$ is independently selected from the group consisting of halogen, —$(C_1-C_8)$hydrocarbyl, —C(=O)$R^y$, —N($R^w$)C(=O)$R^y$, —N($R^w$)CH($R^z$)C(=O)$R^y$, —N($R^w$)SO$_2R^y$, —N($R^w$)($C_1-C_4$)alkylene-CO$_2R^w$, —NO$_2$, —CN, —O$R^w$, —OC(=O)$R^y$, —OCH($R^z$)C(=O)$R^y$, —OSO$_2R^y$, —O($C_1-C_4$)alkylene-CO$_2R^w$, —OP(=O)(O$R^w$)$_2$, —O($C_2-C_6$)alkylene-N(CH$_3$)$_2$, —O($C_1-C_6$)haloalkyl, —P(=O)(O$R^w$)$_2$, —SO$_2$N($R^w$)$R^x$, —NHC(=NH)NH$R^x$, —($C_1-C_6$) haloalkyl and heteroalkyl; and $R^2$ is:

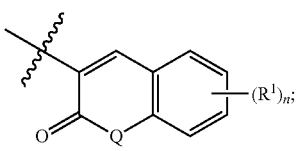

or a salt of such a compound.

According to some preferred embodiments of compounds according to the fourth embodiment of compounds according to Formula IB, $R^2$ is:

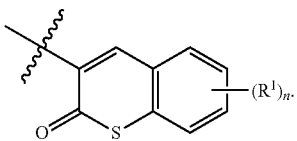

Preferred compounds according to the fourth embodiment of compounds according to Formula IC include:

6-bromo-3-[(6-bromo-2-oxothiochromen-3-yl)sulfonyl]thiochromen-2-one; 6-chloro-3-[(6-chloro-2-oxothiochromen-3-yl)sulfonyl]thiochromen-2-one; (2-oxothiochromen-3-yl)sulfonyl]thiochromen-2-one (or bis-(2H-chromene-2-one-3-yl)sulfone); (2-oxothiochromen-3-yl)sulfonyl]quinolin-2-one; 8-ethoxy-3-[(8-ethoxy-2-oxothiochromen-3-yl)sulfonyl]thiochromen-2-one; 3-[(5,7-dimethoxy-2-oxothiochromen-3-yl)sulfonyl]-5,7-dimethoxythiochromen-2-one; 7-methoxy-3-[(7-methoxy-2-oxothiochromen-3-yl)sulfonyl]-thiochromen-2-one; 5-methoxy-3-[(5-methoxy-2-oxothiochromen-3-yl)sulfonyl]thiochromen-2-one; 6-fluoro-3-[(6-fluoro-2-oxothiochromen-3-yl)sulfonyl]thiochromen-2-one; 6-iodo-3-[(6-iodo-2-oxothio-chromen-3-yl)sulfonyl]thiochromen-2-one; 6-nitro-3-[(6-nitro-2-oxothiochromen-3-yl)sulfonyl]thiochromen-2-one; 8-methoxy-3-[(8-methoxy-6-nitro-2-oxothiochromen-3-yl)sulfonyl]-6-nitrothiochromen-2-one; 7-hydroxy-3-[(7-hydroxy-2-oxothiochromen-3-yl)sulfonyl]thiochromen-2-one; 7-chloro-3-[(7-chlorothiochromen-2-one-3-yl)sulfonyl]-thiochromen-2-one; 5,7-dibromo-3-[(5,7-dibromothiochromen-2-one-3-yl)sulfonyl]-thiochromen-2-one; 3-[(thiochromen-2-one-3-yl)-sulfonyl]thiochromen-2-one; 6,8-dinitro-3-[(6,8-dinitrothiochromen-2-one-3-yl)sulfonyl]thiochromen-2-one; 6-methoxy-3-[(6-methoxythiochromen-2-one-3-yl)sulfonyl]thiochromen-2-one; 8-methyl-3-[(8-methylthiochromen-2-one-3-yl)sulfonyl]thiochromen-2-one; 5-methyl-3-[(5-methylthiochromen-2-one-3-yl)-sulfonyl]thiochromen-2-one; [(benzo[g]thiochromen-2-one-3-yl)sulfonyl]-benzo[g]thiochromen-2-one; 6-trifluoromethoxy-3-[(6-trifluoromethoxythiochromen-2-one-3-yl)sulfonyl]thiochromen-2-one; 6,8-dichloro-3-[(6,8-dichlorothiochromen-2-one-3-yl)sulfonyl]thiochromen-2-one; 6,8-dibromo-3-[(6,8-bromothiochromen-2-one-3-yl)sulfonyl]thiochromen-2-one; 6,8-fluoro-3-[(6,8-fluorothiochromen-2-one-3-yl)sulfonyl]thiochromen-2-one; 5-bromo-8-methoxy-3-[(5-bromo-8-methoxythiochromen-2-one-3-yl)sulfonyl]thiochromen-2-one; 6-bromo-8-methoxy-3-[(6-bromo-8-methoxythiochromen-2-one-3-yl)sulfonyl]thiochromen-2-one; 6-chloro-8-bromo-3-[(6-chloro-8-bromothiochromen-2-one-3-yl)sulfonyl]thiochromen-2-one; 8-hydroxy-3-[(8-hydroxythiochromen-2-one-3-yl)sulfonyl]thiochromen-2-one; 6-hydroxy-3-[(6-hydroxythiochromen-2-one-3-yl)sulfonyl]thiochromen-2-one; 6-amino-3-[(6-aminothiochromen-2-one-3-yl)sulfonyl]thiochromen-2-one; mixtures thereof; and salts thereof.

According to a fifth embodiment of compounds of Formula IC, there is provided a compound wherein M is (d) or (e):

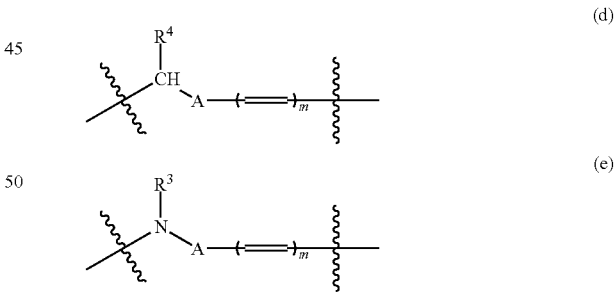

or a salt of such a compound.

According to some sub-embodiments of the fifth embodiment of compounds according to Formula IC, m is 0 and $R^2$ is:

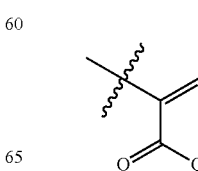

According to some preferred embodiments of compounds according to the fifth embodiment of compounds according to Formula IC, $R^2$ is:

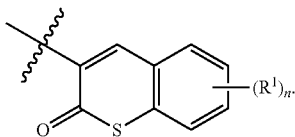

According to other sub-embodiments of the fifth embodiment of compounds according to Formula IC, m is 1, and $R^2$ is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl.

Preferred compounds according to the fifth embodiment of compounds according to Formula IC include:
6-chloro-3-({[(6-chloro-2-oxothiochromen-3-yl)sulfonyl]methyl}sulfonyl)-thiochromen-2-one; 6-bromo-3-({[(6-bromo-2-oxothiochromen-3-yl)sulfonyl]methyl}-sulfonyl) thiochromen-2-one; 6-iodo-3-({[(6-iodo-2-oxothiochromen-3-yl)sulfonyl]-methyl}sulfonyl) thiochromen-2-one; 8-ethoxy-3-({[(8-ethoxy-2-oxothiochromen-3-yl)sulfonyl]methyl}-sulfonyl) thiochromen-2-one; 3-({[(5,7-dimethoxy-2-oxothiochromen-3-yl)-sulfonyl]methyl}sulfonyl)-5,7-dimethoxythiochromen-2-one; 7-methoxy-3 -({[(7-methoxy-2-oxothiochromen-3-yl)sulfonyl]methyl}sulfonyl) thiochromen-2-one; 5-methoxy-3-({[(5-methoxy-2-oxothochromen-3-yl)sulfonyl]methyl}-sulfonyl)-thiochromen-2-one; 7-hydroxy-3-({[(7-hydroxy-2-oxothiochromen-3-yl)sulfonyl]-methyl}-sulfonyl) thiochromen-2-one; 3-({[(6,8-dinitro-2-oxothiochromen-3-yl)sulfonyl]methyl}-sulfonyl)-6,8-dinitrothiochromen-2-one; 3-(E)-((4-methoxystyrylsulfonyl)methyl-sulfonyl)-7-chloro-2H-thiochromen-2-one; 3-(E)-((4-methoxystyrylsulfonyl)methyl-sulfonyl)-6-chloro-2H-thiochromen-2-one; 3-(E)-((4-methoxystyrylsulfonyl) methyl-sulfonyl)-6-bromo-2H-thiochromen-2-one; 3-(E)-((4-methoxystyrylsulfonyl)methyl-sulfonyl)-7-iodo-2H-thiochromen-2-one; 3-(E)-((4-methoxystyrylsulfonyl) methyl-sulfonyl)-8-ethoxy-2H-thiochromen-2-one; 3-(E)-((4-methoxystyrylsulfonyl)methyl-sulfonyl)-7-methoxy-2H-thiochromen-2-one; 3-(E)-((4-methoxystyrylsulfonyl)methyl-sulfonyl)-5-methoxy-2H-thiochromen-2-one; 3-(E)-((4-methoxystyrylsulfonyl)-methyl-sulfonyl)-5,7-dimethoxy-2H-thiochromen-2-one; 3-(Z)-((4-methoxystyrylsulfonyl)methyl-sulfonyl)-7-chloro-2H-thiochromen-2-one; 3-(Z)-((4-methoxy-styrylsulfonyl)methyl-sulfonyl)-6-chloro-2H-thiochromen-2-one; 3-(Z)-((4-methoxystyryl-sulfonyl)methyl-sulfonyl)-6-bromo-2H-thiochromen-2-one; 3-(Z)-((4-methoxystyrylsulfonyl)-methyl-sulfonyl)-7-iodo-2H-thiochromen-2-one; 3-(Z)-((4-methoxystyrylsulfonyl)methyl-sulfonyl)-8-ethoxy-2H-thiochromen-2-one; 3-(Z)-((4-methoxystyrylsulfonyl)-methyl-sulfonyl)-7-methoxy-2H-thiochromen-2-one; 3-(Z)-((4-methoxystyrylsulfonyl)-methyl-sulfonyl)-5-methoxy-2H-thiochromen-2-one; 3-(Z)-((4-methoxystyrylsulfonyl)-methyl-sulfonyl)-5,7-dimethoxy-2H-thiochromen-2-one; 3-((E)-4-(4-methoxyphenyl)-2-oxobut-3-enylsulfonyl)-7-chloro-2H-thiochromen-2-one, 3-((E)-4-(4-methoxyphenyl)-2-oxobut-3-enylsulfonyl)-6-chloro-2H-thiochromen-2-one; 3-((E)-4-(4-methoxyphenyl)-2-oxobut-3-enylsulfonyl)-6-bromo-2H-thiochromen-2-one; 3-((E)-4-(4-methoxyphenyl)-2-oxobut-3-enylsulfonyl)-6-iodo-2H-thiochromen-2-one; 3-((E)-4-(4-methoxyphenyl)-2-oxobut-3-enylsulfonyl)-8-ethoxy-2H-thiochromen-2-one; 3-((E)-4-(4-methoxyphenyl)-2-oxobut-3-enylsulfonyl)-7-methoxy-2H-thiochromen-2-one; 3-((E)-4-(4-methoxyphenyl)-2-oxobut-3-enylsulfonyl)-5-methoxy-2H-thiochromen-2-one; 3-((E)-4-(4-methoxyphenyl)-2-oxobut-3-enylsulfonyl)-5,7-dimethoxy-2H-thiochromen-2-one; 3-((Z)-4-(4-methoxyphenyl)-2-oxobut-3-enylsulfonyl)-7-chloro-2H-thiochromen-2-one, 3-((Z)-4-(4-methoxyphenyl)-2-oxobut-3-enylsulfonyl)-6-chloro-2H-thiochromen-2-one; 3-((Z)-4-(4-methoxyphenyl)-2-oxobut-3-enylsulfonyl)-6-bromo-2H-thiochromen-2-one; 3-((Z)-4-(4-methoxyphenyl)-2-oxobut-3-enylsulfonyl)-6-iodo-2H-thiochromen-2-one; 3-((Z)-4-(4-methoxyphenyl)-2-oxobut-3-enylsulfonyl)-8-ethoxy-2H-thiochromen-2-one; 3-((Z)-4-(4-methoxyphenyl)-2-oxobut-3-enylsulfonyl)-7-methoxy-2H-thiochromen-2-one; 3-((Z)-4-(4-methoxyphenyl)-2-oxobut-3-enylsulfonyl)-5-methoxy-2H-thiochromen-2-one; 3-((Z)-4-(4-methoxyphenyl)-2-oxobut-3-enylsulfonyl)-5,7-dimethoxy-2H-thiochromen-2-one; mixtures thereof; and salts thereof.

The present invention further embraces isolated compounds according to Formula I. The expression "isolated compound" refers to a compound of Formula I, or a mixture of compounds according to Formula I, wherein the isolated compound contains the named compound or mixture of compounds according to Formula I in an amount of at least 10 percent by weight of the total weight. Preferably, the isolated compound contains the named compound or mixture of compounds in an amount of at least 50 percent by weight of the total weight; more preferably at least 80 percent by weight of the total weight; and most preferably at least 90 percent or at least 95 percent by weight of the total weight.

According to another embodiment of the invention, there is provided a compound according to Formula I:

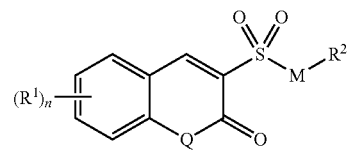

wherein:
each Q is independently O, S, or NH;
each $R^1$ is independently selected from the group consisting of halogen, —$(C_1$-$C_8)$hydrocarbyl, —C(=O)$R^y$, —$NR^w_2$, —N($R^w$)C(=O)$R^y$, —N($R^w$)CH($R^z$)C(=O)$R^y$, —N($R^w$)SO$_2R^y$, —N($R^w$)($C_1$-$C_4$)alkylene-CO$_2R^w$, —NO$_2$, —CN, —OR$^w$, —OC(=O)$R^y$, —OCH($R^z$)C(=O)$R^y$, —OSO$_2R^y$, —O($C_1$-$C_4$)alkylene-CO$_2R^w$, —OP(=O) (OR$^w$)$_2$, —O($C_2$-$C_6$)alkylene-N(CH$_3$)$_2$, —O($C_1$-$C_6$)haloalkyl, —P(=O)(OR$^w$)$_2$, —SO$_2$N($R^w$)$R^x$, —NHC(=NH)NHR$^x$, —($C_1$-$C_6$)haloalkyl and heteroalkyl;

$R^w$ is —H;
$R^x$ is —H, —($C_1$-$C_8$)hydrocarbyl or —C(=O)($C_1$-$C_8$)hydrocarbyl;
$R^y$ is selected from the group consisting of —H, —($C_1$-$C_8$) hydrocarbyl, —O($C_1$-$C_8$)hydrocarbyl, substituted phenyl, substituted heterocyclyl($C_1$-$C_3$)alkyl, heteroaryl($C_1$-$C_3$) alkyl, —($C_2$-$C_{10}$)heteroalkyl, —($C_1$-$C_6$)haloalkyl, —CH ($R^z$)NHR$^x$, —N($R^w$)$R^x$, —($C_1$-$C_3$)alkyleneNH$_2$, —($C_1$-$C_3$) alkyleneN(CH$_3$)$_2$, —($C_1$-$C_3$)perfluoroalkyleneN(CH$_3$)$_2$, —($C_1$-$C_2$)alkyleneN$^+$(($C_1$-$C_3$)alkyl)$_3$, —($C_1$-$C_3$)alkylene- $N^+(CH_2CH_2OH)_3$, $—(C_1-C_3)$alkylene-$OR^x$, $—(C_1-C_4)$alkylene-$CO_2R^x$, $—(C_1-C_4)$alkylene-$CO_2N(R^w)R^x$, $—(C_1-C_4)$alkylene-$C(=O)$halogen, halo$(C_1-C_3)$alkyl and $—(C_1-C_4)$perfluoroalkylene-$CO_2R^x$;

$R^z$ is selected from the group consisting of —H, $—(C_1-C_6)$alkyl, $—(CH_2)_3—NH—C(NH_2)(=NH)$, $—CH_2C(=O)NH_2$, $—CH_2COOH$, $—CH_2SH$, $—(CH_2)_2C(=O)—NH_2$, $—(CH_2)_2CO_2H$, $—CH_2$-(2-imidazolyl), $—(CH_2)_4—NH_2$, $—(CH_2)_2—S—CH_3$, phenyl, $—CH_2$-phenyl, $—CH_2—OH$, $—CH(OH)—CH_3$, $—CH_2$-(3-indolyl) and $—CH_2$-(4-hydroxyphenyl);

n is 0, 1, 2, 3 or 4;

M is selected from the group consisting of a single bond and (b), (c), (d) and (e):

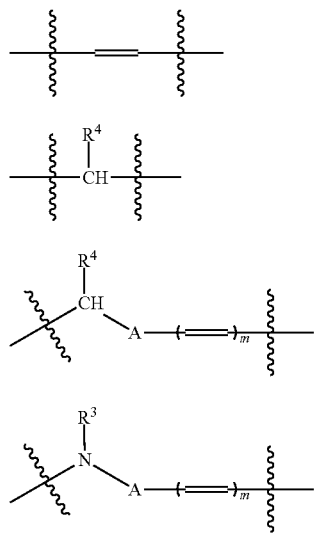

$R^2$ is substituted or unsubstituted aryl or substituted or unsubstituted heteroaryl;

$R^3$ and $R^4$ are independently selected from the group consisting of —H and $—(C_1-C_6)$alkyl; and A is $—SO_2—$ or $—C(=O)—$;

provided that:
(i) when M is a single bond,
then $R^2$ is:

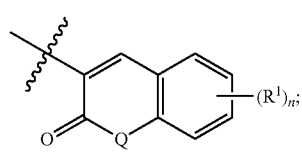

$R^1$ is other than $—NR^w{}_2$;
(ii) when m is 0;
then $R^2$ is:

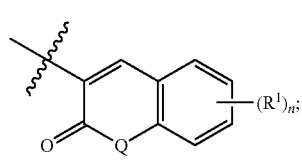

and
(iii) when n is 0, then $R^2$ is other than unsubstituted phenyl;
or a salt of such a compound.

Preferred compounds according to Formula I wherein $R^w$ is —H include, for example, 3-(4-methoxy-3-nitrobenzylsulfonyl)-7-hydroxy-2H-chromen-2-one; 7-hydroxy-3-[(7-hydroxy-2-oxochromen-3-yl)sulfonyl]chromen-2-one; 8-hydroxy-3-[(8-hydroxy-2-oxochromen-3-yl)sulfonyl]chromen-2-one; 6-hydroxy-3-[(6-hydroxy-2-oxochromen-3-yl)sulfonyl]chromen-2-one; 7-hydroxy-3-({[(7-hydroxy-2-oxochromen-3-yl)sulfonyl]-methyl}sulfonyl)-chromen-2-one; 7-hydroxy-3-[(7-hydroxy-2-quinolon-3-yl)sulfonyl]-2-quinolone; 8-hydroxy-3-[(8-hydroxy-2-quinolon-3-yl)sulfonyl]-2-quinolone; 6-hydroxy-3-[(6-hydroxy-2-quinolon-3-yl)sulfonyl]-2-quinolone; 3-(4-methoxy-benzylsulfonyl)-7-hydroxy-2H-thiochromen-2-one; 3-(4-methoxy-3-nitro-benzylsulfonyl)-7-hydroxy-2H-thiochromen-2-one; 7-hydroxy-3-[(7-hydroxy-2-oxothiochromen-3-yl)sulfonyl]thiochromen-2-one; 8-hydroxy-3-[(8-hydroxythiochromen-2-one-3-yl)sulfonyl]thiochromen-2-one; 6-hydroxy-3-[(6-hydroxythiochromen-2-one-3-yl)sulfonyl]thiochromen-2-one; 7-hydroxy-3-({[(7-hydroxy-2-oxothiochromen-3-yl)sulfonyl]-methyl}-sulfonyl)thiochromen-2-one; mixtures thereof; and salts thereof.

II. Intermediates in the Preparation of Formula I Compounds

According to another embodiment of the invention, there are provided synthetic intermediates of Formula II:

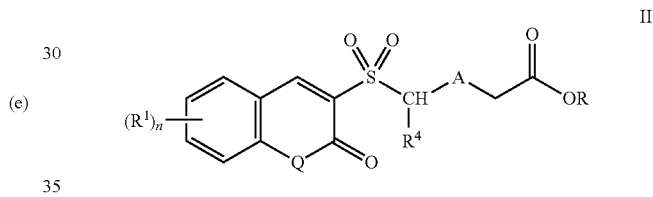

useful in the preparation of compounds according to Formula I wherein M is (d);

$R^1$, $R^4$, Q and A are as defined herein, and R is —H or $—(C_1-C_7)$hydrocarbyl, preferably benzyl or $—(C_1-C_6)$ alkyl, more preferably $—(C_1-C_3)$ alkyl, most preferably methyl or ethyl.

Compounds according to Formula II, wherein A is $—SO_2—$, may be prepared, for example, by
(a) reacting a compound according to Formula IIA:

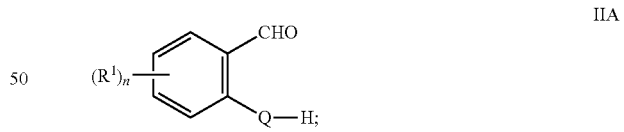

wherein $R^1$, Q and n are as defined herein;
with a compound according to Formula IIB:

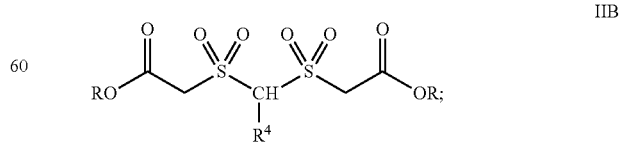

wherein R and $R^4$ are as defined herein; and
(b) isolating a compound according to Formula II from the reaction products.

Compounds according to Formula IIB, wherein R is —(C$_1$-C$_7$)hydrocarbyl, may be prepared, for example by:

(a) reacting a compound according to Formula IIB, wherein R is —H, with a hydrocarbyl alcohol and a catalytic amount of an acid reagent; and (b) isolating a compound according to Formula IIB, wherein R is —(C$_1$-C$_7$)hydrocarbyl, from the reaction products.

Preferred acid reagents include, for example, sulfuric acid, toluene sulfonic acid and hydrochloric acid.

Compounds according to Formula IIB may be prepared, for example by:

(a) reacting a compound according to Formula IIC:

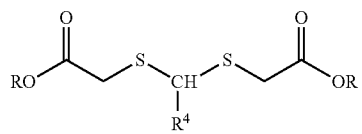

IIC wherein R and R$^4$ are as defined herein, with an oxidizing agent capable of oxidizing a sulfide to a sulfone; and (b) isolating a compound according to Formula IIB from the reaction products.

Compounds according to Formula IIC may be prepared, for example by:

(a) reacting a compound according to Formula IID:

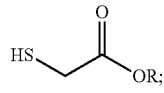

IID wherein R is as defined herein, with a compound of Formula IIE:

IIE wherein R$^4$ is as defined herein; and (b) isolating a compound according to Formula IIC from the reaction products.

According to another embodiment of the invention, there are provided synthetic intermediates according to Formula III:

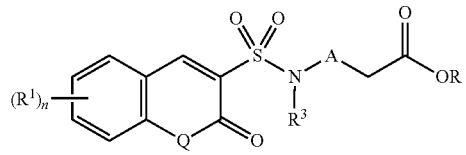

III useful in the preparation of compounds according to Formula I wherein:

M is (e);

R$^1$, R$^3$, Q and A are as defined herein, and R is —H or —(C$_1$-C$_7$)hydrocarbyl, preferably benzyl or —(C$_1$-C$_6$) alkyl, more preferably —(C$_1$-C$_3$) alkyl, most preferably methyl or ethyl.

Compounds according to Formula III, wherein A is —SO$_2$—, may be prepared, for example, by (a) reacting a compound according to Formula IIA:

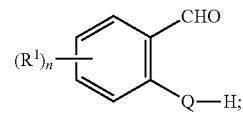

IIA wherein R$^1$, Q and n are as defined herein;
with a compound according to Formula IIIA:

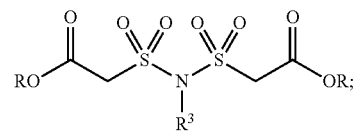

IIA wherein R and R$^3$ are as defined herein; and (b) isolating a compound according to Formula III from the reaction products.

According to another embodiment of the invention, there are provided synthetic intermediates according to Formula IV:

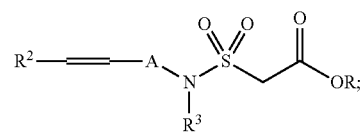

IV useful in the preparation of compounds according to Formula I wherein M is (e); R$^2$, R$^3$ and A are as defined herein; and R is —H or —(C$_1$-C$_7$)hydrocarbyl, preferably benzyl or —(C$_1$-C$_6$) alkyl, more preferably —(C$_1$-C$_3$) alkyl, most preferably methyl or ethyl.

Compounds according to Formula IV, wherein A is —SO$_2$— may be prepared, for example, by (a) reacting a compound according to Formula IVA:

IVA with a compound according to Formula IIIA:

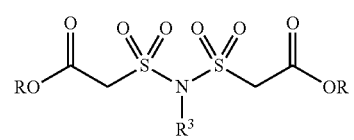

IIIA wherein R$^2$, R$^3$ and R are as defined herein; and (b) isolating a compound according to Formula IV from the reaction products.

Compounds according to Formula IIIA, may be prepared, for example by:

(a) reacting a compound according to Formula IIIB:

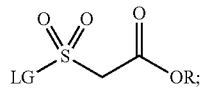
IIIB wherein R is —(C$_1$-C$_7$)hydrocarbyl and LG is a leaving group, preferably an alkylsulfonate, a haloalkyl sulfonate, an aralkyl sulfonate or a halogen, more preferably a halogen, most preferably Cl;

with a compound of Formula IIIC:

IIC;

and (b) isolating a compound according to Formula IIIA from the reaction products.

According to another embodiment of the invention, there are provided synthetic intermediates according to Formula V:

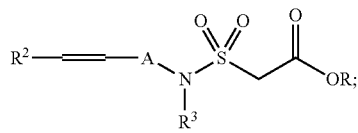
IV useful in the preparation of compounds according to Formula I wherein M is (d); R$^2$, R$^4$ and A are as defined herein; and R is —H or —(C$_1$-C$_7$)hydrocarbyl, preferably benzyl or —(C$_1$-C$_6$) alkyl, more preferably —(C$_1$-C$_3$) alkyl, most preferably methyl or ethyl.

Compounds according to Formula V, wherein A is —SO$_2$— may be prepared, for example, by (a) reacting a compound according to Formula IVA:

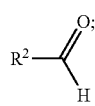
IVA with a compound according to Formula IIB:

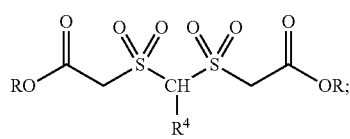
IIB and (b) isolating a compound according to Formula V from the reaction products.

III. Processes of Preparing Compounds According to Formula I

According to another aspect of the invention, processes for preparing compounds according to Formula I are provided.

According to one embodiment of the invention, a compound according to Formula I:

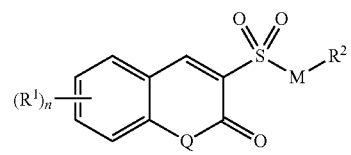
I wherein M, R$^1$, R$^2$, Q and n are as defined herein may be prepared by:

(a) reacting a compound according to Formula IIA:

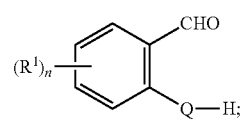
IIA wherein R$^1$, n and Q are as defined herein;
with a compound of Formula VI:

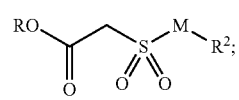
VI wherein R$^2$ and M are as defined herein, and R is —H or —(C$_1$-C$_7$)hydrocarbyl, preferably benzyl or —(C$_1$-C$_6$)alkyl, more preferably —(C$_1$-C$_3$)alkyl, most preferably methyl or ethyl; and (b) isolating a compound according to Formula I from the reaction products.

According to a first sub-embodiment of the above method of preparing a compound of Formula I, there is further provided a method of preparing a compound of Formula I wherein M is (a):

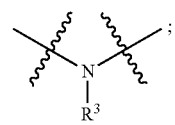
(a)

and

R$^1$, R$^2$, R$^3$, Q and n are as defined herein; said method comprising the steps of:

(a) reacting a compound according to Formula IIA:

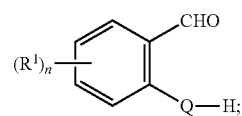
IIA wherein R$^1$, n and Q are as defined herein;

with a compound of Formula VIA:

$$\text{VIA}$$

wherein $R^2$ and $R^3$ are as defined herein, and R is —H or —($C_1$-$C_7$)hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to a second sub-embodiment of the above method of preparing a compound of Formula I, there is further provided a method of preparing a compound of Formula I wherein M is (b):

$$\text{(b)}$$

and $R^1$, $R^2$, Q and n are as defined herein; said method comprising the steps of (a) reacting a compound according to Formula IIA:

$$\text{IIA}$$

wherein $R^1$, n and Q are as defined herein;
with a compound of Formula VIB:

$$\text{VIB}$$

wherein $R^2$ is as defined herein, and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to a third sub-embodiment of the above method of preparing a compound of Formula I, there is further provided a method of preparing a compound of Formula I wherein M is (c):

$$\text{(c)}$$

and $R^1$, $R^2$ $R^4$, Q and n are as defined herein; said method comprising the steps of:

(a) reacting a compound according to Formula IIA:

$$\text{IIA}$$

wherein $R^1$, n and Q are as defined herein;
with a compound of Formula VIC:

$$\text{VIC}$$

wherein $R^2$ is as defined herein, and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to another embodiment of the invention, there is provided a process of preparing a compound according to Formula I, wherein M is a single bond; said method comprising the steps of:

(a) reacting a compound according to Formula IIA:

$$\text{IIA}$$

wherein $R^1$, n and Q are as defined herein;
with dicarboxymethylsulfone:

and (b) isolating a compound according to Formula I from the reaction products.

According to another embodiment of the invention, there is provided a process of preparing a compound according to Formula I wherein M is (d):

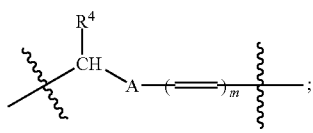
(d)

$R^4$ and A are as defined herein; and m is 1; said method comprising the steps of:
(a) reacting a compound according to Formula IIA:

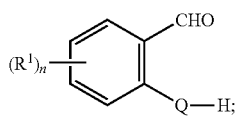
IIA wherein $R^1$, n and Q are as defined herein;
with a compound of Formula V:

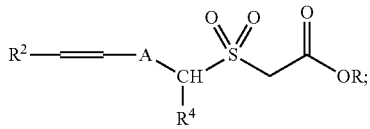
V wherein $R^2$, $R^4$ and A are as defined herein, and R is —H or —($C_1$-$C_7$)hydrocarbyl, preferably benzyl or —($C_1$-$C_6$) alkyl, more preferably —($C_1$-$C_3$) alkyl, most preferably methyl or ethyl; and
(b) isolating a compound according to Formula I from the reaction products.

According to another embodiment of the invention, there is provided a process of preparing a compound according to Formula I wherein M is (d):

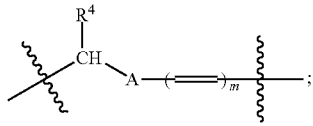
(d)

$R^4$ and A are as defined herein; and m is 0; said method comprising the steps of:
(a) reacting a compound according to Formula IIA:

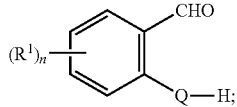
IIA wherein $R^1$, n and Q are as defined herein;
with a compound of Formula IIB:

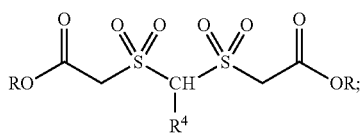
IIB wherein $R^4$ is as defined herein and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and
(b) isolating a compound according to Formula I from the reaction products.

According to another embodiment of the invention, there is provided a process of preparing a compound according to Formula I wherein M is (e):

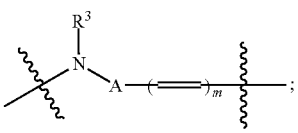
(e)

$R^3$ and A are as defined herein; and m is 1; said method comprising the steps of:
(a) reacting a compound according to Formula IIA:

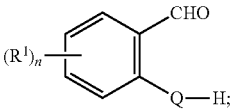
IIA wherein $R^1$, n and Q are as defined herein;
with a compound of Formula IV:

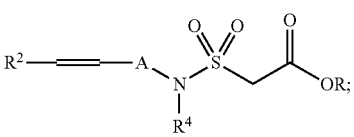
IV wherein $R^2$, $R^3$ and A are as defined herein, and R is —H or —($C_1$-$C_7$)hydrocarbyl, preferably benzyl or —($C_1$-$C_6$) alkyl, more preferably —($C_1$-$C_3$) alkyl, most preferably methyl or ethyl; and
(b) isolating a compound according to Formula I from the reaction products.

According to another embodiment of the invention, there is provided a process of preparing a compound according to Formula I wherein M is (e):

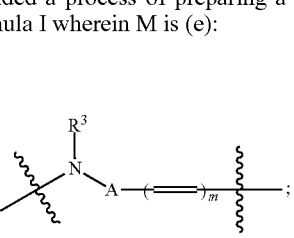
(e)

$R^3$ and A are as defined herein; and m is 0; said method comprising the steps of:
(a) reacting a compound according to Formula IIA:

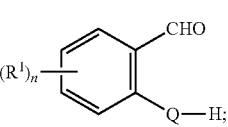
IIA wherein $R^1$, n and Q are as defined herein;

with a compound of Formula IIIA:

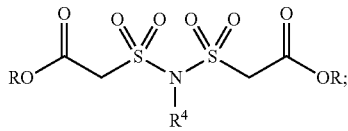

wherein $R^3$ is as defined herein, and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to another embodiment of the invention, there is provided a process of preparing a compound according to Formula I wherein M is (d):

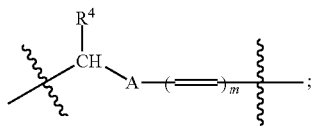

$R^4$ and A are as defined herein; and m is 1; said method comprising the steps of:

(a) reacting a compound according to Formula II:

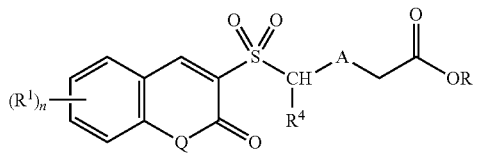

wherein each $R^1$, $R^w$, $R^x$, $R^y$, $R^z$, R, Q and n are as defined herein; or a salt of such a compound;

with a compound of formula IVA:

wherein $R^2$ is substituted or unsubstituted aryl or substituted or unsubstituted heteroaryl;

provided that the compound according to Formula IVA is other than a compound according to Formula IIA; and (b) isolating a compound according to Formula I from the reaction products.

According to another embodiment of the invention, there is provided a process of preparing a compound according to Formula I wherein M is (e):

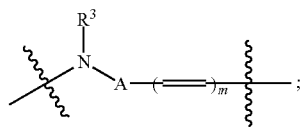

$R^3$ and A are as defined herein; and m is 1; said method comprising the steps of:

(a) reacting a compound according to Formula III:

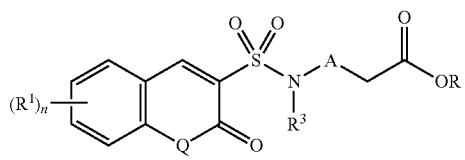

wherein each $R^1$, $R^w$, $R^x$, $R^y$, $R^z$, R, Q and n are as defined herein; or a salt of such a compound;

with a compound of formula IVA:

wherein $R^2$ is substituted or unsubstituted aryl or substituted or unsubstituted heteroaryl;

provided that the compound according to Formula IVA is other than a compound according to Formula IIA; and (b) isolating a compound according to Formula I from the reaction products.

According to another embodiment of the invention, there is provided a process of preparing a compound according to Formula I wherein M is (d):

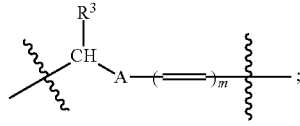

$R^3$ and A are as defined herein; and m is 0; said method comprising the steps of:

(a) reacting a compound according to Formula II:

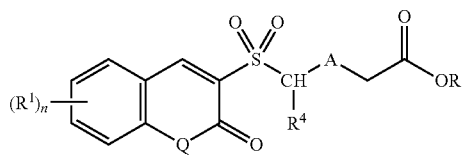

wherein each $R^1$, $R^w$, $R^x$, $R^y$, $R^z$, R, Q and n are as defined herein; or a salt of such a compound;

with a compound according to Formula IIA:

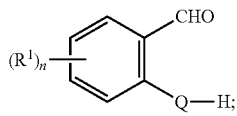

wherein $R^1$, Q and n are as defined above; and (b) isolating a compound according to Formula I from the reaction products.

According to another embodiment of the invention, there is provided a process of preparing a compound according to Formula I wherein M is (e):

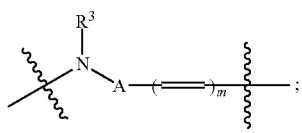

$R^3$ and A are as defined herein; and m is 0; said method comprising the steps of:

(a) reacting a compound according to Formula III:

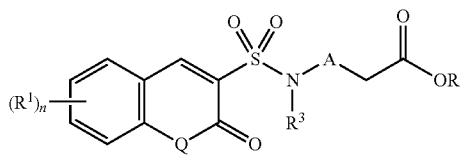

wherein each $R^1$, $R^w$, $R^x$, $R^y$, $R^z$, R, Q and n are as defined herein; or a salt of such a compound;
provided that $R^1$ is other than —$NR^w{}_2$;
with a compound according to Formula IIA:

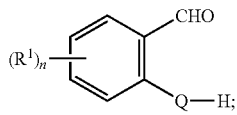

wherein $R^1$, Q and n are as defined above; and
(b) isolating a compound according to Formula I from the reaction products.

According to another embodiment of the invention, a pharmaceutical composition is provided comprising a pharmaceutically acceptable carrier and one or more compounds according to Formula I.

According to another embodiment of the invention, a method of treating an individual suffering from a proliferative disorder, particularly cancer, is provided, comprising administering to said individual an effective amount of at least one compound according to Formula I, alone, or in combination with a pharmaceutically acceptable carrier.

According to another embodiment of the invention, a method of inhibiting growth of tumor cells in an individual suffering from a proliferative disorder, particularly cancer, is provided comprising administering to said individual an effective amount of at least one compound according to Formula I, alone, or in combination with a pharmaceutically acceptable carrier.

According to another embodiment, a method of inducing apoptosis of cancer cells, preferably tumor cells, in an individual afflicted with cancer is provided, comprising administering to said individual an effective amount of at least one compound according to Formula I, alone or in combination with a pharmaceutically acceptable carrier.

According to other embodiments of the invention, there is provided the use of at least one compound according to Formula I, either alone or in combination with a pharmaceutically acceptable carrier, for preparation of a medicament for:

(a) treating a proliferative disorder in an individual afflicted with a proliferative disorder;

(b) inhibiting the growth of tumor cells in an individual afflicted with a proliferative disorder; or (c) inducing apoptosis of cancer cells in an individual afflicted with cancer.

DETAILED DESCRIPTION OF THE INVENTION

I. Treatment of Proliferative Disorders

Figure 1:
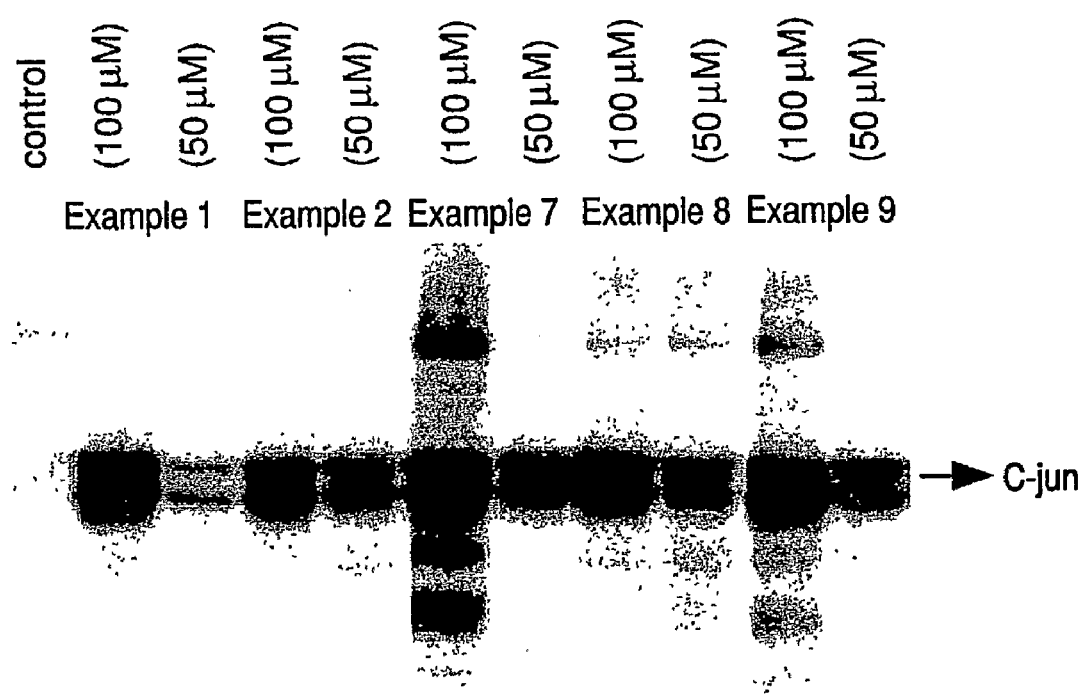
FIG. 1 shows an autoradiogram of a gel electrophoresis separation of phosphorylated GST-c-Jun which demonstrates the activation of JNK-1 by coumarin-3-sulfonamides.

According to the present invention, certain coumarin-3-sulfones and coumarin-3-sulfonamides, 2-quinolone-3-sulfones and 2-quinolone-3-sulfonamides, and thiochromen-2-one-3-sulfones and thiochromen-2-one-3-sulfonamides selectively kill various tumor cell types without killing normal cells. Without wishing to be bound by any theory, the compounds according to the present invention are believed to activate the JNK pathway, either by interacting with JNK1 or by interacting with an upstream kinase that is a part of the JNK pathway.

A. Treatment of Cancer

The compounds according to the invention may be administered to individuals (mammals, including animals and humans) afflicted with a proliferative disorder such as cancer.

The compounds according to the invention have been shown to inhibit the proliferation of tumor cells by inducing cell death. The cell-killing activity of the compounds according to the invention is selective for tumor cells over normal cells.

Cell death is believed to result from the induction of apoptosis. The compounds are believed effective against a broad range of tumor types, including but not limited to the following: ovarian cancer; cervical cancer; breast cancer; prostate cancer; testicular cancer, lung cancer, renal cancer, colorectal cancer; skin cancer; brain cancer, and leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Karposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Karposi's sarcoma, moles dysplastic nevi, lipoma, angioma, dermatofibroma, keloids, psoriasis; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

B. Treatment of Non-Cancer Proliferative Disorders

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's and Duyputren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR)

Other non-cancer proliferative disorders believed treatable by compounds according to the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time.

Treatment of tumor cells with the compounds according to the invention is believed to lead to inhibition of cell proliferation and induction of apoptotic cell death.

II. Isomerism in Compounds of the Invention

A. Geometric Isomerism

Some compounds according to Formula I are characterized by isomerism resulting from the presence of a carbon-carbon double bond. This isomerism is commonly referred to as cis-trans isomerism, but the more comprehensive naming convention employs E- and Z-designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus, if the four groups on a carbon-carbon double bond are ranked, A being the lowest rank and D being highest, A>B>C>D, the isomers would be named as in Scheme 3.

Scheme 3

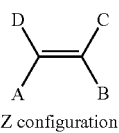
Z configuration

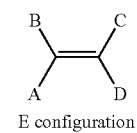
E configuration

Unless otherwise indicated, both configurations, as depicted below in Scheme 4, and mixtures thereof, are included in the scope of compounds according to Formula I.

is at least about 80%, more preferably at least 90% pure, even more preferably at least 98% pure, most preferably at least about 99% pure, by weight.

Scheme 4

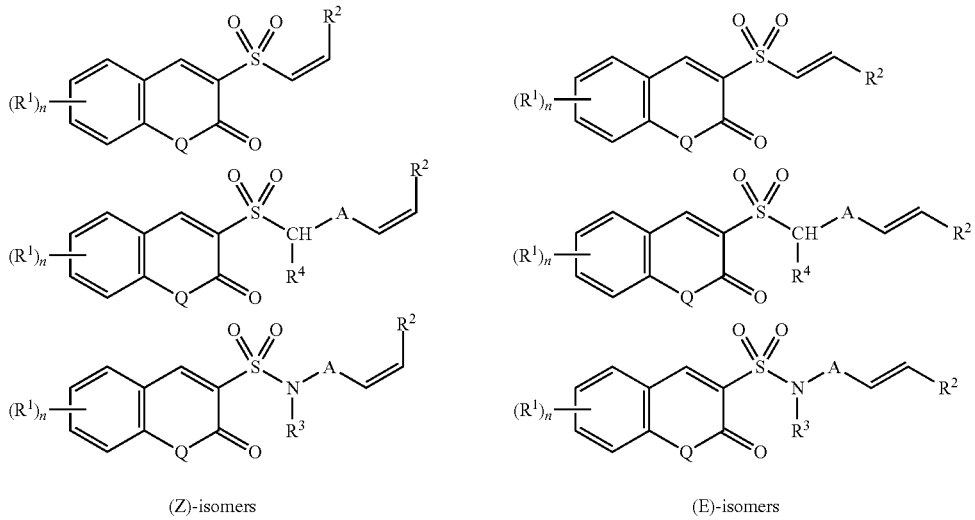

(Z)-isomers          (E)-isomers

C. Optical Isomerism

The present invention is also directed to isolated optical isomers of compounds according to Formula I. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 7, the Cahn-Ingold-Prelog ranking is A>B>C>D. The lowest ranking atom, D is oriented away from the viewer.

Scheme 5

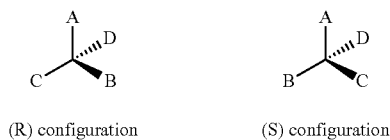

(R) configuration      (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

III. Preparation of Compounds According to the Invention

Compounds according to Formula I may be prepared via synthetic organic chemistry methods as follows.

A. Preparation of Sulfones and Sulfonamides of Formula I

Compounds of Formula I wherein M is (a):

(a)

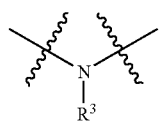

may be prepared according to the methods depicted in Scheme 6 by reacting an intermediate benzaldehyde 4, with either intermediate 2 or intermediate 3.

Scheme 6

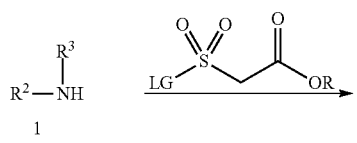

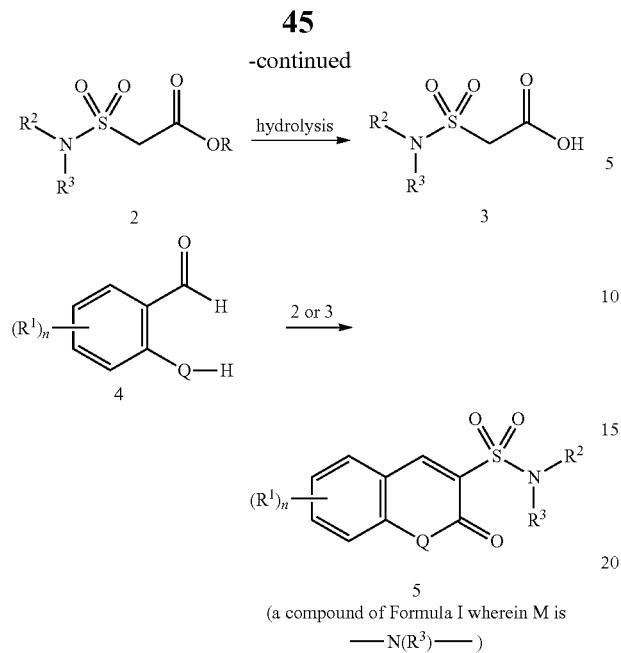

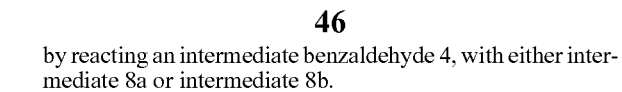

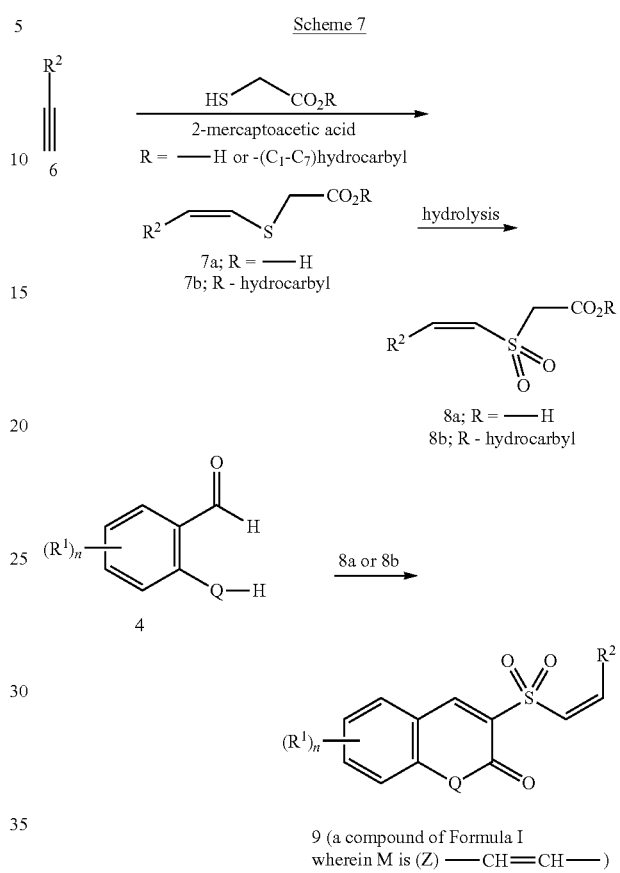

9 (a compound of Formula I wherein M is (Z) ——CH═CH——)

According to Scheme 6, a derivative of 2-sulfonylacetic acid, wherein the carboxyl group is derivatized as suitable ester (R═(C$_1$-C$_7$)hydrocarbyl) and the sulfonic acid moiety is derivatized with a suitable leaving group (LG=halogen, alkyl sulfonate, aralkyl sulfonate or haloalkyl sulfonate) may be reacted, preferably in the presence of a suitable acid scavenger, with an aromatic amine 1 to yield the corresponding methyl aromatic sulfonylacetate 2. Preferred esters of include, for example, benzyl and (C$_1$-C$_6$)alkyl esters. Preferred leaving groups LG are halogen, tosyl, mesyl and trifyl; more preferably Cl. Suitable acid scavengers include tertiary amines such as, for example, triethylamine (TEA) or diisopropylethyl amine (DIPEA). The reaction is preferably carried out in the presence of a suitable solvent. Suitable solvents include polar aprotic solvents such as, for example tetrahydrofuran (THF) or dioxane.

The intermediate aromatic sulfonylacetate ester 2 may be hydrolyzed by reaction with a suitable basic reagent, to yield the aromatic sulfonylacetic acid 3. Suitable basic reagents include hydroxides or carbonates of alkali metals or alkaline earth metals, such as, for example, LiOH, NaOH, KOH, K$_2$CO$_3$ and Na$_2$CO$_3$. The reaction is preferably carried out in the presence of a suitable aqueous solvent. Suitable aqueous solvents include water and mixtures of water with one or more water-miscible organic solvents such as, for example, acetone, methanol, ethanol or THF.

Either of the aromatic sulfonylacetic acid 3 or the aromatic sulfonylacetate ester 2 may be reacted with a substituted 2-hydroxy (or 2-amino or 2-mercapto) benzaldehyde 4 in glacial acetic acid in the presence of a catalytic amount of benzylamine to yield compound 5.

Compounds of Formula I wherein M is (b):

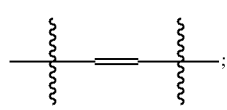

and the double bond of (b) is in the (Z)-conformation may be prepared according to the methods depicted in Scheme 7 by reacting an intermediate benzaldehyde 4, with either intermediate 8a or intermediate 8b.

According to Scheme 7, 2-mercaptoacetic acid (CAS [68-11-1], Aldrich catalog # 47,434-3), or a suitable ester thereof, may be reacted, preferably in the presence of a suitable base reagent, with an aromatic acetylene 6 to yield the corresponding (Z) α,β-unsaturated sulfide 7. Suitable esters of 2-mercaptoacetic acid include, for example, (C$_1$-C$_6$)alkyl and benzyl esters. Suitable basic reagents include hydroxides or carbonates of alkali metals or alkaline earth metals, such as, for example, LiOH, NaOH, KOH, K$_2$CO$_3$ and Na$_2$CO$_3$. The reaction is preferably carried out in the presence of a suitable solvent. Suitable solvents include polar solvents such as, for example methanol or ethanol.

The intermediate α,β-unsaturated sulfide 7 may be oxidized by reaction with a reagent capable of oxidizing a sulfide to a sulfone, to yield the (Z)-α,β-unsaturated sulfone 8. Suitable oxidizing reagents include peroxides such as hydrogen peroxide, peracids such as meta-chloroperoxybenzoic acid (MCPBA) or persulfates such as potassium peroxymonosulfate. The reaction is preferably carried out in the presence of a suitable solvent. Suitable solvents include, for example, water, acetic acid or non-polar solvents such as dichloromethane (DCM).

Either of α,β-unsaturated sulfones, 8a or 8b may be reacted with a substituted 2-hydroxy (or 2-amino or 2-mercapto) benzaldehyde 4 in glacial acetic acid in the presence of a catalytic amount of benzylamine to yield compound 9.

Compounds of Formula I wherein M is a single bond may be prepared according to the methods depicted in Scheme 8 by reacting an intermediate benzaldehyde 4, with intermediate 12.

Scheme 8

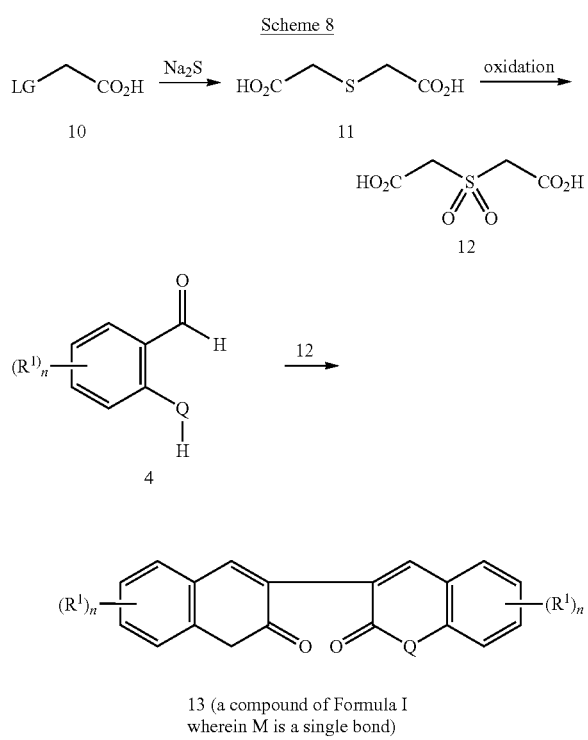

13 (a compound of Formula I wherein M is a single bond)

According to Scheme 8, an acetic acid derivative having a leaving group LG (preferably selected from halogen, alkyl sulfonate, aralkyl sulfonate or haloalkyl sulfonate) at the 2 position (preferably, 2-chloroacetic acid (CAS [79-11-8], ACROS catalog # AC10851) may be reacted with sodium sulfide to yield the corresponding dicarboxymethylsulfide, 11 (CAS [123-93-3], ACROS catalog # AC13874). The reaction is preferably carried out in the presence of a suitable solvent. Suitable solvents include polar solvents such as, for example methanol or ethanol.

The intermediate dicarboxymethylsulfide, 11 may be oxidized by reaction with a reagent capable of oxidizing a sulfide to a sulfone, to yield a dicarboxymethylsulfone, 12 (CAS [123-45-5]). Suitable oxidizing reagents include peroxides such as hydrogen peroxide, peracids such as MCPBA or persulfates such as potassium peroxymonosulfate. The reaction is preferably carried out in the presence of a suitable solvent. Suitable solvents include, for example, water and acetic acid.

Dicarboxymethylsulfone, 12 may be reacted with a substituted 2-hydroxy (or 2-amino or 2-mercapto) benzaldehyde 4 in glacial acetic acid in the presence of a catalytic amount of benzylamine to yield bis-sulfone 13. Compound 13 is shown in Scheme 8 as a symmetrical compound, however substituents $R^1$ on the heteroaryl rings are not required to be identical. The reaction may be modified to produce asymmetric products, i.e., wherein the two substituents are not identical, by employing two differently substituted aldehyde reagents 4. The reaction product will comprise a mixture of symmetrically substituted and asymmetrically substituted compounds. The product mixture may be separated by a suitable separation procedure. Suitable separation procedures include crystallization, column chromatography and preparative high performance liquid chromatography (HPLC).

Compounds of Formula I wherein M is (c):

may be prepared according to the methods depicted in Scheme 9 by reacting an intermediate benzaldehyde 4 with either intermediate 16a or intermediate 16b.

Scheme 9

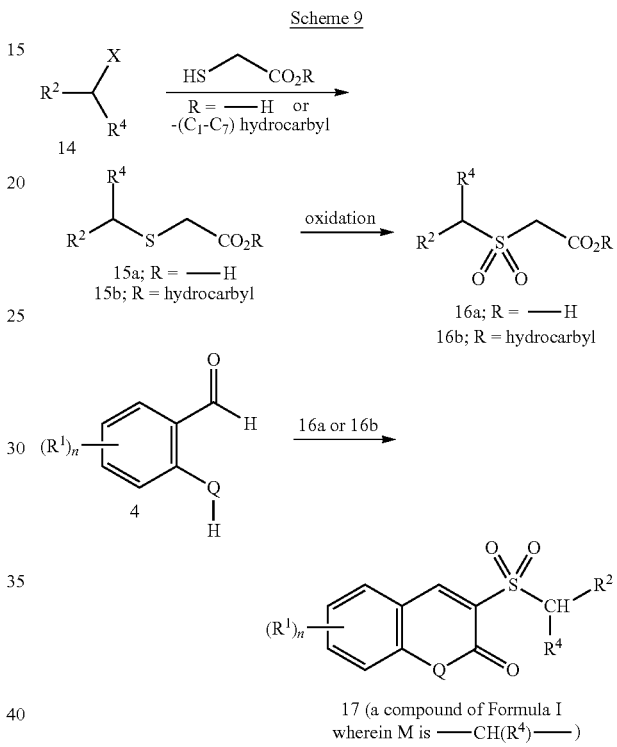

17 (a compound of Formula I wherein M is ——CH($R^4$)——)

According to Scheme 9, 2-mercaptoacetic acid, or a suitable ester thereof, may be reacted, preferably in the presence of a suitable base reagent, with an aromatic compound 14, wherein X is a suitable leaving group and $R^2$ and $R^4$ are as defined herein, to yield the corresponding sulfide 15a or 15b. Suitable esters of 2-mercaptoacetic acid include, for example, ($C_1$-$C_6$)alkyl and benzyl esters. Suitable basic reagents include hydroxides or carbonates of alkali metals or alkaline earth metals, such as, for example, LiOH, NaOH, KOH, $K_2CO_3$ and $Na_2CO_3$. The reaction is preferably carried out in the presence of a suitable solvent. Suitable solvents include polar solvents such as, for example methanol or ethanol.

The intermediate sulfide 15a or 15b may be oxidized by reaction with a reagent capable of oxidizing a sulfide to a sulfone, to yield the sulfone 16a or 16b. Suitable oxidizing reagents include peroxides such as hydrogen peroxide, peracids such as MCPBA or persulfates such as potassium peroxymonosulfate. The oxidation reaction is preferably carried out in the presence of a suitable solvent. Suitable solvents include, for example, water and acetic acid. Either of the sulfones, 16a or 16b may be reacted with a substituted 2-hydroxy (or 2-amino or 2-mercapto) benzaldehyde 4 in glacial acetic acid in the presence of a catalytic amount of benzylamine to yield the compound 17.

Compounds of Formula I wherein M is (d):

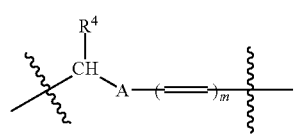

may be prepared according to the methods depicted in Scheme 10 by reacting an intermediate benzaldehyde 4, with either intermediate 20 or intermediate 21.

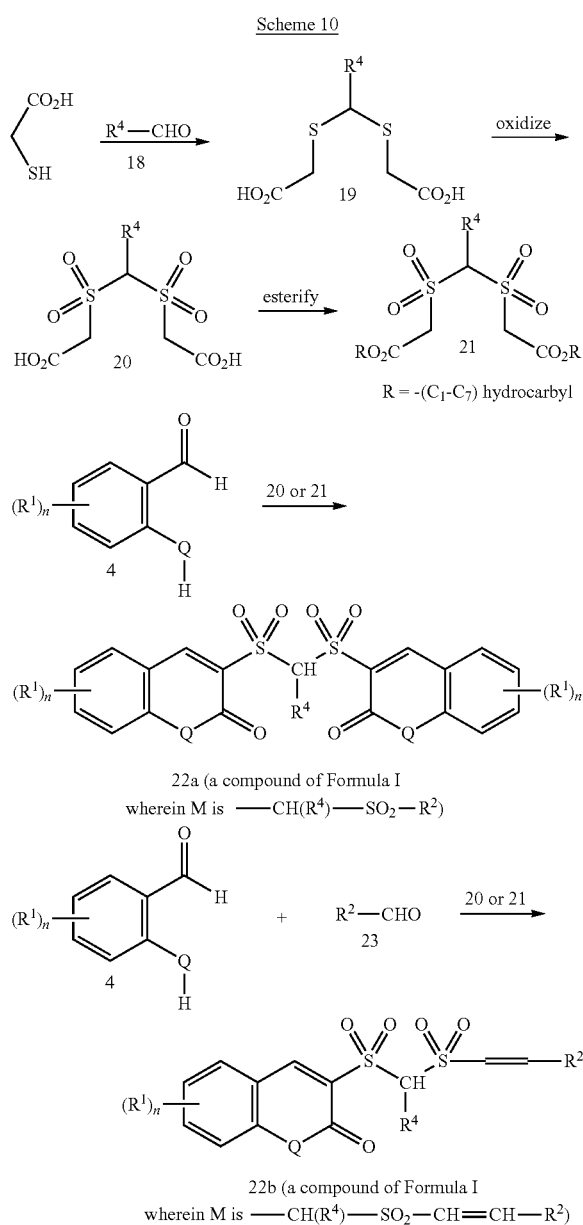

According to Scheme 10, 2-mercaptoacetic acid may be reacted, preferably in the presence of a suitable acid catalyst, with an aldehyde, 18, wherein $R^4$ is as defined herein, to yield the disulfide 19. Suitable acid catalysts include hydrochloric acid and toluenesulfonic acid. The reaction is preferably carried out in the presence of a suitable solvent. Suitable solvents include water.

The intermediate disulfide 19 may be oxidized to the corresponding disulfone 20 by reaction with a reagent capable of oxidizing a sulfide to a sulfone, to yield the disulfone 20. Suitable oxidizing reagents include peroxides such as hydrogen peroxide, peracids such as MCPBA or persulfates such as potassium peroxymonosulfate. The reaction is preferably carried out in the presence of a suitable solvent. Suitable solvents include, for example, water, acetic acid and nonpolar solvents such as DCM.

The disulfone 20 may be optionally reacted with a suitable hydrocarbyl alcohol, preferably in the presence of an acid catalyst, to form the diester, 21, wherein R is a hydrocarbyl group. Suitable hydrocarbyl alcohols include benzyl alcohols and $(C_1-C_6)$alkyl alcohols. Suitable acid catalysts for the esterification reaction include, for example, sulfuric, methane sulfonic, toluene sulfonic and hydrochloric acids.

Either of the disulfones, 20 or 21 may be reacted with a substituted 2-hydroxy (or 2-amino or 2-mercapto) benzaldehyde 4 in glacial acetic acid in the presence of a catalytic amount of benzylamine to yield bis-disulfone compound 22a. Compound 22a is shown in Scheme 10 as a symmetrical compound, however substituents $R^1$ on the two heteroaryl rings are not required to be identical. The reaction may be modified to produce asymmetric products, i.e., wherein the two $R^1$ substituents are not equivalent, by employing two differently substituted aldehyde reagents 4 in the reaction to form a mixture of symmetrically substituted and asymmetrically substituted compounds, 22a. The product mixture may be separated by a suitable separation procedure. Suitable separation procedures include crystallization, column chromatography and preparative (HPLC).

Also, as shown in Scheme 10, the asymmetric disulfone compound 22b may be prepared by reacting either of the disulfones, 20 or 21 with a combination of substituted 2-hydroxy (or 2-amino or 2-mercapto) benzaldehyde 4 and a second aromatic aldehyde 23. This reaction will form a mixture of symmetric and asymmetric disulfone compounds, of which, the asymmetric compound, 22b, is the desired product. The product mixture may be separated by a suitable separation procedure. Suitable separation procedures for isolating the compounds 22b include crystallization, column chromatography and preparative high performance liquid chromatography (HPLC).

The compounds of Formula I wherein M is (b):

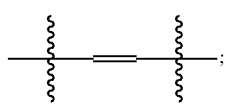

and the double bond of (b) is in the (E)-conformation may be prepared according to the methods depicted in Scheme 11 by reacting an intermediate benzaldehyde 4, with intermediate 26.

Scheme 11

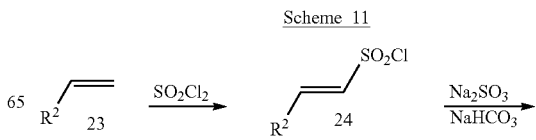

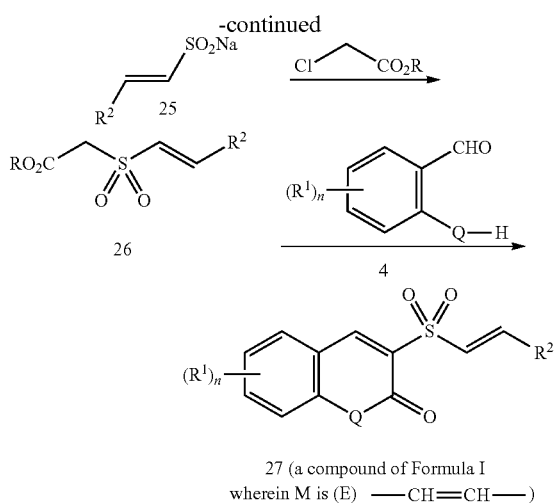

27 (a compound of Formula I
wherein M is (E) ——CH═CH——)

According to Scheme 11B, compound 23 is reacted with sulfuryl chloride (CAS [7791-25-5], Aldrich catalog # 15,776-7) to yield the corresponding (E)-α,β-unsaturated sulfonyl chloride 24. The reaction is preferably carried out in the presence of a suitable solvent. Suitable solvents include polar aprotic solvents such as, for example dimethyl formamide (DMF) or THF. The reaction is preferably carried out under anhydrous conditions in an inert atmosphere such as, for example nitrogen or argon. The reaction is preferable carried out at low temperature, such as, for example from about −20° C. to about 10° C., more preferably at about 0° C.

The intermediate (E)-α,β-unsaturated sulfonyl chloride 24 is reacted with sodium bicarbonate and sodium sulfite to yield the corresponding (E)-α,β-unsaturated sulfate salt, 25. The reaction is preferably carried out in the presence of a suitable solvent. Suitable solvents include, for example, water or mixtures of water with a water-miscible solvent such as methanol, ethanol or acetonitrile. The reaction is preferable carried out at an elevated temperature, such as, for example from about 50° C. to about 100° C., more preferably at about 90° C.

The intermediate (E)-α,β-unsaturated sulfate salt, 25 is reacted with chloroacetic acid or an ester of chloro acetic acid to yield the (E)-α,β-unsaturated sulfonyl acetate, 26. The reaction is preferably carried out in the presence of a suitable solvent. Suitable solvents include, for example, polar solvents such as methanol, ethanol or acetonitrile.

The (E)-α,β-unsaturated sulfonyl acetate, 26, either as the carboxylic acid or as an ester may be reacted with a substituted 2-hydroxy (or 2-amino or 2-mercapto) benzaldehyde 4 in glacial acetic acid in the presence of a catalytic amount of benzylamine to yield compound 27, wherein the double bond is in the (E)-conformation.

IV. Salts of Compounds According to the Invention

The compounds of the present invention may take the form of salts. The term "salts", embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, toluenesulfonic, sulfanilic, cyclohexylaminosulfonic, stearic, alginic, γ-hydroxybutyric, salicylic, galactaric and galacturonic acid. Examples of pharmaceutically unacceptable acid addition salts include, for example, perchlorates and tetrafluoroborates.

Suitable pharmaceutically-acceptable base addition salts of compounds of the invention include for example, metallic salts including alkali metal, alkaline earth metal and transition metal salts such as, for example, calcium, magnesium, potassium, sodium and zinc salts. Pharmaceutically-acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared by conventional means from the corresponding compound according to Formula I by reacting, for example, the appropriate acid or base with the compound according to Formula I.

V. Administration of Compounds of the Invention

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment.

VI. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. Higher or lower doses are also contemplated.

The practice of the invention is illustrated by the following non-limiting examples.

EXAMPLES

Examples 1-10

A. General Procedure 1: Synthesis of Coumarin-3-sulfonamide Compounds According to Formula I Method A To a round bottom flask were added a substituted anilinosulfonyl acetic acid (1 mmol), a substituted salicylaldehyde (1 mmol), acetic acid (10 mL) and benzyl amine (0.001 mmol). The resulting mixture was heated at reflux temperature for about 8-12 hours. When the reaction was complete, the mixture was allowed to cool to room temperature (22-25° C.). A solid product precipitated from the cooled mixture. The precipitate was separated by filtration and washed with isopropanol and diethyl ether to yield the desired product.

Method B

A substituted salicylaldehyde (10 mmol) was dissolved in warm (40-50° C.) absolute ethanol (20 mL). To this solution was added a substituted methyl anilinosulfonyl acetate (11 mmol) and three drops of piperidine. The resulting mixture was heated at reflux temperature for 5 min. The hot mixture was then allowed to cool to room temperature (22-25° C.). A precipitate formed in the cooled mixture. The precipitate was separated by filtration and washed three times with absolute ethanol to obtain the pure coumarin sulfonamide.

In each of the Examples 1-10, the coumarin-3-sulfonamide was made according to Method B of the General Procedure 1.

Example 1

6-Bromo-N-(4-methoxyphenyl)-2-oxo-2H-chromene-3-sulfonamide

A solution of 5-bromosalicylaldehyde (1 mmol) and 4-methoxyanilinosulfonyl acetic acid (1 mmol) in acetic acid (10 mL) was subjected to the General Procedure 1, Method A to yield the title compound; m.p. 182-184° C.

$^1$H NMR (500 MHz, DMSO): 10.24(br s, 1H), 8.71(s, 1H), 8.18(s, 1H), 7.87(d, J=9.0 Hz, 1H), 7.41(d, J=9.0 Hz, 1H), 7.04(d, J=9.0 Hz, 2H) and 6.79(d, J=7.0 Hz, 2H).

C, H, N analysis: Calculated C 46.84%; H 2.95%; N 3.41%. Found C 46.67%; H 2.74%; N 3.36%.

Example 2

6-Chloro-N-(4-methoxyphenyl)-2-oxo-2H-chromene-3-sulfonamide

A solution of 5-chlorosalicylaldehyde (1 mmol) and 4-methoxyanilinosulfonyl acetic acid (1 mmol) in acetic acid (10 mL) was subjected to the General Procedure 1, Method A to yield the title compound; m.p. 175-177° C.

$^1$H NMR (500 MHz, DMSO): 10.24(br s, 1H), 8.72(s, 1H), 8.06(s, 1H), 7.77(d, J=9.0 Hz, 1H), 7.49(d, J=9.5 Hz, 1H), 7.04(d, J=7.0 Hz, 2H) and 6.79(d, J=7.0 Hz, 2H).

C, H, N analysis: calculated C 52.54%; H 3.30%; N 3.83%. Found C 52.33%; H 3.26%; N 3.77%.

Example 3

8-Ethoxy-N-(4-methoxyphenyl)-2-oxo-2H-chromene-3-sulfonamide

A solution of 3-ethoxysalicylaldehyde (1 mmol) and 4-methoxyanilinosulfonyl acetic acid (1 mmol) in acetic acid (10 mL) was subjected to the General Procedure 1, Method A to yield the title compound; m.p. 196-198° C.

$^1$H NMR (500 MHz, DMSO): 10.18(br s, 1H), 8.71(s, 1H), 7.45(d, J=8.0 Hz, 1H), 7.40(d, J=8.0 Hz, 1H), 7.29(d, J=8.0 Hz, 1H), 7.05(d, J=7.0 Hz, 2H), 6.79(d, J=7.0 Hz, 2H), 4.13 (q, J=7.0 Hz, 2H), 3.61(s, 3H) and 1.36(t, J=6.9 Hz, 3H).

C, H, N analysis: calculated C 57.59%; H 4.56%; N 3.73%. Found C 57.33%; H 4.38%; N 3.65%.

Example 4

6-Chloro-N-(3-hydroxy-4-methoxyphenyl)-2-oxo-2H-chromene-3-sulfonamide

A solution of 5-chlorosalicylaldehyde (1 mmol) and 3-hydroxy-4-methoxyanilinosulfonyl acetic acid (1 mmol) in acetic acid (10 mL) was subjected to the General Procedure 1, Method A to yield the title compound; m.p. 225-226° C.

$^1$H NMR (400 MHz, DMSO): 10.16(br s, 1H), 9.14(s, 1H), 8.76(s, 1H), 8.12(s, 1H) 7.81(dd, J=8.8, 3.2 Hz, 1H), 7.53(d, J=8.8 Hz, 1H), 6.77(d, J=8.8 Hz, 1H), 6.65(d, J=2.5 Hz, 1H), 6.55(dd, J=8.8, 2.5 Hz, 2H) and 3.67(s, 3H).

C, H, N analysis: calculated C 50.33%; H 3.17%; N 3.67%. Found C 50.18%; H 2.95%; N 3.61%.

Example 5

N-(3-Amino-4-fluorophenyl)-8-ethoxy-2-oxo-2H-chromene-3-sulfonamide

A solution of 3-ethoxysalicylaldehyde (1 mmol) and 3-amino-4-fluoroanilinosulfonyl acetic acid (1 mmol) in acetic acid (10 mL) was subjected to the General Procedure 1, Method A to yield the title compound; m.p. 160-162° C.
$^1$H NMR (400 MHz, DMSO): 10.80(br s, 1H), 8.71(s, 1H), 7.54(d, J=7.7 Hz, 1H), 7.50(d, J=7.7 Hz, 1H), 7.42(d, J=7.7 Hz, 1H), 6.84(d, J=8.8 Hz, 1H), 6.60(d, J=8.8 Hz, 1H), 6.31 (m, 1H), 5.10 (br s, 2H), 4.28(q, J=7.0 Hz, 2H) and 1.51(t, J=6.9 Hz, 3H).

Example 6

N-(3-Amino-4-fluorophenyl)-6-methoxy-2-oxo-2H-chromene-3-sulfonamide

A solution of 5-methoxysalicylaldehyde (1 mmol) and 3-amino-4-fluoroanilinosulfonyl acetic acid (1 mmol) in acetic acid (10 mL) was subjected to the General Procedure 1, Method A to yield the title compound; m.p. 255-260° C.
$^1$H NMR (500 MHz, DMSO): 10.18(br s, 1H), 8.53(s, 1H), 7.52(d, J=2.8 Hz, 1H), 7.43(d, J=9.0 Hz, 1H), 7.33(dd, J=9.0, 2.8 Hz, 1H), 6.70(d, J=8.5 Hz, 1H), 6.47(d, J=8.5 Hz, 1H), 6.20(m, 1H), 4.79(br s, 2H) and 3.89(s, 3H).

Example 7

N-(4-Bromophenyl)-6-methoxy-2-oxo-2H-chromene-3-sulfonamide

A solution of 5-methoxysalicylaldehyde (1 mmol) and 4-bromoanilinosulfonyl acetic acid (1 mmol) in acetic acid (10 mL) was subjected to the General Procedure 1, Method A to yield the title compound; m.p. 166-168° C.
$^1$H NMR (400 MHz, DMSO): 10.88(br s, 1H), 9.02(s, 1H), 7.73(d, J=2.5 Hz, 1H), 7.60-7.50(m, 4H), 7.27(d, J=7.0 Hz, 2H) and 3.95(s, 3H); C, H, N analysis: calculated C 46.84%; H 2.95%; N 3.41%. Found C 46.70%; H 2.94%; N 3.12%.

Example 8

8-Ethoxy-N-(4-methoxyphenyl)-2-oxo-2H-chromene-3-sulfonamide

A solution of 3-ethoxysalicylaldehyde (1 mmol) and 4-methoxyanilinosulfonyl acetic acid (1 mmol) in acetic acid (10 mL) was subjected to the General Procedure 1, Method A to yield the title compound; m.p. 206-209° C.
$^1$H NMR (400 MHz, DMSO): 10.75(br s, 1H), 8.91(s, 1H), 7.52(d, J=7.6 Hz, 1H), 7.45 (d, J=8.8 Hz, 3H), 7.36(t, J=8.0 Hz, 1H), 7.13(d, J=8.0 Hz, 2H), 4.17(q, J=7.0 Hz, 2H) and 1.39(t, J=6.9 Hz, 3H); C, H, N analysis: calculated C 48.13%; H 3.32%; N 3.30%. Found C 47.60%; H 3.19%; N 3.21%.

Example 9

N-(4-Bromophenyl)-8-chloro-2-oxo-2H-chromene-3-sulfonamide

A solution of 3-chlorosalicylaldehyde (1 mmol) and 4-bromoanilinosulfonyl acetic acid (1 mmol) in acetic acid (10 mL) was subjected to the General Procedure 1, Method A to yield the title compound; m.p. 202-204° C.
$^1$H NMR (400 MHz, DMSO): 10.80(br s, 1H), 8.89(s, 1H), 8.13(s, 1H), 7.81(dd, J=8.8, 2.8 Hz, 1H), 7.51(d, J=8.8 Hz, 1H), 7.44(d, J=8.8 Hz, 2H), 7.11(d, J=8.8 Hz, 2H), 6.79(d, J=7.0 Hz, 2H), 4.13(q, J=7.0 Hz, 2H) and 1.36(t, J=6.9 Hz, 3H); C, H, N analysis: calculated C 43.45%; 11 2.19%; N 3.38%. Found C 43.39%; H 2.09%; N 3.21%.

Example 10

N-(4-Bromophenyl)-8-bromo-2-oxo-2H-chromene-3-sulfonamide

A solution of 3-bromosalicylaldehyde (1 mmol) and 4-bromoanilinosulfonyl acetic acid (1 mmol) in acetic acid (10 mL) was subjected to the General Procedure 1, Method A to yield the title compound; m.p. 206-208° C.
$^1$H NMR (400 MHz, DMSO): 10.80(br s, 1H), 8.90(s, 1H), 8.26(s, 1H), 7.93(d, J=9.0 Hz, 1H), 7.45(d, J=8.8 Hz, 3H), 7.11(d, J=8.8 Hz, 2H), 7.05(d, J=7.0 Hz, 2H), 6.79(d, J=7.0 Hz, 2H), 4.13(q, J=7.0 Hz, 2H) and 1.36(t, J=6.9 Hz, 3H).
C, H, N analysis: calculated C 39.24%; H 1.97%; N 3.05%. Found C 38.87%; H 1.89%; N 2.96%.

Examples 11-24

B. General Procedure 2: Synthesis of 3-Aromatic Methanesulfonyl Coumarin Compounds According to Formula I Method A To a round bottom flask were added a substituted benzylsulfonyl acetic acid (1 mmol), a substituted salicylaldehyde (1 mmol), acetic acid (10 mL) and benzyl amine (0.001 mmol). The resulting mixture was heated at reflux temperature for about 8-12 hours. When the reaction was complete, the mixture was allowed to cool to room temperature (22-25° C.). A solid product precipitated from the cooled mixture. The precipitate was separated by filtration and washed with isopropanol and diethyl ether to yield the desired product.

Method B

A substituted salicylaldehyde (10 mmol) was dissolved in warm (40-50° C.) absolute ethanol (20 mL). To this solution was added a substituted methyl benzylsulfonyl acetate (11 mmol) and three drops of piperidine. The resulting mixture was heated at reflux temperature for about 5 min. The hot mixture was then allowed to cool to room temperature (22-25° C.). A precipitate formed in the cooled mixture. The precipitate was separated by filtration and washed three times with absolute ethanol to obtain the pure coumarin sulfonamide.

In each of the Examples 11-24, the coumarin-3-sulfone was made according to Method B of the General Procedure 1.

Example 11

3-(4-Methoxybenzylsulfonyl)-2H-chromen-2-one

A solution of salicylaldehyde (1 mmol) and 2-(4-methoxybenzylsulfonyl)acetic acid (1 mmol) in acetic acid (10 mL) was subjected to the General Procedure 2, Method A to generate an 87.5% yield of the title compound; m.p. 194-195° C.

Example 12

3-(4-Methoxybenzylsulfonyl)-5,7-dimethoxy-2H-chromen-2-one

A solution of 4,6-dimethoxysalicylaldehyde (1 mmol) and 2-(4-methoxybenzylsulfonyl)acetic acid (1 mmol) in acetic acid (10 mL) was subjected to the General Procedure 2, Method A to generate a 58% yield of the title compound; m.p. 183-185° C.

Example 13

3-(4-Methoxybenzylsulfonyl)-6,8-dinitro-2H-chromen-2-one

A solution of 3,5-dinitrosalicylaldehyde (1 mmol) and 2-(4-methoxybenzylsulfonyl)acetic acid (1 mmol) in acetic acid (10 mL) was subjected to the General Procedure 2, Method A to yield the title compound.

Example 14

3-(4-Chlorobenzylsulfonyl)-2H-chromen-2-one

A solution of salicylaldehyde (1 mmol) and 2-(4-chlorobenzylsulfonyl)acetic acid (1 mmol) in acetic acid (10 mL) was subjected to the General Procedure 2, Method A to generate a 99% yield of the title compound; m.p. 195-196° C.

Example 15

3-(2,4-Dichlorobenzylsulfonyl)-2H-chromen-2-one

A solution of salicylaldehyde (1 mmol) and 2-(2,4-dichlorobenzylsulfonyl)acetic acid (1 mmol) in acetic acid (10 mL) was subjected to the General Procedure 2, Method A to generate an 86% yield of the title compound; m.p. 228-229° C.

Example 16

3-(4-Methoxybenzylsulfonyl)-6-bromo-2H-chromen-2-one

A solution of 5-bromosalicylaldehyde (1 mmol) and 2-(4-methoxybenzylsulfonyl)acetic acid (1 mmol) in acetic acid (10 mL) was subjected to the General Procedure 2, Method A to generate a 78% yield of the title compound; m.p. 231-232° C.

Example 17

3-(4-Methoxybenzylsulfonyl)-6-chloro-2H-chromen-2-one

A solution of 5-chlorosalicylaldehyde (1 mmol) and 2-(4-methoxybenzylsulfonyl)acetic acid (1 mmol) in acetic acid (10 mL) was subjected to the General Procedure 2, Method A to generate a 66% yield of the title compound; m.p. 224-226° C.

Example 18

3-(4-Methoxybenzylsulfonyl)-7-methoxy-2H-chromen-2-one

A solution of 4-methoxysalicylaldehyde (1 mmol) and 2-(4-methoxybenzylsulfonyl)acetic acid (1 mmol) in acetic acid (10 mL) was subjected to the General Procedure 2, Method A to generate a 43% yield of the title compound; m.p. 179-180° C.

Example 19

3-(4-Methoxybenzylsulfonyl)-7-hydroxy-2H-chromen-2-one

A solution of 4-hydroxysalicylaldehyde (1 mmol) and 2-(4-methoxybenzylsulfonyl)acetic acid (1 mmol) in acetic acid (10 mL) was subjected to the General Procedure 2, Method A to generate a 30% yield of the title compound; m.p. 231-232° C.

Example 20

3-(4-Methoxy-3-nitrobenzylsulfonyl)-5,7-dimethoxy-2H-chromen-2-one

A solution of 4,6-dimethoxysalicylaldehyde (1 mmol) and 2-(4-methoxy-3-nitrobenzylsulfonyl)acetic acid (1 mmol) in acetic acid (10 mL) was subjected to the General Procedure 2, Method A to generate a 47% yield of the title compound; m.p. 224-225° C.

Example 21

3-(4-Methoxy-3-nitrobenzylsulfonyl)-7-methoxy-2H-chromen-2-one

A solution of 4-methoxysalicylaldehyde (1 mmol) and 2-(4-methoxy-3-nitrobenzylsulfonyl)acetic acid (1 mmol) in acetic acid (10 mL) was subjected to the General Procedure 2, Method A to generate a 75% yield of the title compound; m.p. 250-252° C.

Example 22

3-(4-Methoxy-3-nitrobenzylsulfonyl)-7-hydroxy-2H-chromen-2-one

A solution of 4-hydroxysalicylaldehyde (1 mmol) and 2-(4-methoxy-3-nitrobenzylsulfonyl)acetic acid (1 mmol) in acetic acid (10 mL) was subjected to the General Procedure 2, Method A to generate a 62% yield of the title compound; m.p. 126-128° C.

Example 23

3-(4-Chloro-3-nitrobenzylsulfonyl)-6-chloro-2H-chromen-2-one

A solution of 5-chlorosalicylaldehyde (1 mmol) and 2-(4-chloro-3-nitrobenzylsulfonyl)acetic acid (1 mmol) in acetic acid (10 mL) was subjected to the General Procedure 2, Method A to generate a 93% yield of the title compound; m.p. 272-275° C.

Example 24

3-(4-Chloro-3-aminobenzylsulfonyl)-6-chloro-2H-chromen-2-one

A solution of 5-chlorosalicylaldehyde (1 mmol) and 2-(3-amino-4-chlorobenzylsulfonyl)acetic acid (1 mmol) in acetic acid (10 mL) was subjected to the General Procedure 2, Method A to generate a 91% yield of the title compound.

Examples 25-51

C. General Procedure 3: Synthesis of bis-Coumarin Sulfone Compounds According to Formula I A substituted salicylaldehyde (22 mmol) was dissolved in warm (40-50° C.) absolute ethanol (20 mL). To this solution was added sulfonyldiacetic acid methyl ester (11 mmol) and three drops of piperidine. The resulting mixture was heated at reflux temperature for about 5 min. The hot mixture was then allowed to cool to room temperature (22-25° C.). A precipitate formed in the cooled mixture. The precipitate was separated by filtration and washed three times with absolute ethanol to obtain the pure bis-coumarin sulfone.

Table 1 lists the reaction yields and the measured melting point (M.P.), for the compounds of Examples 25-51 made according to General Procedure 3.

TABLE 1

| Example #/Name | $R^1$ | $R^2$ | M.P. (° C.) | Yield (%) |
|---|---|---|---|---|
| Example 25: 6-bromo-3-[(6-bromo-2-oxochromen-3-yl)sulfonyl]chromen-2-one | 6-Br | 6-Br-coumarin-3-yl | 320-22 | 90.3 |
| Example 26: 6-chloro-3-[(6-chloro-2-oxochromen-3-yl)sulfonyl]chromen-2-one-bis-(2H-chromene-2-one-3-yl)sulfone | 6-Cl | 6-Cl-coumarin-3-yl | 322-25 | 87.5 |
| Example 27: (2-oxochromen-3-yl)sulfonyl]-chromen-2-one (or bis-(2H-chromene-2-one-3-yl)sulfone) | —H | coumarin-3-yl | 316-18 | 77.2 |
| Example 28: 8-ethoxy-3-[(8-ethoxy-2-oxochromen-3-yl)sulfonyl]chromen-2-one; | 8-OEt | 8-OEt-coumarin-3-yl | 276-78 | 94 |
| Example 29: 3-[(5,7-dimethoxy-2-oxochromen-3-yl)-sulfonyl]-5,7-dimethoxychromen-2-one | 5,7-OMe | 5,7-di-OMe-coumarin-3-yl | 322-24 | 78 |
| Example 30: 7-methoxy-3-[(7-methoxy-2-oxo-chromen-3-yl)sulfonyl]chromen-2-one | 7-OMe | 7-OMe-coumarin-3-yl | 324-28 | 76.1 |
| Example 31: 5-methoxy-3-[(5-methoxy-2-oxo-chromen-3-yl)sulfonyl]chromen-2-one | 5-OMe | 5-OMe-coumarin-3-yl | 318-22 | 86.3 |
| Example 32: 6-fluoro-3-[(6-fluoro-2-oxochromen-3-yl)sulfonyl]chromen-2-one | 6-F | 6-fluoro-coumarin-3-yl | 306-08 | 91.4 |
| Example 33: 6-iodo-3-[(6-iodo-2-oxochromen-3-yl)sulfonyl]chromen-2-one | 6-I | 6-I-coumarin-3-yl | 354-58 | 83.3 |
| Example 34: 6-nitro-3-[(6-nitro-2-oxo-chromen-3-yl)sulfonyl]chromen-2-one | 6-NO$_2$ | 6-NO$_2$-coumarin-3-yl | >380 (dec) | 76 |
| Example 35: 8-methoxy-3-[(8-methoxy-6-nitro-2-oxo-chromen-3-yl)sulfonyl]-6-nitro-chromen-2-one | 6-NO$_2$-8-OMe | 6-NO$_2$-8-OMe-coumarin-3-yl | 358-61 | 81 |
| Example 36: 7-hydroxy-3-[(7-hydroxy-2-oxo-chromen-3-yl)sulfonyl]chromen-2-one | 7-OH | 7-OH-coumarin-3-yl | 262-64 | 79 |
| Example 37: 6,8-dinitro-3-[(6,8-dinitro-2-oxochromen-3-yl)sulfonyl]chromen-2-one | 6,8-NO$_2$ | 6,8-di-NO$_2$-coumarin-3-yl | 312-14 | 78.7 |
| Example 38: 6-methoxy-3-[(6-methoxy-2-oxochromen-3-yl)sulfonyl]chromen-2-one | 6-OMe | 6-OMe-coumarin-3-yl | 308-10 | 76.1 |
| Example 39: 8-methyl-3-[(8-methyl-2-oxochromen-3-yl)sulfonyl]chromen-2-one | 8-CH$_3$ | 8-CH$_3$-coumarin-3-yl | 338-40 | 93.4 |
| Example 40: 5-methyl-3-[(5-methyl-2-oxo-chromen-3-yl)sulfonyl]chromen-2-one | 5-CH$_3$ | 5-CH$_3$-coumarin-3-yl | 282-84 | 90.7 |
| Example 41: [(2-oxobenzo[g]chromen-3-yl)sulfonyl]benzo[g]chromen-2-one | 6,7-benzo (fused) | 2-oxobenzo[g]-chromen-3-yl) | >372 | 69.4 |
| Example 42: 6-trifluoromethoxy-3-[(6-tri-fluoromethoxy-2-oxochromen-3-yl)-sulfonyl]chromen-2-one | 6-OCF$_3$ | 6-OCF$_3$-coumarin-3-yl | 250-52 | 64.5 |
| Example 43: 6,8-dichloro-3-[(6,8-dichloro-2-oxochromen-3-yl)sulfonyl]chromen-2-one | 6,8-Cl | 6,8-di-Cl-coumarin-3-yl | 278-80 | 58.1 |
| Example 44: 6,8-dibromo-3-[(6,8-bromo-2-oxochromen-3-yl)sulfonyl]chromen-2-one | 6,8-Br | 6,8-di-Br-coumarin-3-yl | 288-90 | 70.3 |
| Example 45: 6,8-fluoro-3-[(6,8-fluoro-2-oxochromen-3-yl)sulfonyl]chromen-2-one | 6,8-F | 6,8-di-F-coumarin-3-yl | 320-2 | 55.2 |
| Example 46: 5-bromo-8-methoxy-3-[(5-bromo-8-methoxy-2-oxochromen-3-yl)sulfonyl]chromen-2-one | 5-Br-8-OMe | 5-Br-8-OMe-coumarin-3-yl | >376 | 91.2 |
| Example 47: 6-bromo-8-methoxy-3-[(6-bromo-8-methoxy-2-oxochromen-3-yl)sulfonyl]chromen-2-one | 6-Br-8-OMe | 6-Br-8-OMe-coumarin-3-yl | 358-60 | 86.8 |

TABLE 1-continued

| Example #/Name | R¹ | R² | M.P. (° C.) | Yield (%) |
|---|---|---|---|---|
| Example 48: 6-chloro-8-bromo-3-[(6-chloro-8-bromo-2-oxochromen-3-yl)sulfonyl]-chromen-2-one | 6-Cl-8-Br | 6-Cl-8-Br-coumarin-3-yl | 284-86 | 68 |
| Example 49: 8-hydroxy-3-[(8-hydroxy-2-oxochromen-3-yl)sulfonyl]chromen-2-one | 8-OH | 8-OH-coumarin-3-yl | 240-42 | 89.3 |
| Example 50: 6-hydroxy-3-[(6-hydroxy-2-oxochromen-3-yl)sulfonyl]chromen-2-one | 6-OH | 6-OH-coumarin-3-yl | 256-58 | 57.7 |
| Example 51: 6-amino-3-[(6-amino-2-oxochromen-3-yl)sulfonyl]chromen-2-one | 6-NH₂ | 6-NH₂-coumarin-3-yl | 280-82 | 57.7 |

Examples 52-61

D. General Procedure 4: Synthesis of bis-Coumarin Sulfone Methylene Compounds According to Formula I A substituted salicylaldehyde (22 mmol) was dissolved in warm (40-50° C.) absolute ethanol (20 mL). To this solution was added methylene bis(sulfonylacetic acid methyl ester) (11 mmol) and three drops of piperidine. The resulting mixture was heated at reflux temperature for about 5 min. The hot mixture was then allowed to cool to room temperature (22-25° C.). A precipitate formed in the cooled mixture. The precipitate was separated by filtration and washed three times with absolute ethanol to obtain the pure bis-coumarin sulfone methylene compound.

Table 2 lists the reaction yields and the measured melting point (M.P.), for the compounds of Examples 52-61 made according to General Procedure 4.

TABLE 2

| Example #/Name | R¹ | R² | M.P. (° C.) | Yield (%) |
|---|---|---|---|---|
| Example 52: (2-oxo-chromen-3-yl-sulfonyl)-methyl}-sulfonyl)chromen-2-one | —H | coumarin-3-yl | 348-50 | 58 |
| Example 53: 6-chloro-3-({[(6-chloro-2-oxochromen-3-yl)sulfonyl]methyl}sulfonyl)-chromen-2-one | 6-Cl | 6-chloro-coumarin-3-yl | 337-38 | 67 |
| Example 54: 6-bromo-3-({[(6-bromo-2-oxochromen-3-yl)sulfonyl]methyl}sulfonyl)-chromen-2-one | 6-Br | 6-bromo-coumarin-3-yl | 346-47 | 69 |
| Example 55: 6-iodo-3-({[(6-iodo-2-oxochromen-3-yl)-sulfonyl]methyl}sulfonyl)chromen-2-one | 6-I | 6-iodo-coumarin-3-yl | 245-47 | 73 |
| Example 56: 8-ethoxy-3-({[(8-ethoxy-2-oxo-chromen-3-yl)sulfonyl]methyl}sulfonyl)-chroman-2-one | 8-OEt | 8-ethoxy-coumarin-3-yl | 288-90 | 77 |
| Example 57: 3-({[(5,7-dimethoxy-2-oxochromen-3-yl)-sulfonyl]methyl}sulfonyl)-5,7-dimethoxy-chromen-2-one | 5,7-OMe | 5,7-di-methoxy-coumarin-3-yl | 338-40 | 72 |
| Example 58: 7-methoxy-3-({[(7-methoxy-2-oxo-chromen-3-yl)sulfonyl]methyl}sulfonyl)-chromen-2-one | 7-OMe | 7-methoxy-coumarin-3-yl | 348-50 | 62 |
| Example 59: 5-methoxy-3-({[(5-methoxy-2-oxo-chromen-3-yl)sulfonyl]methyl}sulfonyl)-chromen-2-one | 5-MeO | 5-methoxy-coumarin-3-y | 375-77 | 71 |
| Example 60: 7-hydroxy-3-({[(7-hydroxy-2-oxo-chromen-3-yl)sulfonyl]methyl}sulfonyl)-chromen-2-one | 7-OH | 7-hydroxy-coumarin-3-yl | 255-57 | 80 |
| Example 61: 3-({[(6,8-dinitro-2-oxochromen-3-yl)-sulfonyl]methyl}sulfonyl)-6,8-dinitro-chromen-2-one | 6,8-NO₂ | 6,8-dinitro-coumarin-3-yl | Not done | |

Example 62

Effect of Compounds of Formula I on Tumor Cell Lines

A. Cells

The effect of compounds according to Formula I on the growth of human tumor cells in culture was evaluated using androgen receptor negative prostate (DU145), colo-rectal (DLD-1), non-small cell lung carcinoma (H157), estrogen receptor negative breast (BT20) and chronic myeloid leukemia (K562) cell lines. All cell cultures were maintained at 37° C. in a humidified atmosphere of 5% $CO_2$.

B. Treatment of Cells with Compounds According to Formula I

Cells were treated with compounds according to Formula I at five different concentrations (1-100 µM range) for each compound. The dose response of each cell line was established by determining the number of viable cells after 96 h of continuous treatment against each of the different test concentrations of each compound. The determination of viable cells was done by the by the Trypan blue exclusion method. Activity for each compound at each concentration is reported as a percentage of cells that remain viable.

Table 3 shows the $GI_{50}$ values, i.e., the concentration of each compound required to inhibit the growth of each tumor cell line by 50%, determined for each tested compound.

TABLE 3

| Ex. # | $R^2$ | $R^1$ | Cell Line ($GI_{50}$ µM)[a] | | | | |
|---|---|---|---|---|---|---|---|
| | | | BT20 | DU145 | H157 | DLD-1 | K562 |
| 1 | 4-OMe phenyl | 6-Br | 16 | 15 | 18 | 20 | 14 |
| 2 | 4-OMe phenyl | 6-Cl | 27 | 22 | 28 | 32 | 23 |
| 3 | 4-OMe phenyl | 8-OEt | 52 | 57 | 74 | 78 | 48 |
| 4 | 4-OMe, 3-OH phenyl | 6-Cl | 65 | 42 | 76 | 82 | 51 |
| 5 | 4-F, 3-$NH_2$ phenyl | 8-OEt | 54 | 48 | 72 | 80 | 42 |
| 6 | 4-F, 3-$NH_2$ phenyl | 6-OMe | 68 | 56 | 78 | 92 | 44 |
| 7 | 4-OMe phenyl | 6-OMe | 18 | 25 | 32 | 38 | 27 |
| 8 | 4-Br phenyl | 8-OEt | 64 | 52 | 74 | 85 | 58 |
| 9 | 4-Br phenyl | 8-Cl | 17 | 14 | 16 | 18 | 11 |
| 10 | 4-Br phenyl | 8-Br | 12 | 12 | 15 | 14 | 16 |

Example 63

Effect of Compounds of Formula I on Activation of Jun Kinase

The compounds of Examples 1, 2, 7, 8 and 9 from Table 3 were analyzed for activation of the Jun kinase signaling pathway. The selected compounds were added to BT-20 cells at concentrations of 50 and 100 µM in dimethyl sulfoxide (DMSO) and incubated for 12 hours at 37° C. The cells were harvested and lysed after 12 hours of treatment. The cell lysates were then analyzed for c-Jun kinase activity by immunoprecipitating JNK1 and assessing the ability of these immunoprecipitates to phosphorylate GST-linked c-Jun. Lysis of the cells was performed after incubation with Following the incubation with the compound, using the lysis buffer [25 mM N-2-hydroxyethylpiperazine-N'-2-ethanesulfonic acid (HEPES) (pH 7.6), 0.1% Triton, 300 mM NaCl, 20 mM β-glycerophosphate, 1.5 mM $MgCl_2$, 0.2 mM ethylenediaminetetraacetic acid (EDTA), 0.5 mM dithiothreitol (DTT), 0.2 mM $Na_3VO_4$, 100 µM phenylmethylsulfonyl fluoride (PMSF), 1 mM benzamidine, 2 µg/mL leupeptin and 4 µg/mL aprotinin]. Protein concentrations were measured using Bio-Rad protein assay reagent. JNK1 in 100 µg of cell lysate was immunoprecipitated by incubating 100 mg of lysate protein with 1 mg of the JNK1 polyclonal antibody (Santa Cruz Biotechnology, Inc.,) for 1 h followed by an additional incubation with 20 mL of protein A-Sepharose (Pharmacia) for 1 h. The immune complex bound protein A-Sepharose beads were washed twice with the lysis buffer and twice with JNK buffer (20 mM HEPES, pH 7.6, 20 mM β-glycerophosphate, 10 mM $MgCl_2$ and 100 mM $Na_3VO_4$. The kinase reaction was carried out by resuspending the complex bound protein A-Sepharose beads in 40 mL of JNK buffer containing 20 mM [γ-$^{32}$P]ATP (5000 CPM/pmol) and incubating them for 20 min at 30° C. using 5 mg GST-c-Jun as substrate. The reaction was terminated by the addition of Laemmli's buffer. The samples were then boiled for 3 min. The phosphorylated GST-c-Jun was then separated on 12% SDS-PAGE. Following the separation, the gel was dried, and an autoradiogram was developed which is reproduced in FIG. 1. Results from these studies, as shown in FIG. 1, demonstrate that GST-c-Jun is hyperphosphorylated in all the cells that were treated with compounds according to Formula I compared to the controls which were treated with DMSO alone.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:
1. A compound according to Formula I:

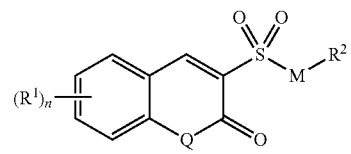

wherein:
each Q is independently O, or S;
each $R^1$ is independently selected from the group consisting of halogen, —$(C_1$-$C_8)$hydrocarbyl, —(=O)$R^y$, —$NR^w{}_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)(O$R^w$)$_2$, —O($C_2$-$C_6$)alkylene-N(CH$_3$)$_2$, —O($C_1$-$C_6$)haloalkyl, —P(=O)(O$R^w$)$_2$, —NHC(=NH)NH$R^x$, —$(C_1$-$C_6)$haloalkyl and heteroalkyl;
wherein two hydrocarbyl $R^1$ groups on adjacent carbon atoms of the phenyl ring of I may combine to form a phenyl ring fused to the compound of Formula I at the 5-6, the 6-7, or the 7-8 bond;
$R^w$ is —$(C_1$-$C_8)$hydrocarbyl;

$R^x$ is —H, —($C_1$-$C_8$)hydrocarbyl or —C(=O)($C_1$-$C_8$)hydrocarbyl;

$R^y$ is selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —($C_2$-$C_{10}$)heteroalkyl, —($C_1$-$C_6$)haloalkyl, —CH($R^z$)$NHR^x$, —N($R^w$)$R^x$, —($C_1$-$C_3$)alkylene$NH_2$, —($C_1$-$C_3$)alkyleneN($CH_3$)$_2$, —($C_1$-$C_3$)perfluoroalkyleneN($CH_3$)$_2$, —($C_1$-$C_3$)alkyleneN$^+$(($C_1$-$C_3$)alkyl)$_3$, —($C_1$-$C_3$)alkylene-N$^+$($CH_2CH_2OH$)$_3$, —($C_1$-$C_3$)alkylene-$OR^x$, —($C_1$-$C_4$)alkylene-$CO_2R^x$, —($C_1$-$C_4$)alkylene-$CO_2N(R^w)R^x$, —($C_1$-$C_4$)alkylene-C(=O)halogen, halo($C_1$-$C_3$)alkyl and —($C_1$-$C_4$)perfluoroalkylene-$CO_2R^x$;

$R^z$ is selected from the group consisting of —H, —($C_1$-$C_6$)alkyl, —($CH_2$)$_3$—NH—C($NH_2$)(=NH), —$CH_2$C(=O)$NH_2$, —$CH_2COOH$, —$CH_2SH$, —($CH_2$)$_2$C(=O)—$NH_2$, —($CH_2$)$_2CO_2H$, —$CH_2$-(2-imidazolyl), —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl) and —$CH_2$-(4-hydroxyphenyl);

each n is independently selected from the group consisting of 1, 2, 3 and 4;

M is selected from the group consisting of (a), (b), (c), (d) and (e):

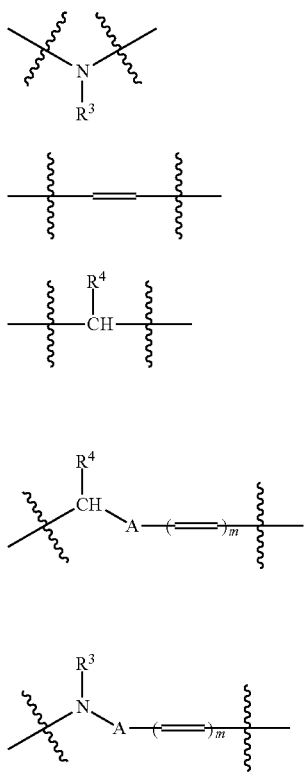

$R^2$ is substituted or unsubstituted aryl;

$R^3$ and $R^4$ are independently selected from the group consisting of —H and —($C_1$-$C_6$)alkyl;

A is —$SO_2$— or —C(=O)—; and m is 1;

provided that:
(i) when Q is O and M is:

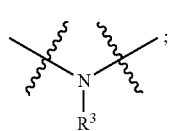

then $R^1$ is other than —$NO_2$;
or a salt thereof.

2. A compound according to claim 1, or a salt thereof, wherein the salt is a pharmaceutically acceptable salt.

3. A compound according to claim 1, or a salt thereof, wherein the compound is an isolated compound.

4. A compound according to claim 1, or a salt thereof, wherein $R^2$ is substituted or unsubstituted phenyl.

5. A compound according to claim 1, or a salt thereof, wherein Q is O.

6. A compound according to claim 5, or a salt thereof, wherein $R^2$ is substituted or unsubstituted phenyl.

7. A compound according to claim 6, or a salt thereof, wherein M is (a):

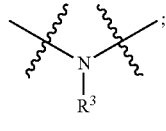

and
each $R^1$ is independently selected from the group consisting of halogen, —($C_1$-$C_8$)hydrocarbyl, —C(=O)$R^y$, —$NR^w_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)(O$R^w$)$_2$, —O($C_2$-$C_6$)alkylene-N($CH_3$)$_2$, —($C_1$-$C_6$)haloalkyl, —P(=O)(O$R^w$)$_2$, —NHC(=NH)$NHR^x$, —($C_1$-$C_6$)haloalkyl and heteroalkyl.

8. A compound according to claim 7 selected from the group consisting of:
6-bromo-N-(4-methoxyphenyl)-2-oxo-2H-chromene-3-sulfonamide; 6-chloro-N-(4-methoxyphenyl)-2-oxo-2H-chromene-3-sulfonamide; 8-ethoxy-N-(4-methoxyphenyl)-2-oxo-2H-chromene-3-sulfonamide; 6-chloro-N-(3-hydroxy-4-methoxyphenyl)-2-oxo-2H-chromene-3-sulfonamide; N-(3-amino-4-fluorophenyl)-8-ethoxy-2-oxo-2H-chromene-3-sulfonamide; N-(3-amino-4-fluorophenyl)-6-methoxy-2-oxo-2H-chromene-3-sulfonamide; N-(4-bromophenyl)-6-methoxy-2-oxo-2H-chromene-3-sulfonamide; 8-ethoxy-N-(4-methoxyphenyl)-2-oxo-2H-chromene-3-sulfonamide; N-(4-bromophenyl)-8-chloro-2-oxo-2H-chromene-3-sulfonamide; N-(4-bromophenyl)-8-bromo-2-oxo-2H-chromene-3-sulfonamide; and salts thereof.

9. A compound according to claim 6 wherein M is (b):

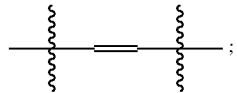

or a salt of such a compound.

10. A compound according to claim 9 selected from the group consisting of:

3-(E)-(4-methoxystyrylsulfonyl)-6-bromo-2H-chromen-2-one; 3-(E)-(4-chlorostyrylsulfonyl)-6-bromo-2H-chromen-2-one; 3-(E)-(2,4-dichlorostyrylsulfonyl)-6-bromo-2H-chromen-2-one; 3-(E)-(4-methoxystyrylsulfonyl)-6-chloro-2H-chromen-2-one; 3-(E)-(4-chlorostyrylsulfonyl)-6-chloro-2H-chromen-2-one; 3-(E)-(2,4-dichlorostyrylsulfonyl)-6-chloro-2H-chromen-2-one; 3-(E)-(4-methoxystyrylsulfonyl)-5,7-dimethoxy-2H-chromen-2-one; 3-(E)-(4-chlorostyrylsulfonyl)-5,7- dimethoxy-2H-chromen-2-one; 3-(E)-(2,4-dichlorostyrylsulfonyl)-5,7-dimethoxy-2H-chromen-2-one; 3-(E)-(4-methoxystyrylsulfonyl)-7-methoxy-2H-chromen-2-one; 3-(E)-(4-chlorostyrylsulfonyl)-7-methoxy-2H-chromen-2-one; 3-(E)-(2,4-dichlorostyrylsulfonyl)-7-methoxy-2H-chromen-2-one; 3-(Z)-(4-methoxystyrylsulfonyl)-6-bromo-2H-chromen-2-one; 3-(Z)-(4-chlorostyrylsulfonyl)-6-bromo-2H-chromen-2-one; 3-(Z)-(2,4-dichlorostyrylsulfonyl)-6-bromo-2H-chromen-2-one; 3-(Z)-(4-methoxystyrylsulfonyl)-6-chloro-2H-chromen-2-one; 3-(Z)-(4-chlorostyrylsulfonyl)-6-chloro-2H-chromen-2-one; 3-(Z)-(2,4-dichlorostyrylsulfonyl)-6-chloro-2H-chromen-2-one; 3-(Z)-(4-methoxystyrylsulfonyl)-5,7-dimethoxy-2H-chromen-2-one; 3-(Z)-(4-chlorostyrylsulfonyl)-5,7- dimethoxy-2H-chromen-2-one; 3-(Z)-(2,4-dichlorostyrylsulfonyl)-5,7-dimethoxy-2H-chromen-2-one; 3-(Z)-(4-methoxystyrylsulfonyl)-7-methoxy-2H-chromen-2-one; 3-(Z)-(4-chlorostyrylsulfonyl)-7-methoxy-2H-chromen-2-one; 3-(Z)-(2,4-dichlorostyrylsulfonyl)-7-methoxy-2H-chromen-2-one; and salts thereof.

11. A compound according to claim 6 wherein M is (c):

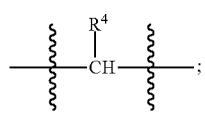

(c)

or a salt of such a compound.

12. A compound according to claim 11 selected from the group consisting of:

3-(4 methoxybenzylsulfonyl)-5,7-dimethoxy-2H-chromen-2-one; 3-(4-methoxybenzylsulfonyl)-6,8-dinitro-2H-chromen-2-one; 3-(4-methoxybenzylsulfonyl)-6-bromo-2H-chromen-2-one; 3-(4-methoxybenzylsulfonyl)-6-chloro-2H-chromen-2-one; 3-(4-methoxybenzylsulfonyl)-7-methoxy-2H-chromen-2-one; 3-(4-methoxybenzylsulfonyl)-7-hydroxy-2H-chromen-2-one; 3-(4-methoxy-3-nitrobenzylsulfonyl)-5,7-dimethoxy-2H-chromen-2-one; 3-(4-methoxy-3-nitrobenzylsulfonyl)-7-methoxy-2H-chromen-2-one; 3-(4-chloro-3-nitrobenzylsulfonyl)-6-chloro-2H-chromen-2-one; 3-(4-chloro-3-aminobenzylsulfonyl)-6-chloro-2H-chromen-2-one; and salts thereof.

13. A compound according to claim 5 wherein M is (d) or (e):

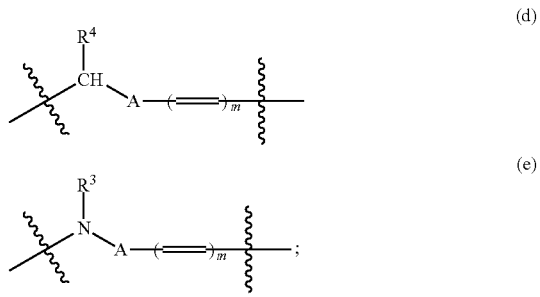

or a salt of such a compound.

14. A compound according to claim 13 selected from the group consisting of:

3-(E)-((4-methoxystyrylsulfonyl)methylsulfonyl)-7-chloro-2H-chromen-2-one; 3-(E)-((4-methoxystyrylsulfonyl)methylsulfonyl)-6-chloro-2H-chromen-2-one; 3-(E)-((4-methoxystyrylsulfonyl)methylsulfonyl)-6-bromo-2H-chromen-2-one; 3-(E)-((4-methoxystyrylsulfonyl)methylsulfonyl)-7-iodo-2H-chromen-2-one; 3-(E)-((4-methoxystyrylsulfonyl)methylsulfonyl)-8-ethoxy-2H-chromen-2-one; 3-(E)-((4-methoxystyrylsulfonyl)methylsulfonyl)-7-methoxy-2H-chromen-2-one; 3-(E)-((4-methoxystyrylsulfonyl)methylsulfonyl)-5-methoxy-2H-chromen-2-one; 3-(E)-((4-methoxystyrylsulfonyl)methylsulfonyl)-5,7-dimethoxy-2H-chromen-2-one; 3-(Z)-((4-methoxystyrylsulfonyl)methylsulfonyl)-7-chloro-2H-chromen-2-one; 3-(Z)-((4-methoxystyrylsulfonyl)methylsulfonyl)-6-chloro-2H-chromen-2-one; 3-(Z)-((4-methoxystyrylsulfonyl)methylsulfonyl)-6-bromo-2H-chromen-2-one; 3-(Z)-((4-methoxystyrylsulfonyl)methylsulfonyl)-7-iodo-2H-chromen-2-one; 3-(Z)-((4-methoxystyrylsulfonyl)methylsulfonyl)-8-ethoxy-2H-chromen-2-one; 3-(Z)-((4-methoxystyrylsulfonyl)methylsulfonyl)-7-methoxy-2H-chromen-2-one; 3-(Z)-((4-methoxystyrylsulfonyl)methylsulfonyl)-5-methoxy-2H-chromen-2-one; 3-(Z)-((4-methoxystyrylsulfonyl)methylsulfonyl)-5,7 -dimethoxy-2H-chromen-2-one; 3-((E)-4-(4-methoxyphenyl)-2-oxobut-3-enylsulfonyl)-7-chloro-2H-chromen-2-one, 3-((E)-4-(4-methoxyphenyl)-2-oxobut-3-enylsulfonyl)-6-chloro-2H-chromen-2-one; 3-((E)-4-(4-methoxyphenyl)-2-oxobut-3-enylsulfonyl)-6-bromo-2H-chromen-2-one; 3-((E)-4-(4-methoxyphenyl)-2-oxobut-3-enylsulfonyl)-6-iodo-2H-chromen-2-one; 3-((E)-4-(4-methoxyphenyl)-2-oxobut-3-enylsulfonyl)-8-ethoxy-2H-chromen-2-one; 3-((E)-4-(4-methoxyphenyl)-2-oxobut-3-enylsulfonyl)-7-methoxy-2H-chromen-2-one; 3-((E)-4-(4-methoxyphenyl)-2-oxobut-3-enylsulfonyl)-5-methoxy-2H-chromen-2-one; 3-((E)-4-(4-methoxyphenyl)-2-oxobut-3-enylsulfonyl)-5,7-dimethoxy-2H-chromen-2-one; 3-((Z)-4-(4-methoxyphenyl)-2-oxobut-3-enylsulfonyl)-7-chloro-2H-chromen-2-one, 3-((Z)-4-(4-methoxyphenyl)-2-oxobut-3-enylsulfonyl)-6-chloro-2H-chromen-2-one; 3-((Z)-4-(4-methoxyphenyl)-2-oxobut-3-enylsulfonyl)-6-bromo-2H-chromen-2-one; 3-((Z)-4-(4-methoxyphenyl)-2-oxobut-3-enylsulfonyl)-6-iodo-2H-chromen-2-one; 3-((Z)-4-(4-methoxyphenyl)-2-oxobut-3-enylsulfonyl)-8-ethoxy-2H-chromen-2-one; 3-((Z)-4-(4-methoxyphenyl)-2-oxobut-3-enylsulfonyl)-7-methoxy-2H-chromen-2-one; 3-((Z)-4-(4-methoxyphenyl)-2-oxobut-3-enylsulfonyl)-5-methoxy-2H-chromen-2-one; 3-((Z)-4-(4-methoxyphenyl)-2-oxobut-3-enylsulfonyl)-5,7-dimethoxy-2H-chromen-2-one; and salts thereof.

15. A compound according to claim 1, or a salt thereof, wherein Q is S.

16. A compound according to claim 15, or a salt thereof, wherein M is (a):

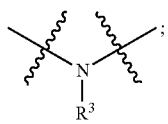
(a)

and each $R^1$ is independently selected from the group consisting of halogen, —$(C_1$-$C_8)$hydrocarbyl, —C(=O)$R^y$, —$NR^w_2$, —$N(R^w)C(=O)R^y$, —$N(R^w)CH(R^z)C(=O)R^y$, —$N(R^w)SO_2R^y$, —$N(R^w)(C_1$-$C_4)$alkylene-$CO_2R^w$, —CN, —$OR^w$, —OC(=O)$R^y$, —OCH($R^z$)C(=O)$R^y$, —$OSO_2R^y$, —O($C_1$-$C_4$)alkylene-$CO_2R^w$, —OP(=O)($OR^w)_2$, —O($C_2$-$C_6$)alkylene-N($CH_3)_2$, —O($C_1$-$C_6$)haloalkyl, —P(=O)($OR^w)_2$, —NHC(=NH)$NHR^x$, —($C_1$-$C_6$)haloalkyl and heteroalkyl.

17. A compound according to claim 16 selected from the group consisting of:

7-chloro-N-(4-methoxyphenyl)-2-oxo-2H-thiochromene-3-sulfonamide; 7-chloro-N-(3-hydroxy-4-methoxyphenyl)-2-oxo-2H-thiochromene-3-sulfonamide; 7-chloro-N-(3-amino-4-fluorophenyl)-2-oxo-2H-thiochromene-3-sulfonamide; 7-chloro-N-(4-bromophenyl)-2-oxo-2H-thiochromene-3-sulfonamide; 6-bromo-N-(4-methoxyphenyl)-2-oxo-2H-thiochromene-3-sulfonamide 6-chloro-N-(4-methoxyphenyl)-2-oxo-2H-thiochromene-3-sulfonamide; 8-ethoxy-N-(4-methoxyphenyl)-2-oxo-2H-thiochromene-3-sulfonamide; 6-chloro-N-(3-hydroxy-4-methoxyphenyl)-2-oxo-2H-thiochromene-3-sulfonamide; N-(3-amino-4-fluorophenyl)-8-ethoxy-2-oxo-2H-thiochromene-3-sulfonamide; N-(3-amino-4-fluorophenyl)-6-methoxy-2-oxo-2H-thiochromene-3-sulfonamide; N-(4-bromophenyl)-6-methoxy-2-oxo-2H-thiochromene-3-sulfonamide; 8-ethoxy-N-(4-methoxyphenyl)-2-oxo-2H-thiochromene-3-sulfonamide; N-(4-bromophenyl)-8-chloro-2-oxo-2H-thiochromene-3-sulfonamide; N-(4-bromophenyl)-8-bromo-2-oxo-2H-thiochromene-3-sulfonamide; and salts thereof.

18. A compound according to claim 15 wherein M is (b):

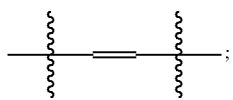
(b)

or a salt of such a compound.

19. A compound according to claim 18 selected from the group consisting of:

3-(E)-(4-methoxystyrylsulfonyl)-6-bromo-2H-thiochromen-2-one; 3-(E)-(4-chlorostyrylsulfonyl)-6-bromo-2H-thiochromen-2-one; 3-(E)-(2,4-dichlorostyrylsulfonyl)-6-bromo-2H-thiochromen-2-one; 3-(E)-(4-methoxystyrylsulfonyl)-6-chloro-2H-thiochromen-2-one; 3-(E)-(4-chlorostyrylsulfonyl)-6-chloro-2H-thiochromen-2-one; 3-(E)-(2,4-dichlorostyrylsulfonyl)-6-chloro-2H-thiochromen-2-one; 3-(E)-(4-methoxystyrylsulfonyl)-5,7-dimethoxy-2H-thiochromen-2-one; 3-(E)-(4-chlorostyrylsulfonyl)-5,7-dimethoxy-2H-thiochromen-2-one; 3-(E)-(2,4-dichlorostyrylsulfonyl)-5,7-dimethoxy-2H-thiochromen-2-one; 3-(E)-(4-methoxystyrylsulfonyl)-7-methoxy-2H-thiochromen-2-one; 3-(E)-(4-chlorostyrylsulfonyl)-7-methoxy-2H-thiochromen-2-one; 3-(E)-(2,4-dichlorostyrylsulfonyl)-7-methoxy-2H-thiochromen-2-one; 3-(Z)-(4-methoxystyrylsulfonyl)-6-bromo-2H-thiochromen-2-one; 3-(Z)-(4-chlorostyrylsulfonyl)-6-bromo-2H-thiochromen-2-one; 3-(Z)-(2,4-dichlorostyrylsulfonyl)-6-bromo-2H-thiochromen-2-one; 3-(Z)-(4-methoxystyrylsulfonyl)-6-chloro-2H-thiochromen-2-one; 3-(Z)-(4-chlorostyrylsulfonyl)-6-chloro-2H-thiochromen-2-one; 3-(Z)-(2,4-dichlorostyrylsulfonyl)-6-chloro-2H-thiochromen-2-one; 3-(Z)-(4-methoxystyrylsulfonyl)-5,7-dimethoxy-2H-thiochromen-2-one; 3-(Z)-(4-chlorostyrylsulfonyl)-5,7-dimethoxy-2H-thiochromen-2-one; 3-(Z)-(2,4-dichlorostyrylsulfonyl)-5,7-dimethoxy-2H-thiochromen-2-one; 3-(Z)-(4-methoxystyrylsulfonyl)-7-methoxy-2H-thiochromen-2-one; 3-(Z)-(4-chlorostyrylsulfonyl)-7-methoxy-2H-thiochromen-2-one; 3-(Z)-(2,4-dichlorostyrylsulfonyl)-7-methoxy-2H-thiochromen-2-one; and salts thereof.

20. A compound according to claim 15 wherein M is (c):

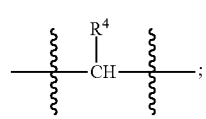
(c)

or a salt of such a compound.

21. A compound according to claim 20 selected from the group consisting of:

3-(4-methoxybenzylsulfonyl)-5,7-dimethoxy-2H-thiochromen-2-one; 3-(4-methoxybenzylsulfonyl)-6,8-dinitro-2H-thiochromen-2-one; 3-(4-methoxybenzylsulfonyl)-6-bromo-2H-thiochromen-2-one; 3-(4-methoxybenzylsulfonyl)-6-chloro-2H-thiochromen-2-one; 3-(4-methoxybenzylsulfonyl)-7-methoxy-2H-thiochromen-2-one; 3-(4-methoxybenzylsulfonyl)-7-hydroxy-2H-thiochromen-2-one; 3-(4-methoxybenzylsulfonyl)-7-chloro-2H-thiochromen-2-one; 3-(4-methoxybenzylsulfonyl)-5,7-dibromo-2H-thiochromen-2-one; 3-(4-chlorobenzylsulfonyl)-7-chloro-2H-thiochromen-2-one; 3-(4-chlorobenzylsulfonyl)-5,7-dibromo-2H-thiochromen-2-one; 3-(2,4-dichlorobenzylsulfonyl)-7-chloro-2H-thiochromen-2-one; 3-(2,4-dichlorobenzylsulfonyl)-5,7-dibromo-2H-thiochromen-2-one; 3-(4-methoxy-3-nitrobenzylsulfonyl)-5,7-dimethoxy-2H-thiochromen-2-one; 3-(4-methoxy-3-nitrobenzylsulfonyl)-7-methoxy-2H-thiochromen-2-one; 3-(4-methoxy-3-nitrobenzylsulfonyl)-7-hydroxy-2H-thiochromen-2-one; 3-(4-methoxy-3-nitrobenzylsulfonyl)-7-chloro-2H-thiochromen-2-one; 3-(4-methoxy-3-nitrobenzylsulfonyl)-5,7-dibromo-2H-thiochromen-2-one; 3-(4-chloro-3-nitrobenzylsulfonyl)-6-chloro-2H-thiochromen-2-one; 3-(4-chloro-3-nitrobenzylsulfonyl)-7-chloro-2H-thiochromen-2-one; 3-(4-chloro-3-nitrobenzylsulfonyl)-5,7-dibromo-2H-thiochromen-2-one; 3-(4-chloro-3-aminobenzylsulfonyl)-7-chloro-2H-thiochromen-2-one; 3-(4-chloro-3- aminobenzylsulfonyl)-5,7-dibromo-2H-thiochromen-2-one; 3-(4-chloro-3-aminobenzylsulfonyl)-6-chloro-2H-thiochromen-2-one; and salts thereof.

22. A compound according to claim 15 wherein M is (d) or (e):

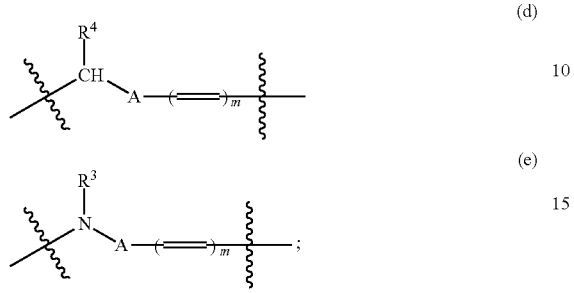

or a salt of such a compound.

23. A compound according to claim 22 selected from the group consisting of:
3-(E)-((4-methoxystyrylsulfonyl)methyl-sulfonyl)-7-chloro-2H-thiochromen-2-one; 3-(E)-((4-methoxystyrylsulfonyl)methyl-sulfonyl)-6-chloro-2H-thiochromen-2-one; 3-(E)-((4-methoxystyrylsulfonyl)methyl-sulfonyl)-6-bromo-2H-thiochromen-2-one; 3-(E)-((4-methoxystyrylsulfonyl)methyl-sulfonyl)-7-iodo-2H-thiochromen-2-one; 3-(E)-((4-methoxystyrylsulfonyl)methyl-sulfonyl)-8-ethoxy-2H-thiochromen-2-one; 3-(E)-((4-methoxystyrylsulfonyl)methyl-sulfonyl)-7-methoxy-2H-thiochromen-2-one; 3-(E)-((4-methoxystyrylsulfonyl)methyl-sulfonyl)-5-methoxy-2H-thiochromen-2-one; 3-(E)-((4-methoxystyrylsulfonyl)methyl-sulfonyl)-5,7-dimethoxy-2H-thiochromen-2-one; 3-(Z)-((4-methoxystyrylsulfonyl)methyl-sulfonyl)-7-chloro-2H-thiochromen-2-one; 3-(Z)-((4-methoxy-styrylsulfonyl)methylsulfonyl)-6-chloro-2H-thiochromen-2-one; 3-(Z)-((4-methoxystyryl-sulfonyl)methyl-sulfonyl)-6-bromo-2H-thiochromen-2-one; 3-(Z)-((4-methoxystyrylsulfonyl)-methyl-sulfonyl)-7-iodo-2H-thiochromen-2-one; 3-(Z)-((4-methoxystyrylsulfonyl)methyl-sulfonyl)-8-ethoxy-2H-thiochromen-2-one; 3-(Z)-((4-methoxystyrylsulfonyl)-methyl-sulfonyl)-7-methoxy-2H-thiochromen-2-one; 3-(Z)-((4-methoxystyrylsulfonyl)-methyl-sulfonyl)-5-methoxy-2H-thiochromen-2-one; 3-(Z)-((4-methoxystyrylsulfonyl)-methyl-sulfonyl)-5,7-dimethoxy-2H-thiochromen-2-one; 3-((E)-4-(4-methoxyphenyl)-2-oxobut-3-enylsulfonyl)-7-chloro-2H-thiochromen-2-one, 3-((E)-4-(4-methoxyphenyl)-2-oxobut-3-enylsulfonyl)-6-chloro-2H-thiochromen-2-one; 3-((E)-4-(4-methoxyphenyl)-2-oxobut-3-enylsulfonyl)-6-bromo-2H-thiochromen-2-one; 3-((E)-4-(4-methoxyphenyl)-2-oxobut-3-enylsulfonyl)-6-iodo-2H-thiochromen-2-one; 3-((E)-4-(4-methoxyphenyl)-2-oxobut-3-enylsulfonyl)-8-ethoxy-2H-thiochromen-2-one; 3-((E)-4-(4-methoxyphenyl)-2-oxobut-3-enylsulfonyl)-7-methoxy-2H-thiochromen-2-one; 3-((E)-4-(4-methoxyphenyl)-2-oxobut-3-enylsulfonyl)-5-methoxy-2H-thiochromen-2-one; 3-((E)-4-(4-methoxyphenyl)-2-oxobut-3-enylsulfonyl)-5,7-dimethoxy-2H-thiochromen-2-one; 3-((Z)-4-(4-methoxyphenyl)-2-oxobut-3-enylsulfonyl)-7-chloro-2H-thiochromen-2-one, 3-((Z)-4-(4-methoxyphenyl)-2-oxobut-3-enylsulfonyl)-6-chloro-2H-thiochromen-2-one; 3-((Z)-4-(4-methoxyphenyl)-2-oxobut-3-enylsulfonyl)-6-bromo-2H-thiochromen-2-one; 3-((Z)-4-(4-methoxyphenyl)-2-oxobut-3-enylsulfonyl)-6-iodo-2H-thiochromen-2-one; 3-((Z)-4-(4-methoxyphenyl)-2-oxobut-3-enylsulfonyl)-8-ethoxy-2H-thiochromen-2-one; 3-((Z)-4-(4-methoxyphenyl)-2-oxobut-3-enylsulfonyl)-7-methoxy-2H-thiochromen-2-one; 3-((Z)-4-(4-methoxyphenyl)-2-oxobut-3-enylsulfonyl)-5-methoxy-2H-thiochromen-2-one; 3-((Z)-4-(4-methoxyphenyl)-2-oxobut-3-enylsulfonyl)-5,7-dimethoxy-2H-thiochromen-2-one; and salts thereof.

24. A compound according to Formula I:

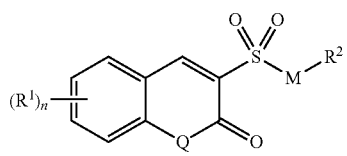

wherein:

each Q is independently O or S;

each $R^1$ is independently selected from the group consisting of halogen, $-(C_1-C_8)$hydrocarbyl, $-C(=O)R^y$, $-NR^w{}_2$, $-N(R^w)C(=O)R^y$, $-N(R^w)CH(R^z)C=O)R^y$, $-N(R^w)SO_2R^y$, $-N(R^w)(C_1-C_4)$alkylene-$CO_2R^w$, $-NO_2$, $-CN$, $-OR^w$, $-OC(=O)R^y$, $-OCH(R^z)C(=O)R^y$, $-OSO_2R^y$, $-O(C_1-C_4)$alkylene-$CO_2R^w$, $-OP(=O)(OR^w)_2$, $-O(C_2-C_6)$alkylene-$N(CH_3)_2$, $-O(C_1-C_6)$haloalkyl, $-P(=O)(OR^w)_2$, $-SO_2N(R^w)R^x$, $-NHC(=NH)NHR^x$, $-(C_1-C_6)$haloalkyl and heteroalkyl;

wherein two hydrocarbyl $R^1$ groups on adjacent carbon atoms of the phenyl ring of I may combine to form a phenyl ring fused to the compound of Formula I at the 5-6, the 6-7, or the 7-8 bond;

$R^w$ is $-H$;

$R^x$ is $-H$, $-(C_1-C_8)$hydrocarbyl or $-C(=O)(C_1-C_8)$hydrocarbyl;

$R^y$ is selected from the group consisting of $-H$, $-(C_1-C_8)$hydrocarbyl, $-O(C_1-C_8)$hydrocarbyl, substituted phenyl, substituted heterocyclyl$(C_1-C_3)$alkyl, heteroaryl$(C_1-C_3)$alkyl, $-(C_2-C_{10})$heteroalkyl, $-(C_1-C_6)$haloalkyl, $-CH(R^z)NHR^x$, $-N(R^w)R^x$, $-(C_1-C_3)$alkyleneNH$_2$, $-(C_1-C_3)$alkyleneN(CH$_3$)$_2$, $-(C_1-C_3)$perfluoroalkyleneN(CH$_3$)$_2$, $-(C_1-C_3)$alkyleneN$^+$((C$_1$-C$_3$)alkyl)$_3$, $-(C_1-C_3)$alkylene-N$^+$(CH$_2$CH$_2$OH)$_3$, $-(C_1-C_3)$alkylene-OR$^x$, $-(C_1-C_4)$alkylene-CO$_2$R$^x$, $-(C_1-C_4)$alkylene-CO$_2$N(R$^w$)R$^x$, $-(C_1-C_4)$alkylene-C(=O)halogen, halo(C$_1$-C$_3$)alkyl and $-(C_1-C_4)$perfluoroalkylene-CO$_2$R$^x$;

$R^z$ is selected from the group consisting of $-H$, $-(C_1-C_6)$alkyl, $-(CH_2)_3-NH-C(NH_2)(=NH)$, $-CH_2C(=O)NH_2$, $-CH_2COOH$, $-CH_2SH$, $-(CH_2)_2C(=O)-NH_2$, $-(CH_2)_2CO_2H$, $-CH_2$-(2-imidazolyl), $-(CH_2)_4-NH_2$, $-(CH_2)_2-S-CH_3$, phenyl, $-CH_2$-phenyl, $-CH_2-OH$, $-CH(OH)-CH_3$, $-CH_2$-(3-indolyl) and $-CH_2$-(4-hydroxyphenyl);

n is 1, 2, 3 or 4;

M is selected from the group consisting of (b), (c), (d) and (e):

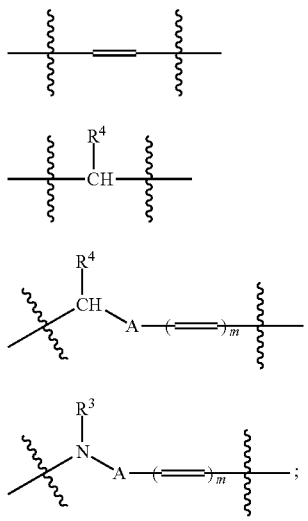

R² is substituted or unsubstituted aryl;
R³ and R⁴ are independently selected from the group consisting of —H and —($C_1$-$C_6$)alkyl;
A is —$SO_2$— or —C(=O)—; and
m is 1;
or a salt thereof.

25. A compound according to claim 24 selected from the group consisting of 3-(4-methoxy-3-nitrobenzylsulfonyl)-7-hydroxy-2H-chromen-2-one; 3-(4-methoxybenzyl-sulfonyl)-7-hydroxy-2H-thiochromen-2-one; 3-(4-methoxy-3-nitrobenzylsulfonyl)-7-hydroxy-2H-thiochromen-2-one; and salts thereof.

26. A pharmaceutical composition comprising a pharmaceutically acceptable carrier and a compound, or pharmaceutically acceptable salt thereof, according to claim 1.

27. A pharmaceutical composition comprising a pharmaceutically acceptable carrier and a compound, or pharmaceutically acceptable salt thereof, according to claim 24.

* * * * *